(12) United States Patent
Skirgaila et al.

(10) Patent No.: US 10,590,399 B2
(45) Date of Patent: Mar. 17, 2020

(54) DNA POLYMERASES

(71) Applicant: Thermo Fisher Scientific Baltics UAB, Vilnius (LT)

(72) Inventors: Remigijus Skirgaila, Vilnius (LT);
Agne Tubelevičiūtė, Vilnius (LT);
Renata Rimšelienė, Vilnius (LT);
Sigitas Burinskas, Vilnius (LT)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 8 days.

(21) Appl. No.: 15/280,077

(22) Filed: Sep. 29, 2016

(65) Prior Publication Data
US 2017/0081646 A1 Mar. 23, 2017

Related U.S. Application Data

(62) Division of application No. 13/564,940, filed on Aug. 2, 2012, now Pat. No. 9,493,848.

(30) Foreign Application Priority Data

Aug. 3, 2011 (GB) .................................. 1113430.1

(51) Int. Cl.
*C12N 9/12* (2006.01)
(52) U.S. Cl.
CPC .... *C12N 9/1252* (2013.01); *C12Y 207/07007* (2013.01); *C07K 2319/21* (2013.01)
(58) Field of Classification Search
None
See application file for complete search history.

(56) References Cited

U.S. PATENT DOCUMENTS

| | | | |
|---|---|---|---|
| 5,466,591 A | 11/1995 | Abramson et al. | |
| 5,614,365 A | 3/1997 | Tabor et al. | |
| 6,214,557 B1 | 4/2001 | Barnes et al. | |
| 6,265,193 B1 | 7/2001 | Brandis et al. | |
| 6,395,524 B2 | 5/2002 | Loeb et al. | |
| 6,602,695 B2 | 8/2003 | Patel et al. | |
| 2006/0223067 A1 | 10/2006 | Vatta et al. | |
| 2007/0020653 A1 | 1/2007 | Holliger et al. | |
| 2007/0172861 A1 | 7/2007 | Hardin et al. | |
| 2008/0014609 A1 | 1/2008 | Jestin et al. | |
| 2009/0305292 A1 | 12/2009 | Holliger et al. | |
| 2010/0112645 A1 | 5/2010 | Clark et al. | |
| 2011/0027833 A1 | 2/2011 | Hogrefe et al. | |
| 2011/0281305 A1 | 11/2011 | Bourn et al. | |

FOREIGN PATENT DOCUMENTS

| EP | 1806406 | 7/2007 |
|---|---|---|
| WO | WO 1992/003556 | 3/1992 |
| WO | WO 2001/090337 | 11/2001 |
| WO | WO 2002/022869 | 3/2002 |
| WO | WO 2005/113829 | 12/2005 |
| WO | WO 2006/034110 | 3/2008 |
| WO | WO 2010/062777 | 6/2010 |
| WO | WO 2010/062779 | 6/2010 |
| WO | WO 2011/014885 | 2/2011 |
| WO | WO 2012/097318 | 7/2012 |

OTHER PUBLICATIONS

Search Report of the United Kingdom Intellectual Property Office for GB Application No. 1113430.1, dated Nov. 29, 2011.
Gudnason, et al. Comparison of multiple DNA dyes for real-time PCR: effects of dye concentration and sequence composition on DNA amplification and melting temperature. Nucleic Acids Res, vol. 35, No. 19 (2007), e127 (8 pages).
Kermekchievet al. Mutants of Taq DNA polymerase resistant to PCR inhibitors allow DNA amplification from whole blood and crude soil samples. Nucleic Acids Res, vol. 37, No. 5 (2009), e40 (14 pages).
Kranaster R. Engineered DNA polymerases in biotechnology. ChemBioChem., vol. 11, No. 15 (2010), pp. 2077-2084.
Leconte, A.M. et al. Directed Evolution of DNA Polymerases for Next-Generation Sequencing. Angew Chem Int Ed Engl, 2010, 49, pp. 5921-5924.
Nath, K. et al., Effects of ethidium bromide and SYBR Green I on different polymerase chain reaction systems. J Biochem Biophys Methods, vol. 42 (2000), pp. 15-29.
Zaccolo, M. et al. An approach to random mutagenesis of DNA using mixtures of triphosphate derivatives of nucleoside analogues. J Mol Biol, vol. 255, No. 4 (1996), pp. 589-603.
Zhang, Z. et al.(2010). Direct DNA amplification from crude clinical samples using a PCR enhancer cocktail and novel mutants of Taq. Journal of Molecular Diagnostics, vol. 12, No. 2 (2010) 152-161.
Zipper, H. et al. Investigations on DNA intercalation and surface binding by SYBR Green I, its structure determination and methodological implications. Nucleic Acids Res, vol. 32, No. 12 (2004) e103 (10 pages).
Partial European Search Report regarding App. No. 12179055.4, dated Nov. 2, 2012, 8 pages.
Extended European Search Report 12179055.4, dated Feb. 6, 2013.
Uniprot, Accession No. B6VAJ4, Jun. 2011, www.uniprot.org.

(Continued)

*Primary Examiner* — Robert B Mondesi
*Assistant Examiner* — Todd M Epstein

(57) ABSTRACT

A DNA polymerase mutant comprising a Taq DNA polymerase amino acid sequence with a mutation at one or more of the following selected amino acid positions: E189K, E230K, E507K, H28R, L30R, G38R, F73V, H75R, E76A, E76G, E76K, E90K, K206R, E315K, A348V, L351F, A439T, D452N, G504S, E507A, D551N, L552R, I553V, D578N, H676R, Q680R, D732G, E734G, E734K, F749V; wherein the polymerase mutant exhibits relative to wild-type DNA polymerase increased polymerase speed, increased affinity to DNA substrate and/or increased resistance to a DNA polymerase inhibitor; and wherein, when the mutation is E507K in combination with two or more further mutations or the mutation is Q680R in combination with four or more further mutations, at least one of the further mutations is at one of the selected amino acid positions; and when the mutation is I553V, this is not in combination with D551S.

21 Claims, 30 Drawing Sheets
Specification includes a Sequence Listing.

(56) References Cited

OTHER PUBLICATIONS

Kim et al., "Top DNA Polymerase from Thermus Thermophilus HB27: Gene Cloning, Sequence Determination, and Physiochemical Properties," Mol. Cells, 1988, 9, pp. 157-161.
U.S. Appl. No. 61/432,936, filed Jan. 14, 2011.
File History of U.S. Appl. No. 13/564,940, filed Aug. 2, 2012.

The amino acids sequence of wild type Taq DNA polymerase used for expression and mutagenesis (SEQ ID 13).

```
>wt
MRGMLPLFEPKGRVLLVDGHHLAYRTFHALKGLTTSRGEPVQAVYGFAKSLLKALKEDGD
AVIVVFDAKAPSFRHEAYGGYKAGRAPTPEDFPRQLALIKELVDLLGLARLEVPGYEADD
VLASLAKKAEKEGYEVRILTADKDLYQLLSDRIHVLHPEGYLITPAWLWEKYGLRPDQWA
DYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWP
PPEGAFVGFVLSRKEPMWADLLALAAARGGRVHRAPEPYKALRDLKEARGLLAKDLSVLA
LREGLGLPPGDDPMLLAYLLDPSNTTPEGVARRYGGEWTEEAGERAALSERLFANLWGRL
EGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQYRELTK
LKSTYIDPLPDLIHPRTGRLHTRFNQTATATGRLSSSDPNLQNIPVRTPLGQRIRRAFIA
EEGWLLVALDYSQIELRVLAHLSGDENLIRVFQEGRDIHTETASWMFGVPREAVDPLMRR
AAKTINFGVLYGMSAHRLSQELAIPYEEAQAFIERYFQSFPKVRAWIEKTLEEGRRRGYV
ETLFGRRRYVPDLEARVKSVREAAERMAFNMPVQGTAADLMKLAMVKLFPRLEEMGARML
LQVHDELVLEAPKERAEAVARLAKEVMEGVYPLAVPLEVEVGIGEDWLSAKE
```

*Fig. 1*

The PCR of 250 bp amplicon performed with wt His-Taq polymerase and pool of mutant polymerases at different SYBR Green I concentrations (SYBR Green I stock concentration is 10'000X and amplification was performed using 0.2-4X concentration of dye).

The sequencing results of Taq DNA polymerase mutants selected after high-throughput screening for SYBR Green I resistance (Example 1).

| | | |
|---|---|---|
| Group15 (L6M28_1) | 8 mutations, | 26T->P, 36S->R, 90E->K, 141A->T, 184A->V, 290S->G, 490L->P, 507E->A |
| Group16 (L6M29_1) | 7 mutations, | 20H->P, 89P->Q, 172Y->C, 492R->K, 515S->R, 738K->R, 788V->A |
| Group2 (L6M1_1) | 6 mutations, | 28H->R, 43A->P, 253P->S, 445E->G, 551D->A, 827W->* |
| Group10 (L6M12_1) | 6 mutations, | 118A->V, 191D->N, 230E->K, 237D->G, 663K->E, 821V->M |
| Group11 (L6M15_1) | 6 mutations, | 28H->R, 190S->F, 196V->A, 520E->G, 732D->G, 780L->P |
| Group25 (L6M57_1) | 6 mutations, | 27F->L, 85R->W, 225K->R, 507E->K, 592Q->R, 757A->T |
| Group29 (Taq_C11) | 6 mutations, | 57E->G, 97A->V, 127K->E, 230E->K, 247K->T, 507E->K |
| Group4 (L6M3_1) | 5 mutations, | 38G->R, 56K->T, 59G->R, 315E->K, 680Q->R |
| Group14 (L6M27_1) | 5 mutations, | 2R->K, 6P->S, 27F->S, 28H->R, 315E->G |
| Group21 (L6M34_1) | 5 mutations, | 215E->D, 225K->R, 382P->S, 608A->V, 672G->D |
| Group32 (Taq_H12) | 5 mutations, | 189E->K, 266R->W, 449V->M, 480H->R, 521A->V |
| Group5 (L6M4_1) | 4 mutations, | 147Q->*, 210E->A, 360A->T, 678L->P |
| Group13 (L6M26_1) | 4 mutations, | 72S->F, 230E->G, 401E->K, 454A->T |
| Group18 (L6M31_1) | 4 mutations, | 197K->R, 543S->G, 676H->R, 722T->A |
| Group19 (L6M32_1) | 4 mutations, | 78Y->C, 507E->K, 529V->A, 705A->V |
| Group28 (Taq_B1) | 4 mutations, | 30L->P, 433V->M, 507E->K, 774E->G |
| Group31 (Taq_G6(07), Taq_E2) | 4 mutations, | 27F->L, 28H->R, 189E->K, 206K->R |
| Group6 (L6M5_1) | 3 mutations, | 96L->F, 230E->K, 799V->A |
| Group7 (L6M7_1) | 3 mutations, | 38G->R, 90E->K, 568A->T |
| Group9 (L6M11_1) | 3 mutations, | 33L->R, 62V->A, 219K->R |
| Group12 (L6M25_1) | 3 mutations, | 28H->R, 551D->N, 580N->S |
| Group22 (L6M39_1) | 3 mutations, | 28H->R, 447T->A, 680Q->R |
| Group26 (L6M61_1) | 3 mutations, | 24Y->H, 93P->L, 552L->R |
| Group27 (L6M66_1, Taq_C6(gr)) | 3 mutations, | 76E->G, 219K->R, 507E->K |
| Group30 (Taq_E6) | 3 mutations, | 82K->R, 296E->G, 553I->V |
| Group33 (Taq_E11) | 3 mutations, | 76E->G, 389G->R, 578D->N |
| Group34 (Taq_B8(gr)) | 3 mutations, | 219K->R, 389G->R, 507E->K |
| Group17 (L6M30_1) | 2 mutations, | 253P->S, 507E->A |
| Group24 (L6M46_1) | 2 mutations, | 368P->L, 507E->K |
| Group3 (L6M2_1) | 1 mutation, | 26T->A |
| Group8 (L6M8_1) | 1 mutation, | 507E->A |
| Group20 (L6M33_1) | 1 mutation, | 709K->T |
| Group23 (L6M40_1, Taq_B3, Taq_A4) | 1 mutation, | 507E->K |

*Fig. 3*

The frequency of mutations found during high-throughput screening of Taq DNA polymerase for SYBR Green I resistance (Example 1).

Position 507, total mutations 14, 2 different amino acids
    E->A, 3 sequences (L6M8_1, L6M28_1, L6M30_1)
    E->K, 11 sequences (L6M32_1, L6M40_1, L6M46_1, L6M57_1, L6M66_1, Taq_B1, Taq_C11, Taq_B3, Taq_A4, Taq_C6(gr), Taq_B8(gr))
Position 28, total mutations 6, 1 different amino acids
    H->R, 6 sequences (L6M15_1, L6M25_1, L6M27_1, L6M39_1, Taq_G6(07), Taq_E2)
Position 27, total mutations 4, 2 different amino acids
    F->S, 1 sequences (L6M27_1)
    F->L, 3 sequences (L6M57_1, Taq_G6(07), Taq_E2)
Position 219, total mutations 4, 1 different amino acids
    K->R, 4 sequences (L6M11_1, L6M66_1, Taq_C6(gr), Taq_B8(gr))
Position 230, total mutations 4, 2 different amino acids
    E->G, 1 sequences (L6M26_1)
    E->K, 3 sequences (L6M5_1, L6M12_1, Taq_C11)
Position 76, total mutations 3, 1 different amino acids
    E->G, 3 sequences (L6M66_1, Taq_E11, Taq_C6(gr))
Position 189, total mutations 3, 1 different amino acids
    E->K, 3 sequences (Taq_G6(07), Taq_H12, Taq_E2)
Position 26, total mutations 2, 2 different amino acids
    T->P, 1 sequences (L6M28_1)
    T->A, 1 sequences (L6M2_1)
Position 38, total mutations 2, 1 different amino acids
    G->R, 2 sequences (L6M3_1, L6M7_1)
Position 90, total mutations 2, 1 different amino acids
    E->K, 2 sequences (L6M7_1, L6M28_1)
Position 206, total mutations 2, 1 different amino acids
    K->R, 2 sequences (Taq_G6(07), Taq_E2)
Position 225, total mutations 2, 1 different amino acids
    K->R, 2 sequences (L6M34_1, L6M57_1)
Position 315, total mutations 2, 2 different amino acids
    E->G, 1 sequences (L6M27_1)
    E->K, 1 sequences (L6M3_1)
Position 389, total mutations 2, 1 different amino acids
    G->R, 2 sequences (Taq_E11, Taq_B8(gr))
Position 680, total mutations 2, 1 different amino acids
    Q->R, 2 sequences (L6M3_1, L6M39_1)
Position 2, total mutations 1, 1 different amino acids
    R->K, 1 sequences (L6M27_1)
Position 6, total mutations 1, 1 different amino acids
    P->S, 1 sequences (L6M27_1)
Position 20, total mutations 1, 1 different amino acids
    H->P, 1 sequences (L6M29_1)
Position 24, total mutations 1, 1 different amino acids
    Y->H, 1 sequences (L6M61_1)
Position 30, total mutations 1, 1 different amino acids
    L->P, 1 sequences (Taq_B1)
Position 33, total mutations 1, 1 different amino acids
    L->R, 1 sequences (L6M11_1)
Position 36, total mutations 1, 1 different amino acids
    S->R, 1 sequences (L6M28_1)
Position 56, total mutations 1, 1 different amino acids
    K->T, 1 sequences (L6M3_1)
Position 57, total mutations 1, 1 different amino acids
    E->G, 1 sequences (Taq_C11)
Position 59, total mutations 1, 1 different amino acids
    G->R, 1 sequences (L6M3_1)
Position 62, total mutations 1, 1 different amino acids
    V->A, 1 sequences (L6M11_1)
Position 72, total mutations 1, 1 different amino acids
    S->F, 1 sequences (L6M26_1)

*Fig. 4-1*

Position 78, total mutations 1, 1 different amino acids
 Y->C, 1 sequences (L6M32_1)
Position 82, total mutations 1, 1 different amino acids
 K->R, 1 sequences (Taq_E6)
Position 85, total mutations 1, 1 different amino acids
 R->W, 1 sequences (L6M57_1)
Position 89, total mutations 1, 1 different amino acids
 P->Q, 1 sequences (L6M29_1)
Position 93, total mutations 1, 1 different amino acids
 P->L, 1 sequences (L6M61_1)
Position 96, total mutations 1, 1 different amino acids
 L->F, 1 sequences (L6M5_1)
Position 97, total mutations 1, 1 different amino acids
 A->V, 1 sequences (Taq_C11)
Position 118, total mutations 1, 1 different amino acids
 A->V, 1 sequences (L6M12_1)
Position 127, total mutations 1, 1 different amino acids
 K->E, 1 sequences (Taq_C11)
Position 141, total mutations 1, 1 different amino acids
 A->T, 1 sequences (L6M28_1)
Position 172, total mutations 1, 1 different amino acids
 Y->C, 1 sequences (L6M29_1)
Position 184, total mutations 1, 1 different amino acids
 A->V, 1 sequences (L6M28_1)
Position 190, total mutations 1, 1 different amino acids
 S->F, 1 sequences (L6M15_1)
Position 191, total mutations 1, 1 different amino acids
 D->N, 1 sequences (L6M12_1)
Position 196, total mutations 1, 1 different amino acids
 V->A, 1 sequences (L6M15_1)
Position 197, total mutations 1, 1 different amino acids
 K->R, 1 sequences (L6M31_1)
Position 215, total mutations 1, 1 different amino acids
 E->D, 1 sequences (L6M34_1)
Position 237, total mutations 1, 1 different amino acids
 D->G, 1 sequences (L6M12_1)
Position 247, total mutations 1, 1 different amino acids
 K->T, 1 sequences (Taq_C11)
Position 253, total mutations 1, 1 different amino acids
 P->S, 1 sequences (L6M30_1)
Position 266, total mutations 1, 1 different amino acids
 R->W, 1 sequences (Taq_H12)
Position 290, total mutations 1, 1 different amino acids
 S->G, 1 sequences (L6M28_1)
Position 296, total mutations 1, 1 different amino acids
 E->G, 1 sequences (Taq_E6)
Position 368, total mutations 1, 1 different amino acids
 P->L, 1 sequences (L6M46_1)
Position 382, total mutations 1, 1 different amino acids
 P->S, 1 sequences (L6M34_1)
Position 401, total mutations 1, 1 different amino acids
 E->K, 1 sequences (L6M26_1)
Position 433, total mutations 1, 1 different amino acids
 V->M, 1 sequences (Taq_B1)
Position 447, total mutations 1, 1 different amino acids
 T->A, 1 sequences (L6M39_1)
Position 449, total mutations 1, 1 different amino acids
 V->M, 1 sequences (Taq_H12)
Position 454, total mutations 1, 1 different amino acids
 A->T, 1 sequences (L6M26_1)
Position 480, total mutations 1, 1 different amino acids
 H->R, 1 sequences (Taq_H12)
Position 490, total mutations 1, 1 different amino acids
 L->P, 1 sequences (L6M28_1)

*Fig. 4-2*

Position 492, total mutations 1, 1 different amino acids
    R->K, 1 sequences (L6M29_1)
Position 515, total mutations 1, 1 different amino acids
    S->R, 1 sequences (L6M29_1)
Position 520, total mutations 1, 1 different amino acids
    E->G, 1 sequences (L6M15_1)
Position 521, total mutations 1, 1 different amino acids
    A->V, 1 sequences (Taq_H12)
Position 529, total mutations 1, 1 different amino acids
    V->A, 1 sequences (L6M32_1)
Position 543, total mutations 1, 1 different amino acids
    S->G, 1 sequences (L6M31_1)
Position 551, total mutations 1, 1 different amino acids
    D->N, 1 sequences (L6M25_1)
Position 552, total mutations 1, 1 different amino acids
    L->R, 1 sequences (L6M61_1)
Position 553, total mutations 1, 1 different amino acids
    I->V, 1 sequences (Taq_E6)
Position 568, total mutations 1, 1 different amino acids
    A->T, 1 sequences (L6M7_1)
Position 578, total mutations 1, 1 different amino acids
    D->N, 1 sequences (Taq_E11)
Position 580, total mutations 1, 1 different amino acids
    N->S, 1 sequences (L6M25_1)
Position 592, total mutations 1, 1 different amino acids
    Q->R, 1 sequences (L6M57_1)
Position 608, total mutations 1, 1 different amino acids
    A->V, 1 sequences (L6M34_1)
Position 663, total mutations 1, 1 different amino acids
    K->E, 1 sequences (L6M12_1)
Position 672, total mutations 1, 1 different amino acids
    G->D, 1 sequences (L6M34_1)
Position 676, total mutations 1, 1 different amino acids
    H->R, 1 sequences (L6M31_1)
Position 705, total mutations 1, 1 different amino acids
    A->V, 1 sequences (L6M32_1)
Position 709, total mutations 1, 1 different amino acids
    K->T, 1 sequences (L6M33_1)
Position 722, total mutations 1, 1 different amino acids
    T->A, 1 sequences (L6M31_1)
Position 732, total mutations 1, 1 different amino acids
    D->G, 1 sequences (L6M15_1)
Position 738, total mutations 1, 1 different amino acids
    K->R, 1 sequences (L6M29_1)
Position 757, total mutations 1, 1 different amino acids
    A->T, 1 sequences (L6M57_1)
Position 774, total mutations 1, 1 different amino acids
    E->G, 1 sequences (Taq_B1)
Position 780, total mutations 1, 1 different amino acids
    L->P, 1 sequences (L6M15_1)
Position 788, total mutations 1, 1 different amino acids
    V->A, 1 sequences (L6M29_1)
Position 799, total mutations 1, 1 different amino acids
    V->A, 1 sequences (L6M5_1)
Position 821, total mutations 1, 1 different amino acids
    V->M, 1 sequences (L6M12_1)

*Fig. 4-3*

The PCR of 200 bp amplicon from plasmid DNA performed with wt His-Taq polymerase and single amino acid mutant polymerases at different SYBR Green I concentrations (SYBR Green I stock concentration is 10'000X and amplification was performed using 0.2-5X concentration of dye).

The PCR of 500 bp amplicon from human genomic DNA performed with wt His-Taq polymerase and single amino acid mutant polymerases at different SYBR Green I concentrations (SYBR Green I stock concentration is 10'000X and amplification was performed using 0.2-5X concentration of dye).

Polyacrylamide gel electrophoresis pictures of electrophoretic mobility shift assay (EMSA). Polymerase affinity to substrate (Kd) was measured using radioactively labeled DNA substrate at 0.1 nM concentration and 0.25-100 nM protein concentration gradient.

Polyacrylamide gel electrophoresis pictures of electrophoretic mobility shift assay (EMSA). Polymerase affinity to substrate (Kd) in the presence of 0.2X SYBR Green I dye was measured using radioactively labeled DNA substrate at 0.1 nM concentration and 0.25-100 nM protein concentration gradient.

The sequence of plasmid1 used as a PCR target for of 250 bp and 200 bp DNA fragments amplification in Example 1 (SEQ ID 14).

```
LOCUS       plasmid1      5487 bp   DNA    circular    3-APR-2006
BASE COUNT    1652 a     1103 c    1340 g    1392 t
ORIGIN
    1 tttgctcaca tgacccgaca ccatcgaatg gccagatgat taattcctaa tttttgttga
   61 cactctatca ttgatagagt tattttacca ctccctatca gtgatagaga aaagtgaaat
  121 gaatagttcg acaaaaatct agataacgag ggcaaaaaat ggctagctgg agccacccgc
  181 agttcgaaaa aggcgccatg atactggaca ctgattacat aacaaaagat ggtaaaccta
  241 taatccgaat ttttaagaaa gagaacggggg agtttaaaat agaacttgat ccccattttc
  301 agccctatat atatgctctt ctcaaagatg actccgctat tgaggagata aaggcaataa
  361 agggcgagag acatggaaaa agtgtgagag tagttgatgc agtgaaagtc aagaagaaat
  421 ttttgggaag ggaagttgag gtctggaagc ttatatttga acaccctcaa gacgttccgg
  481 ctatgaggga caagataaaa gagcatccag ctgttatcga catttacgaa tatgatatac
  541 catttgccaa gcgttatctc atagacaagg gcttgattcc tatggaggga gacgaggagc
  601 ttaagctcct cgcctttgac attgaaacgt tttatcatga aggagatgaa tttggaaaag
  661 gcgagataat aatgattagt tatgccgacg aagaagaggc cagagtaatt acatggaaaa
  721 atatcgatct gccgtatgtc gatgttgtat ccaatgaaag ggagatgata aagcgctttg
  781 ttcaggttgt taaagaaaaa gacccggatg tgataataac ttacaatggg gacaattttg
  841 atttgccgta tctcataaaa cgggcagaaa agctgggggt tcggcttgtc ttaggaaggg
  901 acaaggaaaa tcccgaaccc aagatccaga gaatgggggga tagcttcgct gtagaaatca
  961 agggcagaat acattttgat cttttcccag ttgtgagaag gacaataaac cttccgacgt
 1021 atacgcttga ggcggtttat gaagcagttt tgggaaaaac caaaagcaaa ttaggagcgg
 1081 aggaaattgc cgccatctgg gaaacggaag agagcatgaa aaaactggcc cagtactcaa
 1141 tggaagatgc tagggcgact tatgagctcg gaaaggaatt cttccccatg gaagctgagc
 1201 tggcgaagct gataggtcaa agcgtgtggg atgtctctag gtcaagcacc ggcaacctcg
 1261 tggagtggta tttgttaagg gtggcatatg agaggaacga gcttgctccg aacaaacctg
 1321 atgaggaaga gtataaaaga cgtttaagaa caacttacct gggaggatat gtaaaagagc
 1381 cagaaaaggg tttatgggag aacatcatct atcttgactt ccgtagcttg tatccctcaa
 1441 taatagttac ccataacgta tcgccggaca ctctcgaaaa agagggttgc gaaaattatg
 1501 atattgctcc catagtaagc tataggttct gcaaggactt tccgggcttt attccctcca
 1561 tactcgggga cttaattgca atgaggcaag agataaagaa gaaaatgaaa gctacaattg
 1621 atccagtgga aaggaaaatg cttgattata gacaacgggc agttaaatta cttgcaaata
 1681 gttattacgg ttatatgggg tatcctaagg caagatggta ctcgaaggaa tgtgccgaaa
 1741 gtgttaccgc atggggaagg cactacatag atgatgacgat aaaagaaata gaggaaaaat
 1801 ttggcttttaa agttctttat gcagacaccg acgggttta tgcgacaata tcaggagaaa
 1861 aaccggaaat tattaaaaag aaagccaggg agttcctaaa ctacataaac tctaaacttc
 1921 caggtctgct tgagcttgag tatgagggct tttacttgag aggattcttt gttacaaaaa
 1981 agcgctatgc agtcatagat gaagagggca gaataacaac aagggggcttg gaagtagtaa
 2041 ggagggactg gagtgaaata gctaaagaga ctcaggcaaa ggttttagag gctatactta
 2101 aagatggaag tgttgaaaaa gctgtagaaa ttgttagaga tgttttagag aaaatagcaa
 2161 aatacagggt tccacttgaa aagcttgtta tccatgagca gattaccagg gatttaaagg
```

Fig. 9-1

```
2221 actacaaagc cattggtcct catgtagcga tagcaaaaag actagccgca agagggataa
2281 aagtgaaacc gggcacaata ataagctata tcgttctcaa aggaagcgga aagataagcg
2341 atagggtaat tttacttaca gaatacgatc ctgaaaagca caagtacgat ccagattact
2401 acatagaaaa ccaagttttg ccggcagtac ttagaatcct tgaagcattt ggatatagaa
2461 aggaggattt aagatatcaa agctcaaaac aaaccggctt agatgcatgg ctcaaaaggt
2521 gatatctaac taagcttgac ctgtgaagtg aaaaatggcg cacattgtgc gacatttttt
2581 ttgtctgccg tttaccgcta ctgcgtcacg gatctccacg cgccctgtag cggcgcatta
2641 agcgcggcgg gtgtggtggt tacgcgcagc gtgaccgcta cacttgccag cgccctagcg
2701 cccgctcctt tcgctttctt cccttccttt ctcgccacgt tcgccggctt tccccgtcaa
2761 gctctaaatc gggggctccc tttagggttc cgatttagtg ctttacggca cctcgacccc
2821 aaaaaacttg attagggtga tggttcacgt agtgggccat cgccctgata cacggttttt
2881 cgcccttttga cgttggagtc cacgttcttt aatagtggac tcttgttcca aactggaaca
2941 acactcaacc ctatctcggt ctattctttt gatttataag ggattttgcc gatttcggcc
3001 tattggttaa aaaatgagct gatttaacaa aaatttaacg cgaattttaa caaaatatta
3061 acgcttacaa tttcaggtgg cacttttcgg ggaaatgtgc gcggaacccc tatttgttta
3121 ttttttctaaa tacattcaaa tatgtatccg ctcatgagac aataaccctg ataaatgctt
3181 caataatatt gaaaaaggaa gagtatgagt attcaacatt tccgtgtcgc ccttattccc
3241 ttttttgcgg catttttgcct tcctgttttt gctcacccag aaacgctggt gaaagtaaaa
3301 gatgctgaag atcagttggg tgcacgagtg ggttacatcg aactggatct caacagcggt
3361 aagatccttg agagttttcg ccccgaagaa cgttttccaa tgatgagcac ttttaaagtt
3421 ctgctatgtg gcgcggtatt atcccgtatt gacgccgggc aagagcaact cggtcgccgc
3481 atacactatt ctcagaatga cttggttgag tactcaccag tcacagaaaa gcatcttacg
3541 gatggcatga cagtaagaga attatgcagt gctgccataa ccatgagtga taacactgcg
3601 gccaacttac ttctgacaac gatcggagga ccgaaggagc taaccgcttt tttgcacaac
3661 atgggggatc atgtaactcg ccttgatcgt tgggaaccgg agctgaatga agccatacca
3721 aacgacgagc gtgacaccac gatgcctgta gcaatggcaa caacgttgcg caaactatta
3781 actggcgaac tacttactct agcttcccgg caacaattga tagactggat ggaggcggat
3841 aaagttgcag gaccacttct gcgctcggcc cttccggctg gctggtttat tgctgataaa
3901 tctggagccg gtgagcgtgg ctctcgcggt atcattgcag cactggggcc agatggtaag
3961 ccctcccgta tcgtagttat ctacacgacg gggagtcagg caactatgga tgaacgaaat
4021 agacagatcg ctgagatagg tgcctcactg attaagcatt ggtaggaatt aatgatgtct
4081 cgtttagata aagtaaagt gattaacagc gcattagagc tgcttaatga ggtcggaatc
4141 gaaggtttaa caacccgtaa actcgcccag aagctaggt tagagcagcc tacattgtat
4201 tggcatgtaa aaataagcg gctttgctc gacgccttag ccattgagat gttagatagg
4261 caccatactc acttttgccc tttagaaggg gaaagctggc aagatttttt acgtaataac
4321 gctaaaagtt ttagatgtgc tttactaagt catcgcgatg gagcaaaagt acatttaggt
4381 acacggccta cagaaaaaca gtatgaaact ctcgaaaatc aattagcctt tttatgccaa
4441 caaggttttt cactagagaa tgcattatat gcactcagcg cagtgggcca tttacttta
4501 ggttgcgtat tggaagatca agagcatcaa gtcgctaaag aagaaaggga aacacctact
4561 actgatagta tgccgccatt attacgacaa gctatcgaat tatttgatca ccaaggtgca
4621 gagccagcct tcttattcgg ccttgaattg atcatatgcg gattagaaaa acaacttaaa
4681 tgtgaaagtg ggtcttaaaa gcagcataac cttttccgt gatggtaact tcactagttt
4741 aaaaggatct aggtgaagat ccttttgat aatctcatga ccaaaatccc ttaacgtgag
4801 ttttcgttcc actgagcgtc agaccccgta gaaaagatca aaggatcttc ttgagatcct
4861 ttttttctgc gcgtaatctg ctgcttgcaa acaaaaaaac caccgctacc agcggtggtt
```

*Fig. 9-2*

4921 tgtttgccgg atcaagagct accaactctt tttccgaagg taactggctt cagcagagcg
4981 cagataccaa atactgtcct tctagtgtag ccgtagttag gccaccactt caagaactct
5041 gtagcaccgc ctacatacct cgctctgcta atcctgttac cagtggctgc tgccagtggc
5101 gataagtcgt gtcttaccgg gttggactca agacgatagt taccggataa ggcgcagcgg
5161 tcgggctgaa cggggggttc gtgcacacag cccagcttgg agcgaacgac ctacaccgaa
5221 ctgagatacc tacagcgtga gctatgagaa agcgccacgc ttcccgaagg gagaaaggcg
5281 gacaggtatc cggtaagcgg cagggtcgga acaggagagc gcacgaggga gcttccaggg
5341 ggaaacgcct ggtatcttta tagtcctgtc gggtttcgcc acctctgact tgagcgtcga
5401 tttttgtgat gctcgtcagg ggggcggagc ctatggaaaa acgccagcaa cgcggccttt
5461 ttacggttcc tggccttttg ctggcct

*Fig. 9-3*

The sequencing results of Taq DNA polymerase mutants selected after first high-throughput screening of Taq DNA polymerase L0 library for shorter amplification and annealing times (Example 2).

| Group | Mutations | Details |
|---|---|---|
| Group41 (L8-42) | 12 mutations, | 30L->P, 37R->L, 45Y->H, 100K->R, 155V->I, 230E->K, 268R->G, 332V->I, 452D->N, 504G->S, 505K->*, 680Q->K |
| Group11 (L8-10) | 9 mutations, | 3G->E, 30L->R, 104D->N, 136V->I, 306F->S, 385T->I, 407A->T, 532I->T, 645W->* |
| Group28 (L8-27) | 9 mutations, | 30L->R, 82K->E, 137R->C, 230E->K, 283H->L, 452D->N, 504G->S, 694E->K, 795R->G |
| Group3 (L8-2) | 8 mutations, | 230E->K, 403G->R, 419R->K, 452D->N, 504G->S, 680Q->K, 695R->C, 698Q->R |
| Group13 (L8-12) | 8 mutations, | 3G->E, 66F->L, 77A->T, 230E->K, 239L->P, 399T->M, 425R->K, 832E->G |
| Group29 (L8-28) | 8 mutations, | 30L->R, 230E->K, 266R->Q, 283H->R, 335A->V, 385T->I, 680Q->R, 747M->V |
| Group16 (L8-15) | 7 mutations, | 30L->P, 155V->I, 214L->P, 230E->K, 446A->T, 452D->N, 504G->S |
| Group17 (L8-16) | 7 mutations, | 30L->P, 230E->K, 238D->N, 241L->P, 311L->R, 470L->P, 623S->P |
| Group45 (L8-46) | 7 mutations, | 30L->P, 205R->G, 230E->K, 452D->N, 504G->S, 507E->G, 806V->A |
| Group2 (L8-1) | 6 mutations, | 3G->E, 30L->R, 230E->K, 499G->E, 657L->R, 739S->G |
| Group7 (L8-6) | 6 mutations, | 30L->P, 36S->G, 230E->K, 452D->N, 504G->S, 707I->T |
| Group8 (L8-7) | 6 mutations, | 30L->P, 37R->W, 151D->N, 197K->R, 285F->S, 474V->I |
| Group19 (L8-18) | 6 mutations, | 30L->R, 230E->K, 452D->N, 504G->S, 664T->A, 799V->A |
| Group22 (L8-21) | 6 mutations, | 28H->R, 30L->Q, 192N->D, 230E->K, 443H->R, 701P->L |
| Group24 (L8-23) | 6 mutations, | 30L->P, 132E->G, 230E->K, 311L->F, 348A->V, 461L->R |
| Group27 (L8-26) | 6 mutations, | 29A->T, 30L->R, 162L->H, 230E->K, 474V->I, 755G->D |
| Group30 (L8-29) | 6 mutations, | 230E->K, 244D->N, 452D->N, 504G->S, 676H->R, 779M->V |
| Group39 (L8-38) | 6 mutations, | 24Y->H, 189E->K, 230E->K, 255E->K, 532I->T, 749F->I |
| Group42 (L8-43) | 6 mutations, | 30L->P, 230E->K, 311L->F, 348A->V, 461L->R, 788V->A |
| Group43 (L8-44) | 6 mutations, | 20H->R, 30L->P, 206K->R, 230E->K, 248V->A, 452D->N |
| Group50 (L8-52) | 6 mutations, | 30L->P, 137R->H, 230E->K, 311L->F, 452D->N, 504G->S |
| Group5 (L8-4) | 5 mutations, | 2R->K, 230E->K, 333H->R, 504G->S, 825E->K |
| Group6 (L8-5) | 5 mutations, | 30L->P, 230E->K, 452D->N, 504G->S, 518V->A |
| Group12 (L8-11) | 5 mutations, | 30L->P, 189E->K, 264P->S, 631V->A, 739S->G |
| Group15 (L8-14) | 5 mutations, | 30L->P, 230E->K, 452D->N, 504G->S, 507E->G |
| Group20 (L8-19) | 5 mutations, | 30L->P, 65V->A, 230E->K, 311L->F, 348A->V |
| Group23 (L8-22) | 5 mutations, | 30L->P, 230E->K, 335A->T, 507E->A, 636R->W |
| Group26 (L8-25) | 5 mutations, | 30L->R, 124S->G, 230E->K, 452D->N, 504G->S |
| Group31 (L8-30) | 5 mutations, | 189E->K, 262R->W, 285F->S, 470L->F, 802L->R |
| Group35 (L8-34) | 5 mutations, | 30L->P, 230E->K, 277E->K, 534Q->R, 749F->I |
| Group36 (L8-35) | 5 mutations, | 30L->R, 97A->S, 189E->K, 230E->K, 678L->P |
| Group38 (L8-37) | 5 mutations, | 230E->K, 450R->H, 552L->F, 772L->P, 799V->A |
| Group4 (L8-3) | 4 mutations, | 30L->R, 183R->G, 197K->R, 315E->G |
| Group9 (L8-8) | 4 mutations, | 30L->P, 155V->I, 471E->K, 664T->A |
| Group10 (L8-9, L8-39) | 4 mutations, | 30L->P, 230E->K, 452D->N, 504G->S |
| Group21 (L8-20) | 4 mutations, | 30L->R, 285F->S, 452D->N, 507E->A |
| Group33 (L8-32) | 4 mutations, | 30L->P, 230E->K, 452D->N, 552L->F |
| Group48 (L8-50) | 4 mutations, | 30L->P, 114P->L, 230E->K, 452D->N |
| Group49 (L8-51) | 4 mutations, | 30L->P, 361L->M, 452D->N, 504G->S |
| Group14 (L8-13) | 3 mutations, | 221L->P, 230E->K, 383S->F |
| Group18 (L8-17) | 2 mutations, | 230E->K, 791A->T |
| Group25 (L8-24) | 2 mutations, | 30L->R, 507E->A |

*Fig. 10*

The frequency of mutations found during first high-throughput screening of Taq DNA polymerase L0 library for shorter amplification and annealing times (Example 2).

```
Position 230, total mutations 33, 1 different amino acids
        E->K, 33 sequences (L8-1, L8-2, L8-4, L8-5, L8-6, L8-9, L8-12, L8-13, L8-14, L8-15, L8-16, L8-17, L8-18, L8-19, L8-21, L8-
22, L8-23, L8-25, L8-26, L8-27, L8-28, L8-29, L8-32, L8-34, L8-35, L8-37, L8-38, L8-39, L8-43, L8-44, L8-46, L8-50, L8-52)
Position 30, total mutations 32, 3 different amino acids
        L->Q, 1 sequences (L8-21)
        L->P, 21 sequences (L8-5, L8-6, L8-7, L8-8, L8-9, L8-11, L8-14, L8-15, L8-16, L8-19, L8-22, L8-23, L8-32, L8-34, L8-39, L8-
43, L8-44, L8-46, L8-50, L8-51, L8-52)
        L->R, 10 sequences (L8-1, L8-3, L8-18, L8-20, L8-24, L8-25, L8-26, L8-27, L8-28, L8-35)
Position 452, total mutations 18, 1 different amino acids
        D->N, 18 sequences (L8-2, L8-5, L8-6, L8-9, L8-14, L8-15, L8-18, L8-20, L8-25, L8-27, L8-29, L8-32, L8-39, L8-44, L8-46,
L8-50, L8-51, L8-52)
Position 504, total mutations 15, 1 different amino acids
        G->S, 15 sequences (L8-2, L8-4, L8-5, L8-6, L8-9, L8-14, L8-15, L8-18, L8-25, L8-27, L8-29, L8-39, L8-46, L8-51, L8-52)
Position 311, total mutations 5, 2 different amino acids
        L->F, 4 sequences (L8-19, L8-23, L8-43, L8-52)
        L->R, 1 sequences (L8-16)
Position 507, total mutations 5, 2 different amino acids
        E->G, 2 sequences (L8-14, L8-46)
        E->A, 3 sequences (L8-20, L8-22, L8-24)
Position 189, total mutations 4, 1 different amino acids
        E->K, 4 sequences (L8-11, L8-30, L8-35, L8-38)
Position 285, total mutations 3, 1 different amino acids
        F->S, 3 sequences (L8-7, L8-20, L8-30)
Position 348, total mutations 3, 1 different amino acids
        A->V, 3 sequences (L8-19, L8-23, L8-43)
Position 3, total mutations 2, 1 different amino acids
        G->E, 2 sequences (L8-1, L8-12)
Position 137, total mutations 2, 2 different amino acids
        R->C, 1 sequences (L8-27)
        R->H, 1 sequences (L8-52)
Position 155, total mutations 2, 1 different amino acids
        V->I, 2 sequences (L8-8, L8-15)
Position 197, total mutations 2, 1 different amino acids
        K->R, 2 sequences (L8-3, L8-7)
Position 283, total mutations 2, 2 different amino acids
        H->R, 1 sequences (L8-28)
        H->L, 1 sequences (L8-27)
Position 335, total mutations 2, 2 different amino acids
        A->T, 1 sequences (L8-22)
        A->V, 1 sequences (L8-28)
Position 461, total mutations 2, 1 different amino acids
        L->R, 2 sequences (L8-23, L8-43)
Position 470, total mutations 2, 2 different amino acids
        L->F, 1 sequences (L8-30)
        L->P, 1 sequences (L8-16)
Position 474, total mutations 2, 1 different amino acids
        V->I, 2 sequences (L8-7, L8-26)
Position 552, total mutations 2, 1 different amino acids
        L->F, 2 sequences (L8-32, L8-37)
Position 664, total mutations 2, 1 different amino acids
        T->A, 2 sequences (L8-8, L8-18)
Position 680, total mutations 2, 2 different amino acids
        Q->R, 1 sequences (L8-28)
        Q->K, 1 sequences (L8-2)
Position 739, total mutations 2, 1 different amino acids
        S->G, 2 sequences (L8-1, L8-11)
Position 749, total mutations 2, 1 different amino acids
        F->I, 2 sequences (L8-34, L8-38)
```

*Fig. 11-1*

Position 799, total mutations 2, 1 different amino acids
    V->A, 2 sequences (L8-18, L8-37)
Position 2, total mutations 1, 1 different amino acids
    R->K, 1 sequences (L8-4)
Position 20, total mutations 1, 1 different amino acids
    H->R, 1 sequences (L8-44)
Position 24, total mutations 1, 1 different amino acids
    Y->H, 1 sequences (L8-38)
Position 28, total mutations 1, 1 different amino acids
    H->R, 1 sequences (L8-21)
Position 29, total mutations 1, 1 different amino acids
    A->T, 1 sequences (L8-26)
Position 36, total mutations 1, 1 different amino acids
    S->G, 1 sequences (L8-6)
Position 37, total mutations 1, 1 different amino acids
    R->W, 1 sequences (L8-7)
Position 65, total mutations 1, 1 different amino acids
    V->A, 1 sequences (L8-19)
Position 66, total mutations 1, 1 different amino acids
    F->L, 1 sequences (L8-12)
Position 77, total mutations 1, 1 different amino acids
    A->T, 1 sequences (L8-12)
Position 82, total mutations 1, 1 different amino acids
    K->E, 1 sequences (L8-27)
Position 97, total mutations 1, 1 different amino acids
    A->S, 1 sequences (L8-35)
Position 114, total mutations 1, 1 different amino acids
    P->L, 1 sequences (L8-50)
Position 124, total mutations 1, 1 different amino acids
    S->G, 1 sequences (L8-25)
Position 132, total mutations 1, 1 different amino acids
    E->G, 1 sequences (L8-23)
Position 151, total mutations 1, 1 different amino acids
    D->N, 1 sequences (L8-7)
Position 162, total mutations 1, 1 different amino acids
    L->H, 1 sequences (L8-26)
Position 183, total mutations 1, 1 different amino acids
    R->G, 1 sequences (L8-3)
Position 192, total mutations 1, 1 different amino acids
    N->D, 1 sequences (L8-21)
Position 205, total mutations 1, 1 different amino acids
    R->G, 1 sequences (L8-46)
Position 206, total mutations 1, 1 different amino acids
    K->R, 1 sequences (L8-44)
Position 214, total mutations 1, 1 different amino acids
    L->P, 1 sequences (L8-15)
Position 221, total mutations 1, 1 different amino acids
    L->P, 1 sequences (L8-13)
Position 238, total mutations 1, 1 different amino acids
    D->N, 1 sequences (L8-16)
Position 239, total mutations 1, 1 different amino acids
    L->P, 1 sequences (L8-12)
Position 241, total mutations 1, 1 different amino acids
    L->P, 1 sequences (L8-16)
Position 244, total mutations 1, 1 different amino acids
    D->N, 1 sequences (L8-29)
Position 248, total mutations 1, 1 different amino acids
    V->A, 1 sequences (L8-44)
Position 255, total mutations 1, 1 different amino acids
    E->G, 1 sequences (L8-38)
Position 262, total mutations 1, 1 different amino acids
    R->W, 1 sequences (L8-30)
Position 264, total mutations 1, 1 different amino acids
    P->S, 1 sequences (L8-11)
Position 266, total mutations 1, 1 different amino acids
    R->Q, 1 sequences (L8-28)

*Fig. 11-2*

Position 277, total mutations 1, 1 different amino acids
　　　　E->K, 1 sequences (L8-34)
Position 315, total mutations 1, 1 different amino acids
　　　　E->G, 1 sequences (L8-3)
Position 333, total mutations 1, 1 different amino acids
　　　　H->R, 1 sequences (L8-4)
Position 361, total mutations 1, 1 different amino acids
　　　　L->M, 1 sequences (L8-51)
Position 383, total mutations 1, 1 different amino acids
　　　　S->F, 1 sequences (L8-13)
Position 385, total mutations 1, 1 different amino acids
　　　　T->I, 1 sequences (L8-28)
Position 399, total mutations 1, 1 different amino acids
　　　　T->M, 1 sequences (L8-12)
Position 403, total mutations 1, 1 different amino acids
　　　　G->R, 1 sequences (L8-2)
Position 419, total mutations 1, 1 different amino acids
　　　　R->K, 1 sequences (L8-2)
Position 425, total mutations 1, 1 different amino acids
　　　　R->K, 1 sequences (L8-12)
Position 443, total mutations 1, 1 different amino acids
　　　　H->R, 1 sequences (L8-21)
Position 446, total mutations 1, 1 different amino acids
　　　　A->T, 1 sequences (L8-15)
Position 450, total mutations 1, 1 different amino acids
　　　　R->H, 1 sequences (L8-37)
Position 471, total mutations 1, 1 different amino acids
　　　　E->K, 1 sequences (L8-8)
Position 499, total mutations 1, 1 different amino acids
　　　　G->E, 1 sequences (L8-1)
Position 518, total mutations 1, 1 different amino acids
　　　　V->A, 1 sequences (L8-5)
Position 532, total mutations 1, 1 different amino acids
　　　　I->V, 1 sequences (L8-38)
Position 534, total mutations 1, 1 different amino acids
　　　　Q->R, 1 sequences (L8-34)
Position 623, total mutations 1, 1 different amino acids
　　　　S->P, 1 sequences (L8-16)
Position 631, total mutations 1, 1 different amino acids
　　　　V->A, 1 sequences (L8-11)
Position 636, total mutations 1, 1 different amino acids
　　　　R->W, 1 sequences (L8-22)
Position 657, total mutations 1, 1 different amino acids
　　　　L->R, 1 sequences (L8-1)
Position 676, total mutations 1, 1 different amino acids
　　　　H->R, 1 sequences (L8-29)
Position 678, total mutations 1, 1 different amino acids
　　　　L->P, 1 sequences (L8-35)
Position 694, total mutations 1, 1 different amino acids
　　　　E->K, 1 sequences (L8-27)
Position 695, total mutations 1, 1 different amino acids
　　　　R->C, 1 sequences (L8-2)
Position 698, total mutations 1, 1 different amino acids
　　　　Q->R, 1 sequences (L8-2)
Position 701, total mutations 1, 1 different amino acids
　　　　P->L, 1 sequences (L8-21)
Position 707, total mutations 1, 1 different amino acids
　　　　I->T, 1 sequences (L8-6)
Position 747, total mutations 1, 1 different amino acids
　　　　M->V, 1 sequences (L8-28)
Position 755, total mutations 1, 1 different amino acids
　　　　G->D, 1 sequences (L8-26)
Position 772, total mutations 1, 1 different amino acids
　　　　L->P, 1 sequences (L8-37)
Position 779, total mutations 1, 1 different amino acids
　　　　M->V, 1 sequences (L8-29)

*Fig. 11-3*

Position 788, total mutations 1, 1 different amino acids
V->A, 1 sequences (L8-43)
Position 791, total mutations 1, 1 different amino acids
A->T, 1 sequences (L8-17)
Position 795, total mutations 1, 1 different amino acids
R->G, 1 sequences (L8-27)
Position 802, total mutations 1, 1 different amino acids
L->R, 1 sequences (L8-30)
Position 806, total mutations 1, 1 different amino acids
V->A, 1 sequences (L8-46)
Position 825, total mutations 1, 1 different amino acids
E->K, 1 sequences (L8-4)
Position 832, total mutations 1, 1 different amino acids
E->G, 1 sequences (L8-12)

*Fig. 11-4*

The sequencing results of Taq DNA polymerase mutants selected after second high-throughput screening of Taq DNA polymerase L3 library for shorter amplification and annealing times (Example 2).

| | | |
|---|---|---|
| Group17 (3-8) | 10 mutations, | 30L->P, 75H->R, 92F->L, 147Q->R, 177D->G, 226P->S, 237D->G, 267E->G, 431R->Q, 640T->A |
| Group35 (G5-12) | 10 mutations, | 73F->V, 102L->Q, 144D->G, 206K->R, 260K->E, 351L->F, 397E->K, 463V->A, 487R->W, 698Q->R |
| Group16 (3-5) | 9 mutations, | 24Y->H, 57E->G, 73F->S, 303E->G, 310V->M, 568A->V, 692F->I, 720V->A, 820E->V |
| Group22 (4-4) | 9 mutations, | 33L->R, 65V->I, 275R->G, 326A->T, 333H->Y, 452D->N, 592Q->R, 634E->G, 742E->A |
| Group10 (2-2) | 8 mutations, | 69K->Q, 297A->V, 439A->T, 462E->G, 551D->G, 612S->R, 680Q->R, 773E->G |
| Group12 (2-12) | 8 mutations, | 73F->V, 144D->G, 206K->R, 351L->F, 397E->K, 411R->G, 551D->G, 734E->K |
| Group34 (G5-11) | 8 mutations, | 65V->I, 73F->V, 118A->V, 144D->G, 206K->R, 507E->K, 515S->N, 630R->Q |
| Group5 (1-7) | 7 mutations, | 15L->F, 33L->P, 251D->G, 278F->L, 312S->F, 707I->M, 717R->W |
| Group29 (4-15) | 7 mutations, | 56K->E, 90E->G, 174L->Q, 351L->F, 439A->T, 507E->A, 698Q->R |
| Group32 (G5-8) | 7 mutations, | 46G->D, 80G->R, 230E->A, 236M->I, 366G->S, 547D->G, 745E->A |
| Group9 (1-11) | 6 mutations, | 24Y->H, 110R->C, 400E->K, 461L->R, 553I->V, 752P->S |
| Group21 (4-3) | 6 mutations, | 50S->D, 64V->A, 134Y->C, 238D->G, 722T->A, 767K->E |
| Group27 (4-12) | 6 mutations, | 50S->G, 61A->V, 132E->K, 206K->R, 284E->A, 385T->A |
| Group33 (G5-10) | 6 mutations, | 75H->R, 91D->G, 132E->G, 244D->G, 311L->F, 420L->F |
| Group3 (1-4) | 5 mutations, | 131K->R, 141A->V, 173G->S, 303E->G, 461L->R |
| Group4 (1-5) | 5 mutations, | 75H->R, 197K->R, 278F->L, 344D->N, 734E->G |
| Group7 (1-9) | 5 mutations, | 26T->A, 339Y->S, 492R->G, 732D->G, 814A->T |
| Group11 (2-5) | 5 mutations, | 143K->E, 189E->K, 311L->P, 592Q->R, 646M->I |
| Group14 (3-3) | 5 mutations, | 30L->P, 168L->P, 175R->G, 568A->V, 720V->A |
| Group18 (3-9) | 5 mutations, | 30L->P, 55L->P, 206K->R, 245L->P, 543S->N |
| Group20 (4-2) | 5 mutations, | 18D->G, 141A->T, 243W->R, 530E->G, 664T->A |
| Group30 (G5-1) | 5 mutations, | 314K->R, 439A->T, 538L->F, 577S->P, 799V->A |
| Group31 (G5-6) | 5 mutations, | 67D->G, 245L->R, 415N->D, 502A->T, 676H->R |
| Group36 (G5-17) | 5 mutations, | 28H->P, 144D->G, 212G->R, 275R->G, 406A->V |
| Group38 (G5-23) | 5 mutations, | 143K->E, 189E->K, 516A->T, 685P->S, 732D->G |
| Group6 (1-8) | 4 mutations, | 90E->G, 289G->G, 344D->N, 549L->S |
| Group13 (3-2) | 4 mutations, | 27F->S, 57E->G, 73F->L, 214L->P |
| Group24 (4-6) | 4 mutations, | 292K->R, 418G->E, 432E->K, 596R->Q |
| Group25 (4-7) | 4 mutations, | 144D->N, 176P->S, 503I->V, 567T->M |
| Group37 (G5-19) | 4 mutations, | 230E->K, 518V->A, 749F->L, 765M->T |
| Group2 (1-2) | 3 mutations, | 55L->P, 134Y->C, 246A->T |
| Group8 (1-10) | 3 mutations, | 52L->P, 143K->R, 397E->G |
| Group15 (3-4) | 3 mutations, | 26T->P, 212G->R, 246A->V |
| Group23 (4-5) | 3 mutations, | 6P->L, 38G->R, 367L->F |
| Group28 (4-14) | 3 mutations, | 29A->T, 97A->T, 209E->K |
| Group19 (3-11) | 2 mutations, | 90E->G, 749F->V |
| Group26 (4-8) | 2 mutations, | 76E->G, 304G->E |

*Fig. 12*

The frequency of mutations found during second high-throughput screening of Taq DNA polymerase L3 library for shorter amplification and annealing times (Example 2).

Position 73, total mutations 5, 3 different amino acids
    F->V, 3 sequences (2-12, G5-11, G5-12)
    F->S, 1 sequences (3-5)
    F->L, 1 sequences (3-2)
Position 144, total mutations 5, 2 different amino acids
    D->G, 4 sequences (2-12, G5-11, G5-12, G5-17)
    D->N, 1 sequences (4-7)
Position 206, total mutations 5, 1 different amino acids
    K->R, 5 sequences (2-12, 3-9, 4-12, G5-11, G5-12)
Position 30, total mutations 3, 1 different amino acids
    L->P, 3 sequences (3-3, 3-8, 3-9)
Position 75, total mutations 3, 1 different amino acids
    H->R, 3 sequences (1-5, 3-8, G5-10)
Position 90, total mutations 3, 1 different amino acids
    E->G, 3 sequences (1-8, 3-11, 4-15)
Position 143, total mutations 3, 2 different amino acids
    K->E, 2 sequences (2-5, G5-23)
    K->R, 1 sequences (1-10)
Position 351, total mutations 3, 1 different amino acids
    L->F, 3 sequences (2-12, 4-15, G5-12)
Position 397, total mutations 3, 2 different amino acids
    E->G, 1 sequences (1-10)
    E->K, 2 sequences (2-12, G5-12)
Position 439, total mutations 3, 1 different amino acids
    A->T, 3 sequences (2-2, 4-15, G5-1)
Position 24, total mutations 2, 1 different amino acids
    Y->H, 2 sequences (1-11, 3-5)
Position 26, total mutations 2, 2 different amino acids
    T->P, 1 sequences (3-4)
    T->A, 1 sequences (1-9)
Position 33, total mutations 2, 2 different amino acids
    L->P, 1 sequences (1-7)
    L->R, 1 sequences (4-4)
Position 50, total mutations 2, 2 different amino acids
    S->D, 1 sequences (4-3)
    S->G, 1 sequences (4-12)
Position 55, total mutations 2, 1 different amino acids
    L->P, 2 sequences (1-2, 3-9)
Position 57, total mutations 2, 1 different amino acids
    E->G, 2 sequences (3-2, 3-5)
Position 65, total mutations 2, 1 different amino acids
    V->I, 2 sequences (4-4, G5-11)
Position 132, total mutations 2, 2 different amino acids
    E->G, 1 sequences (G5-10)
    E->K, 1 sequences (4-12)
Position 134, total mutations 2, 1 different amino acids
    Y->C, 2 sequences (1-2, 4-3)
Position 141, total mutations 2, 2 different amino acids
    A->T, 1 sequences (4-2)
    A->V, 1 sequences (1-4)
Position 189, total mutations 2, 1 different amino acids
    E->K, 2 sequences (2-5, G5-23)
Position 212, total mutations 2, 1 different amino acids
    G->R, 2 sequences (3-4, G5-17)
Position 230, total mutations 2, 2 different amino acids
    E->A, 1 sequences (G5-8)
    E->K, 1 sequences (G5-19)

*Fig. 13-1*

Position 245, total mutations 2, 2 different amino acids
    L->P, 1 sequences (3-9)
    L->R, 1 sequences (G5-6)
Position 246, total mutations 2, 2 different amino acids
    A->T, 1 sequences (1-2)
    A->V, 1 sequences (3-4)
Position 275, total mutations 2, 1 different amino acids
    R->G, 2 sequences (4-4, G5-17)
Position 278, total mutations 2, 1 different amino acids
    F->L, 2 sequences (1-5, 1-7)
Position 303, total mutations 2, 1 different amino acids
    E->G, 2 sequences (1-4, 3-5)
Position 311, total mutations 2, 2 different amino acids
    L->F, 1 sequences (G5-10)
    L->P, 1 sequences (2-5)
Position 344, total mutations 2, 1 different amino acids
    D->N, 2 sequences (1-5, 1-8)
Position 461, total mutations 2, 1 different amino acids
    L->R, 2 sequences (1-4, 1-11)
Position 507, total mutations 2, 2 different amino acids
    E->A, 1 sequences (4-15)
    E->K, 1 sequences (G5-11)
Position 551, total mutations 2, 1 different amino acids
    D->G, 2 sequences (2-2, 2-12)
Position 568, total mutations 2, 1 different amino acids
    A->V, 2 sequences (3-3, 3-5)
Position 592, total mutations 2, 1 different amino acids
    Q->R, 2 sequences (2-5, 4-4)
Position 698, total mutations 2, 1 different amino acids
    Q->R, 2 sequences (4-15, G5-12)
Position 720, total mutations 2, 1 different amino acids
    V->A, 2 sequences (3-3, 3-5)
Position 732, total mutations 2, 1 different amino acids
    D->G, 2 sequences (1-9, G5-23)
Position 734, total mutations 2, 2 different amino acids
    E->G, 1 sequences (1-5)
    E->K, 1 sequences (2-12)
Position 749, total mutations 2, 2 different amino acids
    F->V, 1 sequences (3-11)
    F->L, 1 sequences (G5-19)
Position 6, total mutations 1, 1 different amino acids
    P->L, 1 sequences (4-5)
Position 15, total mutations 1, 1 different amino acids
    L->F, 1 sequences (1-7)
Position 18, total mutations 1, 1 different amino acids
    D->G, 1 sequences (4-2)
Position 27, total mutations 1, 1 different amino acids
    F->S, 1 sequences (3-2)
Position 28, total mutations 1, 1 different amino acids
    H->P, 1 sequences (G5-17)
Position 29, total mutations 1, 1 different amino acids
    A->T, 1 sequences (4-14)
Position 38, total mutations 1, 1 different amino acids
    G->R, 1 sequences (4-5)
Position 46, total mutations 1, 1 different amino acids
    G->D, 1 sequences (G5-8)
Position 52, total mutations 1, 1 different amino acids
    L->P, 1 sequences (1-10)
Position 56, total mutations 1, 1 different amino acids
    K->E, 1 sequences (4-15)
Position 61, total mutations 1, 1 different amino acids
    A->V, 1 sequences (4-12)
Position 64, total mutations 1, 1 different amino acids
    V->A, 1 sequences (4-3)
Position 67, total mutations 1, 1 different amino acids
    D->G, 1 sequences (G5-6)

*Fig. 13-2*

Position 69, total mutations 1, 1 different amino acids
    K->Q, 1 sequences (2-2)
Position 76, total mutations 1, 1 different amino acids
    E->G, 1 sequences (4-8)
Position 80, total mutations 1, 1 different amino acids
    G->R, 1 sequences (G5-8)
Position 91, total mutations 1, 1 different amino acids
    D->G, 1 sequences (G5-10)
Position 92, total mutations 1, 1 different amino acids
    F->L, 1 sequences (3-8)
Position 97, total mutations 1, 1 different amino acids
    A->T, 1 sequences (4-14)
Position 102, total mutations 1, 1 different amino acids
    L->Q, 1 sequences (G5-12)
Position 110, total mutations 1, 1 different amino acids
    R->C, 1 sequences (1-11)
Position 118, total mutations 1, 1 different amino acids
    A->V, 1 sequences (G5-11)
Position 131, total mutations 1, 1 different amino acids
    K->R, 1 sequences (1-4)
Position 147, total mutations 1, 1 different amino acids
    Q->R, 1 sequences (3-8)
Position 168, total mutations 1, 1 different amino acids
    L->P, 1 sequences (3-3)
Position 173, total mutations 1, 1 different amino acids
    G->S, 1 sequences (1-4)
Position 174, total mutations 1, 1 different amino acids
    L->Q, 1 sequences (4-15)
Position 175, total mutations 1, 1 different amino acids
    R->G, 1 sequences (3-3)
Position 176, total mutations 1, 1 different amino acids
    P->S, 1 sequences (4-7)
Position 177, total mutations 1, 1 different amino acids
    D->G, 1 sequences (3-8)
Position 197, total mutations 1, 1 different amino acids
    K->R, 1 sequences (1-5)
Position 209, total mutations 1, 1 different amino acids
    E->K, 1 sequences (4-14)
Position 214, total mutations 1, 1 different amino acids
    L->P, 1 sequences (3-2)
Position 226, total mutations 1, 1 different amino acids
    P->S, 1 sequences (3-8)
Position 236, total mutations 1, 1 different amino acids
    M->I, 1 sequences (G5-8)
Position 237, total mutations 1, 1 different amino acids
    D->G, 1 sequences (3-8)
Position 238, total mutations 1, 1 different amino acids
    D->G, 1 sequences (4-3)
Position 243, total mutations 1, 1 different amino acids
    W->R, 1 sequences (4-2)
Position 244, total mutations 1, 1 different amino acids
    D->G, 1 sequences (G5-10)
Position 251, total mutations 1, 1 different amino acids
    D->G, 1 sequences (1-7)
Position 260, total mutations 1, 1 different amino acids
    K->E, 1 sequences (G5-12)
Position 267, total mutations 1, 1 different amino acids
    E->G, 1 sequences (3-8)
Position 284, total mutations 1, 1 different amino acids
    E->A, 1 sequences (4-12)
Position 289, total mutations 1, 1 different amino acids
    E->G, 1 sequences (1-8)
Position 292, total mutations 1, 1 different amino acids
    K->R, 1 sequences (4-6)
Position 297, total mutations 1, 1 different amino acids
    A->V, 1 sequences (2-2)

*Fig. 13-3*

Position 304, total mutations 1, 1 different amino acids
    G->E, 1 sequences (4-8)
Position 310, total mutations 1, 1 different amino acids
    V->M, 1 sequences (3-5)
Position 312, total mutations 1, 1 different amino acids
    S->F, 1 sequences (1-7)
Position 314, total mutations 1, 1 different amino acids
    K->R, 1 sequences (G5-1)
Position 326, total mutations 1, 1 different amino acids
    A->T, 1 sequences (4-4)
Position 333, total mutations 1, 1 different amino acids
    H->Y, 1 sequences (4-4)
Position 339, total mutations 1, 1 different amino acids
    Y->S, 1 sequences (1-9)
Position 366, total mutations 1, 1 different amino acids
    G->S, 1 sequences (G5-8)
Position 367, total mutations 1, 1 different amino acids
    L->F, 1 sequences (4-5)
Position 385, total mutations 1, 1 different amino acids
    T->A, 1 sequences (4-12)
Position 400, total mutations 1, 1 different amino acids
    E->K, 1 sequences (1-11)
Position 406, total mutations 1, 1 different amino acids
    A->V, 1 sequences (G5-17)
Position 411, total mutations 1, 1 different amino acids
    R->G, 1 sequences (2-12)
Position 415, total mutations 1, 1 different amino acids
    N->D, 1 sequences (G5-6)
Position 418, total mutations 1, 1 different amino acids
    G->E, 1 sequences (4-6)
Position 420, total mutations 1, 1 different amino acids
    L->F, 1 sequences (G5-10)
Position 431, total mutations 1, 1 different amino acids
    R->Q, 1 sequences (3-8)
Position 432, total mutations 1, 1 different amino acids
    E->K, 1 sequences (4-6)
Position 452, total mutations 1, 1 different amino acids
    D->N, 1 sequences (4-4)
Position 462, total mutations 1, 1 different amino acids
    E->G, 1 sequences (2-2)
Position 463, total mutations 1, 1 different amino acids
    V->A, 1 sequences (G5-12)
Position 487, total mutations 1, 1 different amino acids
    R->W, 1 sequences (G5-12)
Position 492, total mutations 1, 1 different amino acids
    R->G, 1 sequences (1-9)
Position 502, total mutations 1, 1 different amino acids
    A->T, 1 sequences (G5-6)
Position 503, total mutations 1, 1 different amino acids
    I->V, 1 sequences (4-7)
Position 515, total mutations 1, 1 different amino acids
    S->N, 1 sequences (G5-11)
Position 516, total mutations 1, 1 different amino acids
    A->T, 1 sequences (G5-23)
Position 518, total mutations 1, 1 different amino acids
    V->A, 1 sequences (G5-19)
Position 530, total mutations 1, 1 different amino acids
    E->G, 1 sequences (4-2)
Position 538, total mutations 1, 1 different amino acids
    L->F, 1 sequences (G5-1)
Position 543, total mutations 1, 1 different amino acids
    S->N, 1 sequences (3-9)
Position 547, total mutations 1, 1 different amino acids
    D->G, 1 sequences (G5-8)
Position 549, total mutations 1, 1 different amino acids
    L->S, 1 sequences (1-8)

*Fig. 13-4*

Position 553, total mutations 1, 1 different amino acids
    I->V, 1 sequences (1-11)
Position 567, total mutations 1, 1 different amino acids
    T->M, 1 sequences (4-7)
Position 577, total mutations 1, 1 different amino acids
    S->P, 1 sequences (G5-1)
Position 596, total mutations 1, 1 different amino acids
    R->Q, 1 sequences (4-6)
Position 612, total mutations 1, 1 different amino acids
    S->R, 1 sequences (2-2)
Position 630, total mutations 1, 1 different amino acids
    R->Q, 1 sequences (G5-11)
Position 634, total mutations 1, 1 different amino acids
    E->G, 1 sequences (4-4)
Position 640, total mutations 1, 1 different amino acids
    T->A, 1 sequences (3-8)
Position 646, total mutations 1, 1 different amino acids
    M->I, 1 sequences (2-5)
Position 664, total mutations 1, 1 different amino acids
    T->A, 1 sequences (4-2)
Position 676, total mutations 1, 1 different amino acids
    H->R, 1 sequences (G5-6)
Position 680, total mutations 1, 1 different amino acids
    Q->R, 1 sequences (2-2)
Position 685, total mutations 1, 1 different amino acids
    P->S, 1 sequences (G5-23)
Position 692, total mutations 1, 1 different amino acids
    F->I, 1 sequences (3-5)
Position 707, total mutations 1, 1 different amino acids
    I->M, 1 sequences (1-7)
Position 717, total mutations 1, 1 different amino acids
    R->W, 1 sequences (1-7)
Position 722, total mutations 1, 1 different amino acids
    T->A, 1 sequences (4-3)
Position 742, total mutations 1, 1 different amino acids
    E->A, 1 sequences (4-4)
Position 745, total mutations 1, 1 different amino acids
    E->A, 1 sequences (G5-8)
Position 752, total mutations 1, 1 different amino acids
    P->S, 1 sequences (1-11)
Position 765, total mutations 1, 1 different amino acids
    M->T, 1 sequences (G5-19)
Position 767, total mutations 1, 1 different amino acids
    K->E, 1 sequences (4-3)
Position 773, total mutations 1, 1 different amino acids
    E->G, 1 sequences (2-2)
Position 799, total mutations 1, 1 different amino acids
    V->A, 1 sequences (G5-1)
Position 814, total mutations 1, 1 different amino acids
    A->T, 1 sequences (1-9)
Position 820, total mutations 1, 1 different amino acids
    E->V, 1 sequences (3-5)

*Fig. 13-5*

The PCR of 1825 bp amplicon from phage lambda DNA performed with commercial Taq polymerase, wt His-Taq polymerase and single amino acid mutant polymerases: 1 - ZipRuler™ Express DNA Ladder 1 (Fermentas, #SM1373); 2 - Taq DNA Pol (Fermentas, #EP0404); 3 - His-Taq wt; 4 - His-Taq L30P; 5 - His-Taq L30R; 6 - His-Taq E230K; 7 - His-Taq D452N; 8 - His-Taq G504S; 9 - His-Taq E507K; 10 - His-Taq E189K. Three different in cycling length programs (Normal, Fast, Very fast) were used.

A - PCR was performed in $(NH_4)_2SO_4$ based buffer.

B - PCR was performed in KCl based buffer.

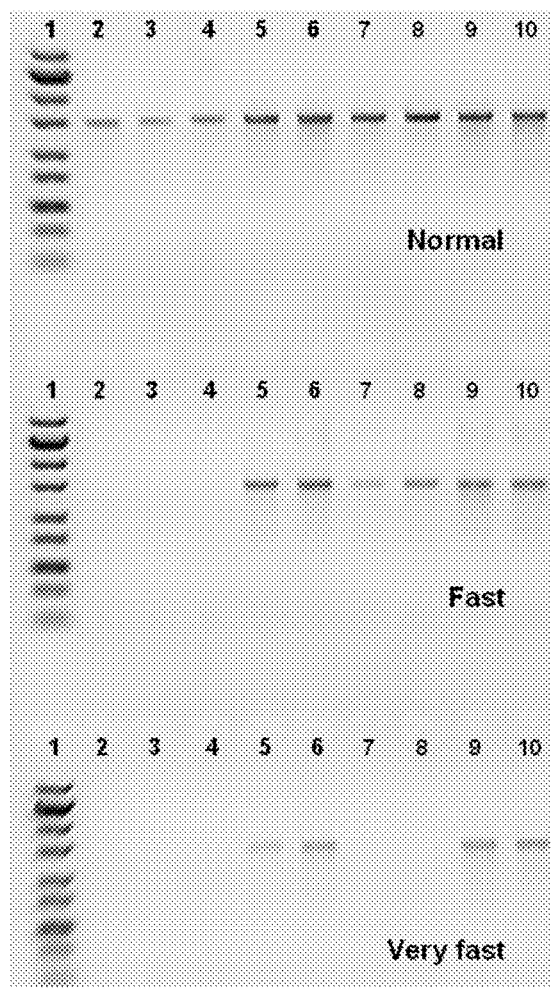

*Fig. 14A*

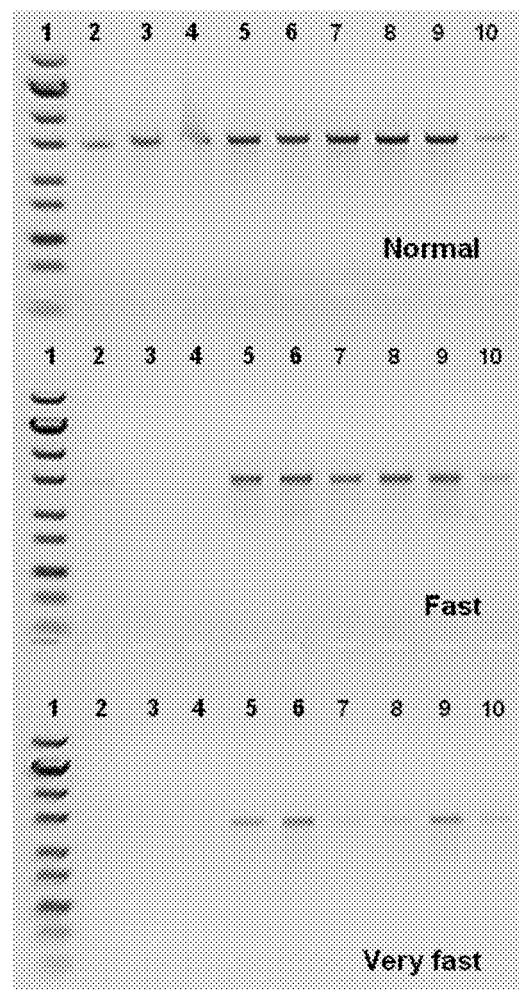

*Fig. 14B*

The PCR of 2.5 kbp amplicon from human genomic DNA performed with commercial Taq polymerase, wt His-Taq polymerase and single amino acid mutant polymerases:
1 - ZipRuler™ Express DNA Ladder 1 (Fermentas, #SM1373); 2 - Taq DNA Pol (Fermentas, #EP0404); 3 - His-Taq wt; 4 - His-Taq E189K; 5 - His-Taq E230K; 6 - His-Taq E507K.
Three different in cycling length programs (Normal, Fast, Very fast) were used.
A - PCR was performed in (NH4)2SO4 based buffer.
B - PCR was performed in KCl based buffer.

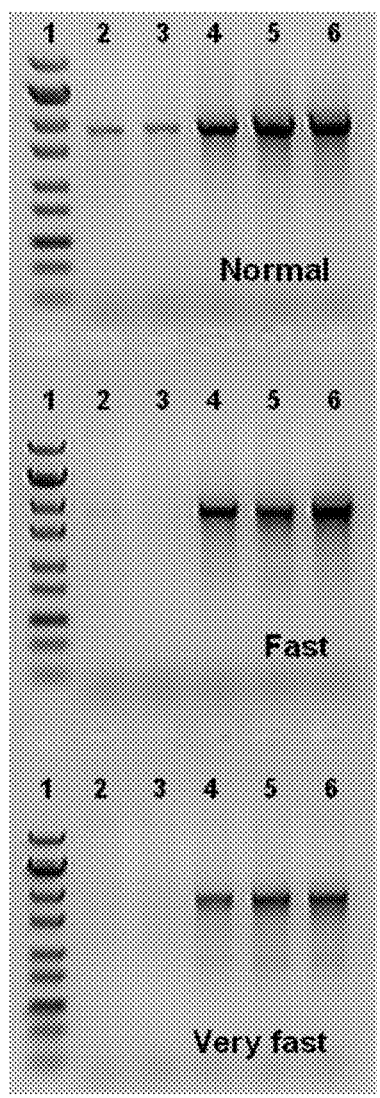
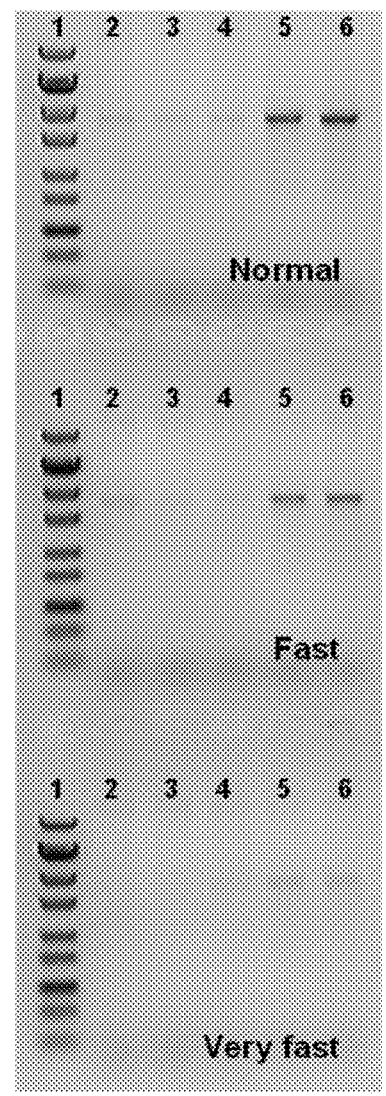

The PCR of 1.825 kbp amplicon from phage lambda DNA was performed in the presence of 0-8% of blood either with commercial Taq polymerase (Fermentas, #EP0404), or wt His-Taq polymerase, or single amino acid mutant polymerases (E189K; E230K; E507K, H28R). M - GeneRuler™ Express DNA Ladder, ready-to-use, 100-5000 bp (Fermentas, #SM1553).

Figure 17. The PCR of 1.825 kbp amplicon from phage lambda DNA was performed in the presence of 0.000-0.015% of SDS either with commercial Taq polymerase (Fermentas, #EP0404), or wt His-Taq polymerase, or single amino acid mutant polymerases (E189K; E230K; E507K, H28R). M - GeneRuler™ Express DNA Ladder, ready-to-use, 100-5000 bp (Fermentas, #SM1553).

The PCR of 1.825 kbp amplicon from phage lambda DNA was performed in the presence of 0-100 mM of GuHCl either with commercial Taq polymerase (Fermentas, #EP0404), or wt His-Taq polymerase, or single amino acid mutant polymerases (E189K; E230K; E507K, H28R). M - GeneRuler™ Express DNA Ladder, ready-to-use, 100-5000 bp (Fermentas, #SM1553).

The PCR of 1.825 kbp amplicon from phage lambda DNA was performed in the presence of 0-0,039 UPS heparin (per 25 μl of PCR reaction) either with commercial Taq polymerase (Fermentas, #EP0404), or wt His-Taq polymerase, or single amino acid mutant polymerases (E189K; E230K; E507K, D452N; D551N; G504S). M - GeneRuler™ Express DNA Ladder, ready-to-use, 100-5000 bp (Fermentas, #SM1553).

1 - no heparin;
2 - 0,001 UPS heparin (per 25 μl of PCR reaction);
3 - 0,0025 UPS heparin (per 25 μl of PCR reaction);
4 - 0,00625 UPS heparin (per 25 μl of PCR reaction);
5 - 0,015625 UPS heparin (per 25 μl of PCR reaction);
6 - 0,039 UPS heparin (per 25 μl of PCR reaction).

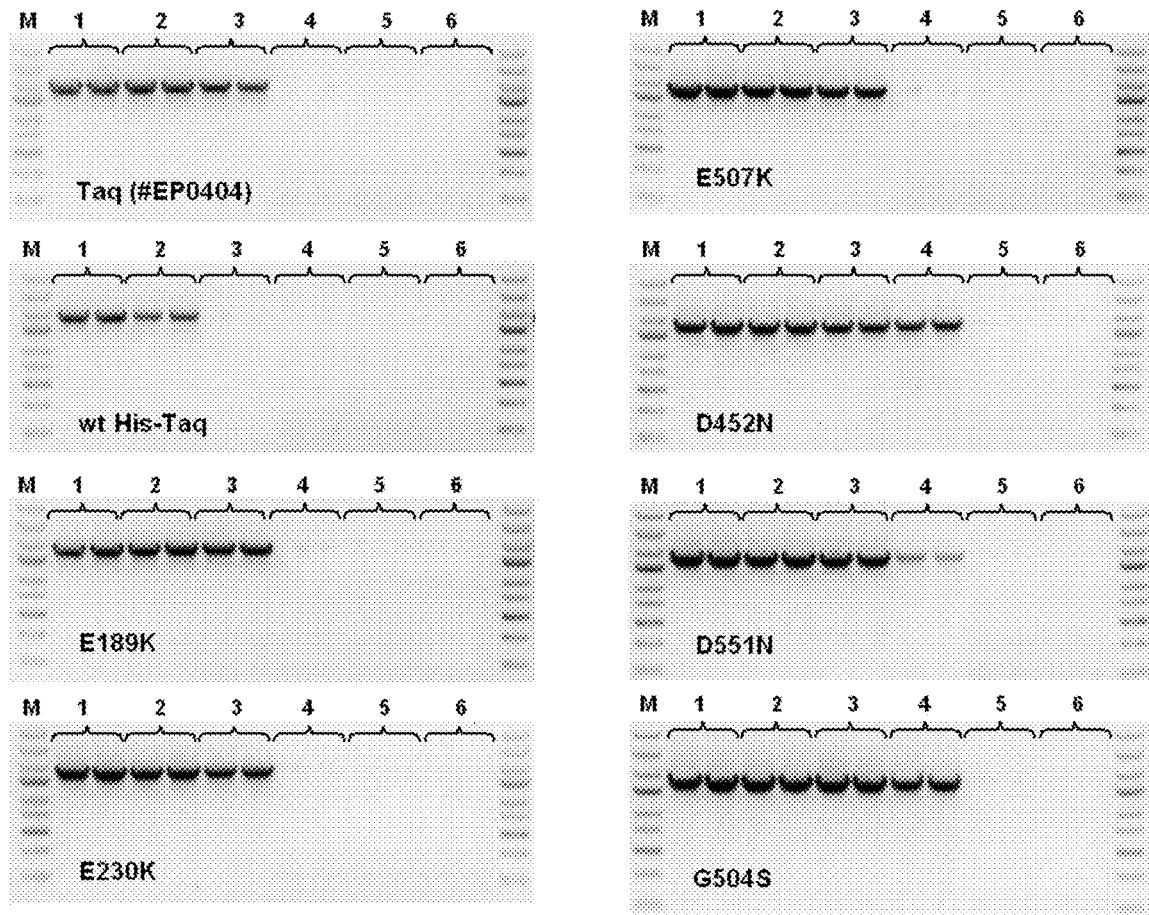

Fig. 19

DNA POLYMERASES

This application is a divisional of U.S. application Ser. No. 13/564,940, filed Aug. 2, 2012, now U.S. Pat. No. 9,493,848, which claims priority to Great Britain Patent Application No. 1113430.1, filed Aug. 3, 2011, each of which is incorporated by reference herein in its entirety for any purpose.

Applicants incorporate by reference the material contained in the accompanying computer readable Sequence Listing identified as 01129-0018-01US_SeqListing.txt, having a file creation date of Sep. 16, 2016, and a size of 16.4 KB.

FIELD OF INVENTION

The present invention relates to DNA polymerases, which possess increased resistance to PCR inhibitors, increased affinity to DNA substrate and increased DNA polymerization efficiency.

BACKGROUND OF THE INVENTION

Polymerase chain reaction (PCR) is probably the most popular application in contemporary molecular biology and diagnostics. The key components of PCR are thermostable DNA polymerases, which synthesize new DNA complementary to a DNA matrix. There are many different polymerases, which are used in PCR. Even though Taq DNA polymerase was the first enzyme employed in PCR and many new enzymes were discovered since that time, this polymerase continues to be the most popular and widely used in majority of PCR applications due to its robustness and efficiency as well as easy and cost efficient production process. Taq DNA polymerase has been studied very intensively and there is a lot of biochemical as well as structural data available on it. Within the course of these studies many different mutations of Taq DNA polymerase have been created and studied, which in one or another way improve properties of this enzyme. Some mutations are important for enzyme fidelity (U.S. Pat. Nos. 6,395,524, 6,602,695 and 5,614,365), some alter 5'-3' exonuclease activity (U.S. Pat. No. 5,466,591), change enzyme properties related to labeled nucleotide incorporation (Brandis et al., 1998), make the enzyme "cold sensitive" (Barnes and Kermekchiev, 2000) or increase polymerase resistance to different PCR inhibitors (Kermekchiev and Barnes, 2004; Kermekchiev and Kirilova, 2006). Such mutants of Taq DNA polymerase are useful in qPCR, DNA sequencing, amplification of DNA samples containing various PCR inhibitors (dye, blood, soil). For example, SYBR Green I intercalating dye is used in qPCR. This inhibits Taq DNA polymerase and can decrease PCR efficiency and sensitivity. Increased polymerase resistance to SYBR Green I may be associated with increased enzyme resistance to other PCR inhibitors from blood and soil (Kermekchiev et al, 2009; Zhang et al, 2010).

Mutation at various different amino acid positions in the Taq DNA polymerase are known to improve various different properties. These include K219, K225, E520, D578, A608 (Brandis et al., 1998; Holliger et al., 2001), S515 (Hardin et al., 2006), A521, V529, Q592 (Brandis et al., 1998) and S543 (Jestin et al., 2005; Vatta et al., 2005). In one example, the positively charged Taq DNA polymerase mutation E507K is known to improve the RNA target dependent activity by 50% compared to the parent enzyme.

Currently PCR represents one of the fastest growing segments of molecular biology applications market. New applications for PCR and new variants of PCR are being developed and introduced for research and diagnostic applications, such as fast qPCR, digital PCR and direct sample-to-PCR which require novel enzymatic properties. Therefore, there is a need in the industry for Taq DNA polymerase derivatives possessing novel, improved properties.

SUMMARY OF THE INVENTION

In a first aspect, the present invention provides a DNA polymerase mutant comprising a Taq DNA polymerase amino acid sequence with a mutation at one or more of the following selected amino acid positions: E189K, E230K, E507K, H28R, L30R, G38R, F73V, H75R, E76A, E76G, E76K, E90K, K206R, E315K, A348V, L351F, A439T, D452N, G504S, E507A, D551N, L552R, I553V, D578N, H676R, Q680R, D732G, E734G, E734K, F749V; wherein the polymerase mutant exhibits relative to wild-type DNA polymerase increased polymerase speed, increased affinity to DNA substrate and/or increased resistance to a DNA polymerase inhibitor; and wherein, when the mutation is E507K in combination with two or more further mutations or the mutation is Q680R in combination with four or more further mutations, at least one of the further mutations is at one of the selected amino acid positions; and when the mutation is I553V, this is not in combination with D551S.

Taq DNA polymerase mutants may be provided with increased resistance to SYBR Green I dye present in PCR mixture as well as mutants able to perform DNA amplification faster and/or more efficiently as compared to the wild type enzyme. One set of mutant variants of polymerase outperforms the wild type enzyme in PCR assays which contain SYBR Green I fluorescent dye in reaction mixture. Another set of mutants is useful in different PCR applications with shorter DNA elongation times as compared to the ones typically required for the wild type Taq DNA polymerase. A third set of mutants exhibit increased resistance to blood, SDS, GuHCl and heparin inhibition and may be used in direct DNA amplification from blood samples (at blood concentrations, which are inhibitory to wild type Taq DNA polymerase) or from unpurified/partially purified DNA samples in different lysis buffers.

The wild type Taq DNA polymerase amino acid sequence is shown in FIG. 1. The numbering system used in the present application is based on this sequence. A DNA polymerase mutant according to the present invention comprises the wild type sequence with a mutation at one of the indicated selected amino acid positions or at a plurality of the indicated selected amino acid positions. Where there is a mutation at one or more of the indicated selected amino acid positions it is also possible for there to be one or more further mutations at other positions in the wild type sequence. The number of these further mutations and the position of any such further mutation is such that the properties of increased polymerase speed, increased affinity to DNA substrate and increased resistance to a DNA polymerase inhibitor conferred by mutation at the indicated selected amino acid positions are not impaired. Such further mutations are preferably conservative mutations. In a preferred embodiment mutations of the wild type sequence occur only in the indicated selected amino acid positions. It is also possible for there to be additions to the amino acid sequence, for example at one or both ends of the sequence, without substantially affecting the activity of the polymerase.

Advantageously, the number of mutations at the one or more selected amino acid positions is limited, for example to no more than three of the selected amino acid positions. It has surprisingly been found that a relatively low number of mutations can give rise to advantageous properties of a mutant polymerase. In one arrangement, the amino acid sequence has a mutation at only one of the selected amino acid positions. In another arrangement, the amino acid sequence has a mutation at only two of the selected amino acid positions. By providing DNA polymerase mutants with a limited number of mutations in the primary structure it is thought that the tertiary, three dimensional structure of the polymerase is not altered significantly. Mutants according to the invention can exhibit relative to wild type DNA polymerase one or more of the advantageous properties of increased polymerase speed, increased affinity to DNA substrate and increased resistance to a DNA polymerase inhibitor.

In one aspect of the invention, the DNA polymerase mutant exhibits increased polymerase speed relative to wild type DNA polymerase. Such DNA polymerase mutants include those with a mutation at one or more of the following selected amino acid positions: E189K, E230K, E507K, H28R, L30R, F73V, H75R, E76A, E76G, E76K, E90K, K206R, A439T, D452N, G504S, D551N, I553V, H676R, D732G, E734G, F749V. It is preferred that the DNA polymerase mutant exhibits an increased polymerase speed which is at least 1.5 times faster than wild type DNA polymerase, preferably at least three times and more preferably at least 12 times faster. Polymerase speed may be measured by performing PCR on phage lambda DNA such as a 1825 bp fragment of phage lambda DNA. Alternatively, the polymerase speed may be measured by performing PCR on human genomic DNA such as, for example, on a 2.5 kbp fragment. The PCR buffer used for such assays may be based either on KCl or on ammonium sulfate. Quantitative analysis of PCR products may be performed using agarose gel electrophoresis, generally with 1% gels. Further details of typical measurements are presented in Example 2 below.

In a further aspect, the DNA polymerase mutant according to the invention exhibits increased affinity to DNA substrate, relative to wild type DNA polymerase. The DNA polymerase mutant preferably includes a mutation at one or more of the following selected amino acid positions: E189K, E230K, E507K, H75R, E315K, A348V, L351F, L552R, D578N. The DNA polymerase mutant may include double mutations wherein the selected amino acid positions are preferably selected from: H28R+E507K, H28R+Q680R, E507K+Q680R, L552R+Q680R, E230K+E507K, E189K+E507K, E315K+E507K, E230K+E315K, E507K+L552R.

Increased affinity to DNA substrate is generally expressed in terms of the dissociation constant Kd, which may typically be measured for a DNA oligoduplex substrate for example using an electrophoretic shift mobility assay following incubation in a suitable buffer such as 40 mM Tris, 20 mM acetic acid, 1 mM EDTA at pH8.4, in the presence of 10% v/v glycerol at 4° C. for 30 mins.

The Kd of wild type Taq DNA polymerase under these conditions is generally in the range 1.71 to 3.97 nM. Thus, a value of Kd below 1.71 nM denotes increased affinity to the DNA oligoduplex substrate relative to the wild type polymerase. It is preferred that the Kd for the mutant polymerase is no more than 1 nM and is typically in the range 0.14 to 1 nM.

In a further aspect, the DNA polymerase mutant according to the invention exhibits increased resistance to a DNA polymerase inhibitor. The DNA polymerase inhibitor may be selected from SYBR Green I dye, blood, SDS, guanadinium salts and heparin. Such DNA polymerase mutants preferably include a mutation at one or more of the following selected amino acid positions: E189K, E230K, E507K, H28R, L30R, G38R, H75R, E76A, E76G, E76K, E90K, E315K, A439T, D452N, G504S, E507A, D551N, L552R, I553V, D578N, H676R, Q680R, D732G, E734G, E734K. The DNA polymerase mutants may include a double mutation at the following selected amino acid positions: H28R+E507K, H28R+Q680R, E507K+Q680R, L552R+Q680R, E230K+E507K, E189K+E507K, E315K+E507K, E230K+E315K, E507K+L552R. Such DNA polymerase mutants may exhibit both increased resistance to a DNA polymerase inhibitor and exhibit an increased affinity to a DNA substrate relative to wild type DNA polymerase.

Preferably, the Kd of a DNA polymerase mutant exhibiting increased resistance to a DNA polymerase inhibitor for a DNA oligoduplex substrate is no more than 10 nM in the presence of SYBR Green I dye at a concentration of approximately 0.4 µM. This is typically measured as described above by electrophoretic shift mobility assay following incubation in a suitable buffer such as 40 mM Tris, 20 mM acetic acid, 1 mM EDTA at pH8.4, in the presence of 10% v/v glycerol at 4° C. for 30 mins.

In one preferred arrangement according to the invention the DNA polymerase mutant has mutations at one or more of the amino acid positions E189K, E230K and E507K. Mutations at two or three of these positions give rise to a DNA polymerase mutant which has both increased affinity to DNA substrate and increased resistance to SYBR Green I dye.

In a further aspect, the present invention provides a kit for nucleic acid amplification, such as PCR, which comprises a DNA polymerase mutant as described herein together with one or more reagents for a DNA synthesis reaction. Such reagents include appropriate buffers, primers and nucleotides suitable for the nucleic acid amplification reaction.

The invention further provides a process for the production of a DNA polymerase mutant as described herein. The process comprises:
 (1) subjecting a polynucleotide encoding a DNA polymerase to error-prone PCR to generate a mutant library comprising an array of differently-mutated polynucleotides;
 (2) screening the mutant library for increased polymerase speed, increased polymerase affinity to DNA substrate or increase resistance to a DNA polymerase inhibitor;
 (3) selecting one or more mutant DNA polymerases from screening step 2; and
 (4) repeating steps 1 to 3 until a final DNA polymerase mutant is obtained.

According to this process, the mutant library produced by error-prone PCR in step (1) comprises an array of polynucleotides at least some of which incorporate one or more mutations. On the basis that the mutations are generated in an essentially random way, some polynucleotides will encode DNA polymerases which are non-functional, some will encode DNA polymerases which have essentially normal function and others will encode DNA polymerases with properties which are either superior or inferior to the wild type DNA polymerase. Screening step (2) may typically be performed on one or more members of the library so as to identify the desired characteristics of polymerases encoded by the one or more members of the library. Following selection step (3) a polynucleotide encoding one or more selected DNA polymerases is subjected once again to error-prone PCR in accordance with step (1) and the process is repeated until such time as a suitable mutant polymerase is obtained through screening and selection. This process of directed evolution is described in further detail below.

DETAILED DESCRIPTION OF INVENTION

The invention will now be described in further detail, by way of example only, with reference to the accompanying drawings, in which:

FIG. 1 shows the amino acid sequence of wild type Taq DNA polymerase;

FIG. 3 shows the sequencing results of Taq DNA polymerase mutants selected after high throughput screening for SYBR Green I resistance;

FIGS. 4-1 to 4-3 show the frequency of mutations found during high throughput screening of Taq DNA polymerase for SYBR Green I resistance;

FIGS. 9-1 to 9-3 show the sequence of plasmid1 used as a PCR target for DNA amplification;

FIG. 10 shows the sequencing results of Taq DNA polymerase mutants selected after first high throughput screening of Taq DNA polymerase library for shorter amplification and annealing times;

FIGS. 11-1 to 11-4 show the frequency of mutations found during first high throughput screening of Taq DNA polymerase library for shorter amplification and annealing times;

FIG. 12 shows the sequencing results of Taq DNA polymerase mutants selected after the second high throughput screening of Taq DNA polymerase library for shorter amplification and annealing times;

FIGS. 13-1 to 13-5 show the frequency of mutations found during the second high throughput screening of Taq DNA polymerase library for shorter amplification and annealing times;

Figure 16:
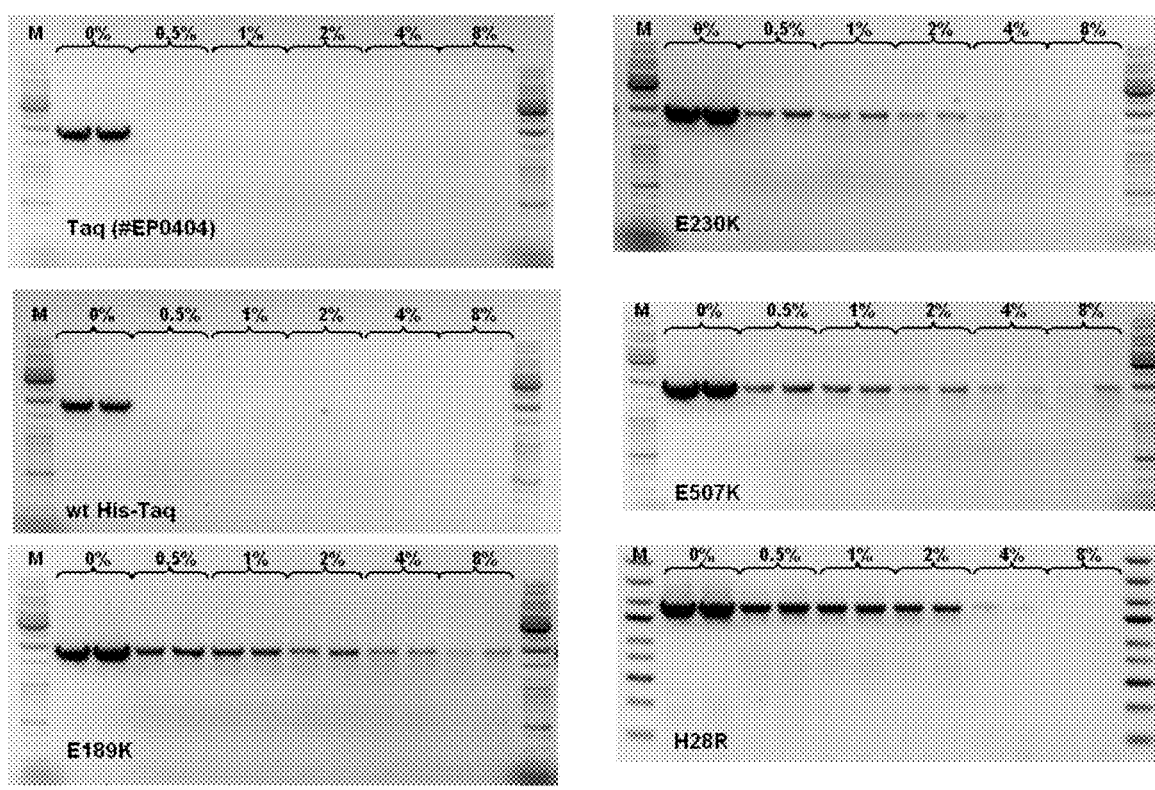
Figure 17:
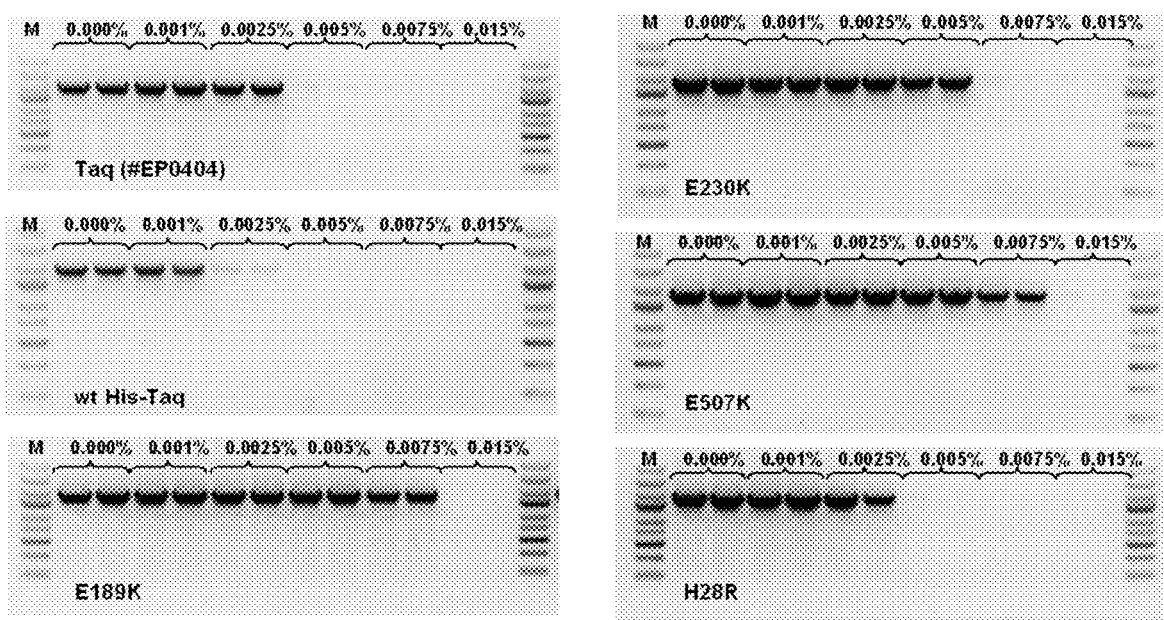
Figure 18:
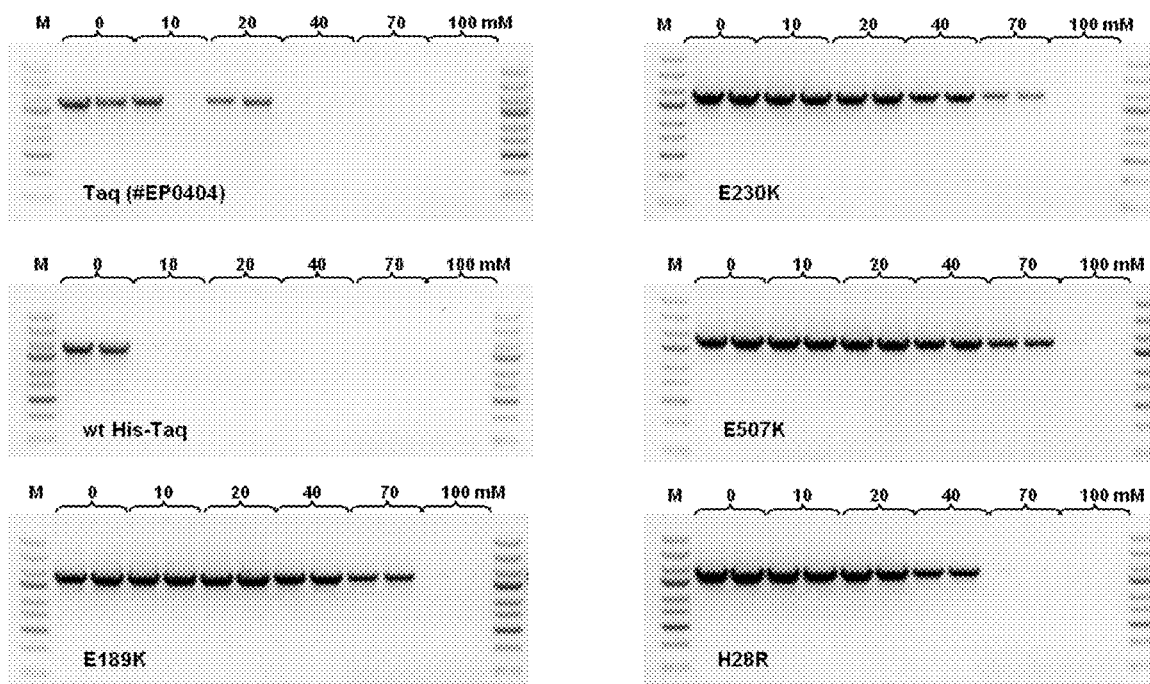

FIGS. 14A-B show the results of gel electrophoresis following PCR of a 1825 bp amplicon using various polymerases in the presence of ammonium sulfate or potassium chloride;

FIGS. 15A-B show the results of agarose gel electrophoresis following PCR on a 2.5 kbp amplicon with various polymerases in the presence of ammonium sulfate or potassium chloride;

FIG. 16 shows the results of gel electrophoresis following PCR of a 1.825 kbp amplicon in the presence of blood comparing commercial and wild type polymerase with polymerases according to the invention;

FIG. 17 shows the results of gel electrophoresis following PCR of a 1.825 kbp amplicon performed in the presence of SDS comparing commercial Taq polymerase and wild type Taq polymerase with polymerases according to the invention;

FIG. 18 shows the results of gel electrophoresis following PCR of a 1.825 kbp amplicon performed in the presence of guanidinium hydrochloride comparing commercial Taq polymerase and wild type Taq polymerase with polymerases according to the invention; and FIG. 19 shows the results of gel electrophoresis following PCR of a 1.825 kbp amplicon performed in the presence of heparin comparing commercial Taq polymerase and wild type Taq polymerase with polymerases according to the invention.

EXAMPLE 1

Mutant Taq DNA Polymerase Library Screening for Increased Resistance to SYBR Green I Dye Taq DNA polymerase is widely used in qPCR because it is a robust and efficient enzyme, which has 5'-3' exonuclease activity (required to activate Taqman probe), no 3'-5' exonuclease activity (no degradation of PCR primers) and is not sensitive to dUTP used to avoid contamination in qPCR master mixes. SYBR Green I intercalating dye used in qPCR inhibits Taq DNA polymerse (Nath et al., 2000) and can decrease PCR efficiency and sensitivity. In some cases problem can be solved by adjusting buffer composition, reaction conditions and/or using higher amounts of Taq DNA polymerase.

In order to select for Taq DNA polymerase mutants with increased resistance to SYBR Green I we have performed directed evolution of Taq DNA polymerase. The amino acids sequence of parental wild type Taq DNA polymerase used for mutagenesis is given in FIG. 1. The initial library of genes (L0) coding for mutant Taq DNA polymerases was generated by error-prone PCR using a modified protocol described by Zaccolo et al. (Zaccolo et al., 1996). Quality of the library was checked by sequencing of 8 randomly picked clones. One clone had deletion, which resulted in frameshift of coding sequence. Other 7 clones had from 2 to 6 nucleotide substitutions per gene. The ratio of transitions to transversions was 2.4:1. As a result mutant polymerases had from 1 to 5 amino acids changes or on the average 2.85 mutations per gene.

Figure 2:
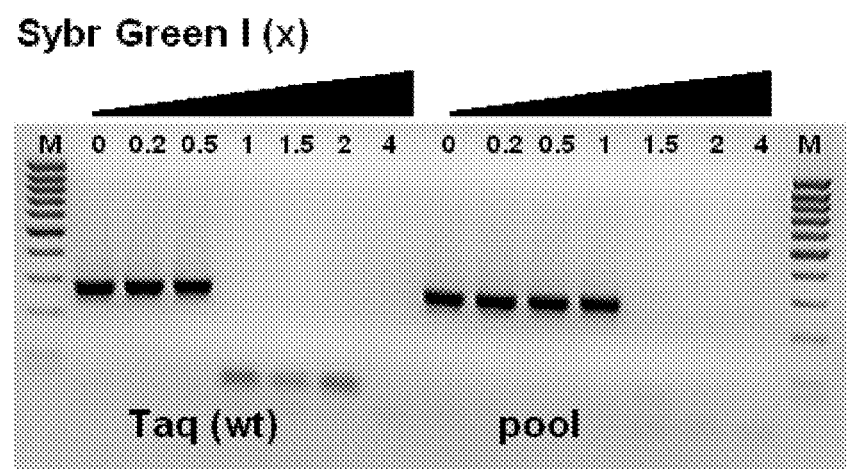
FIG. 2 shows the results of gel electrophoresis following PCR of a 250 bp amplicon performed with wild type polymerase and a pool of mutant polymerases at different SYBR Green I concentrations.

SYBR Green I dye 10,000× stock solution was obtained from Invitrogen and was used in our experiments. Several rounds of high-throughput screening were performed for the expressed polymerase ability to perform PCR at increasing concentrations of SYBR Green I (0.6×-2.5×). After the several screening rounds 37 random clones of individual mutants and the pool of all selected mutants were chosen for further investigation. Initially the pool of plasmids encoding selected polymerases was purified. Then the N-terminal (His)$_6$GlyAla tag was fused to PCR amplified Taq polymerase genes. Pool of mutant enzymes and wt Taq polymerase with the same affinity tag were expressed in *E. coli* cells and purified using Ni-NTA Superflow (Qiagen) chromatography. In order to check the efficiency of our screening we have tested wt Taq polymerase and pool of mutants for ability to perform PCR at different SYBR Green I concentrations (FIG. 2). In our particular (target/primer/buffer) amplification system Taq DNA polymerase typically can synthesize 250 bp PCR fragment in the presence of 0.2-0.5× SYBR Green I dye. Meanwhile the pool of mutant Taq DNA polymerases can generate the same 250 bp PCR fragment in the presence of at least 2 times higher concentration (1×) of SYBR Green I dye (FIG. 2). The PCR of 250 bp amplicon performed with wt His-Taq polymerase and pool of mutant polymerases at different SYBR Green I concentrations (SYBR Green I stock concentration is 10,000× and amplification was performed using 0.2-4× concentration of dye). It is evident that in case of enzyme pool resistance to SYBR Green I inhibition is an average value and some of the individual enzymes from the pool should have higher resistances, and some lower than the average resistance of the pool of polymerases. Different properties of selected mutant enzymes are determined by various mutations accumulated during the mutagenesis/screening procedure. Some mutations should be beneficial, some can be supplementary, neutral or even negative. Therefore it is critical to understand the nature of selected mutants and elucidate individual properties of single amino acids changes. As a consequence 37 random clones of individual positive hits were sequenced and analized (FIG. 3). Two clones (L6M1_1, L6M4_1) had stop codons and were excluded from further analyzis. The number of amino acid changes in selected mutants varies from 1 to 8. On average there are 3.6 amino acids changes per gene. The frequency of all found mutations was calculated and is given in FIG. 4. The most often mutated position in our selection was glutamate 507 (E507K—11 mutants; E507A—3). There are 4 selected clones, which contain only single mutation of E507 amino acid (L6M8_1—E507A; L6M40_1, Taq_B3, Taq_A4—E507K) (FIG. 1). Other most frequently mutated positions are H28 (H28R—6); F27 (F27L—3; F27S—1); K219 (K219R—4); E230 (E230K—3; E230G—1); E76 (E76G—3) and E189 (E189K—3).

The general assumption is that most frequently mutated amino acids are the most important and have the biggest impact on Taq DNA polymerase resistance to SYBR Green I inhibition. In order to elucidate individual properties of different mutations single and multiple mutants of Taq polymerase were constructed (with addition of N-terminal $(His)_6GlyAla$ tag for purification), expressed, partially purified and analyzed. The wt and mutant Taq DNA polymerases were purified using two step procedure: initial denaturation of E. coli proteins for 15 minutes at 75° C. and subsequent Ni-NTA affinity chromatography. As a result Taq DNA polymerase variants were typically purified to ~80% homogeneity according to SDS-PAGE densitometry analysis. The activities of purified polymerases were evaluated using standard polymerase unit definition assay and if necessary (for example in PCR applications) equal amounts of polymerase units were used for analysis.

Figure 5:
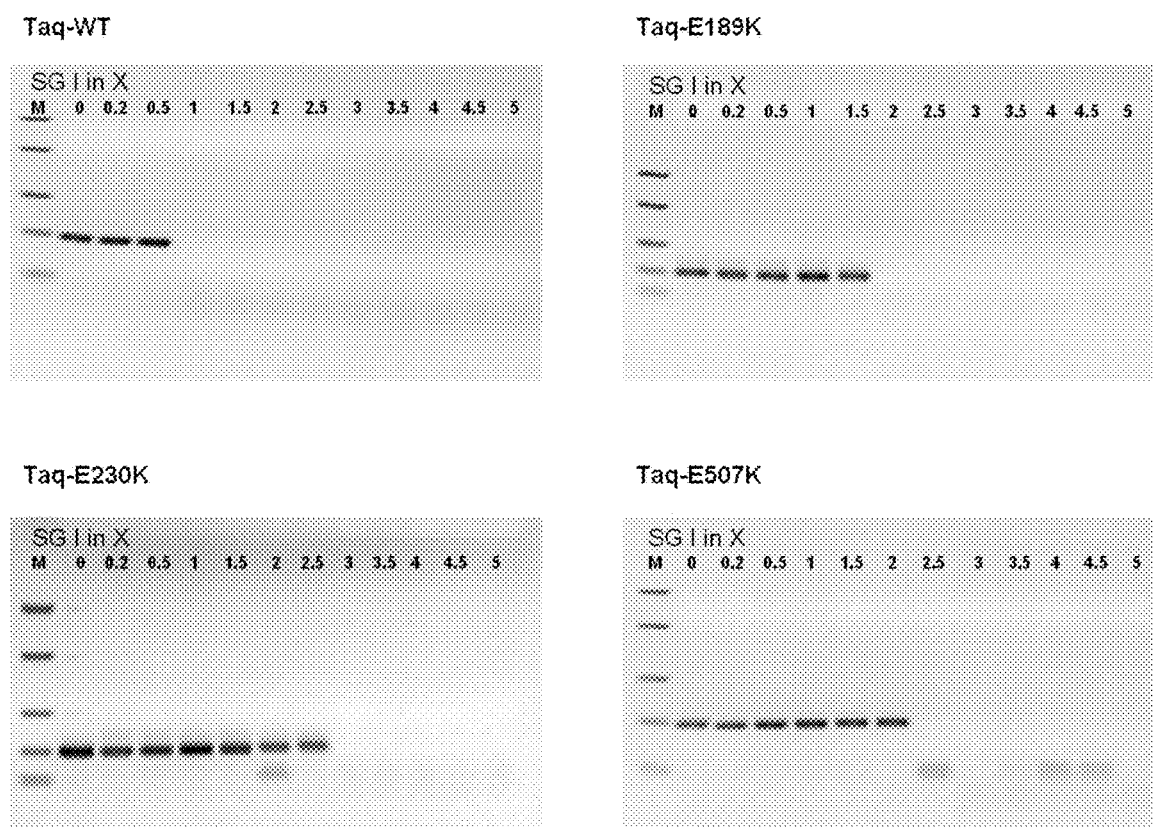
FIG. 5 shows the results of gel electrophoresis following PCR of a 200 bp amplicon comparing wild type polymerase with polymerases of the invention.
Figure 6:
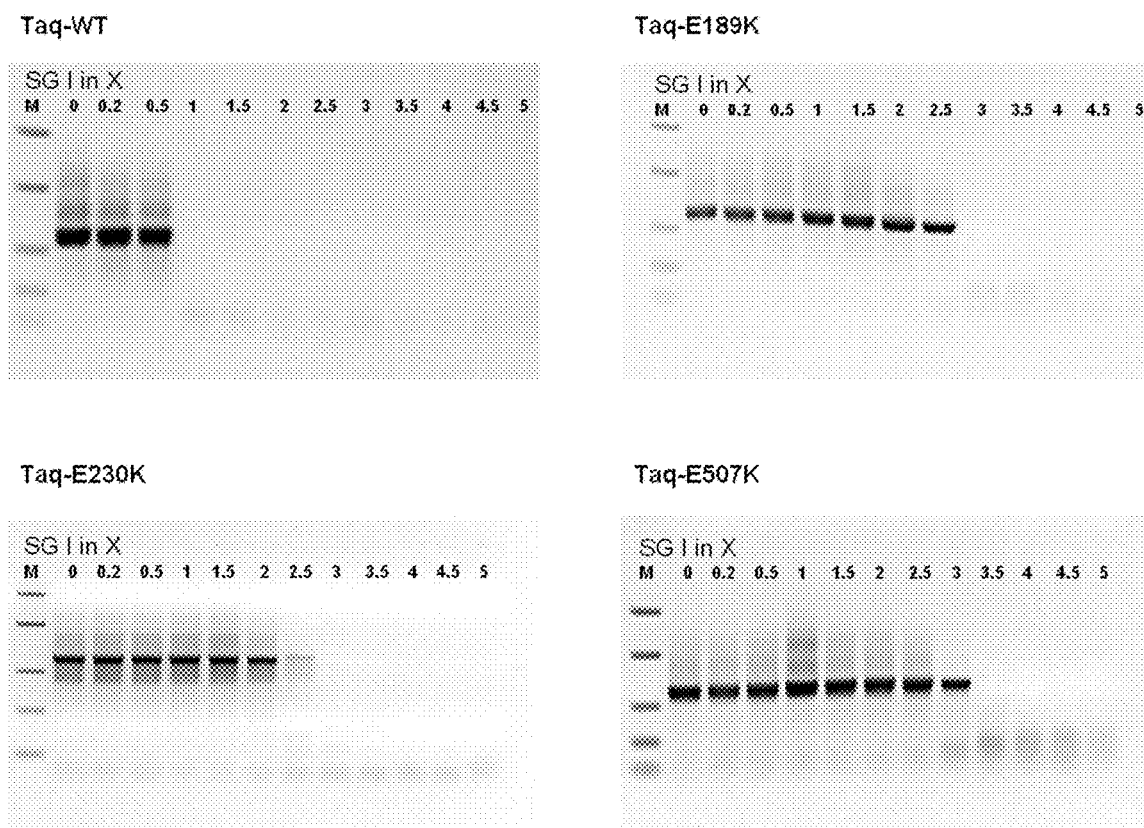
FIG. 6 shows the results of gel electrophoresis following PCR of a 500 bp amplicon at different SYBR Green I concentrations using wild type enzymes or enzymes according to the invention.

The ability of wt and individual mutants of Taq polymerase to perform PCR at different SYBR Green I concentrations was tested using many different target/primer/buffer systems. In this example we present two PCR performed either on plasmid DNA (~200 bp fragment) or on human genomic DNA (~500 bp fragment). Amplification is performed in the presence of 0.2-5× concentration of SYBR Green I dye. The threshold concentration of SYBR Green I dye (at which full length DNA fragment is still synthesized) is determined and is used to characterize enzyme of interest resistance to SYBR Green. The precise threshold value depends on particular target/primer/buffer system used for PCR, therefore it is very important to have wt Taq DNA polymerase control reactions performed in parallel. Agarose gel electrophoresis pictures of typical experiment are shown in FIGS. 5 and 6. In both cases (amplification of 200 bp and 500 bp DNA fragments) wt Taq DNA polymerase can synthesize PCR product at 0.5× concentration of SYBR Green I dye in reaction mixture. In FIG. 5, The PCR of 200 bp amplicon from plasmid DNA performed with wt His-Taq polymerase and single amino acid mutant polymerases at different SYBR Green I concentrations (SYBR Green I stock concentration is 10,000× and amplification was performed using 0.2-5× concentration of dye). In FIG. 6, The PCR of 500 bp amplicon from human genomic DNA performed with wt His-Taq polymerase and single amino acid mutant polymerases at different SYBR Green I concentrations (SYBR Green I stock concentration is 10,000× and amplification was performed using 0.2-5× concentration of dye). Meanwhile Taq DNA polymerase mutants tolerate substantially higher concentrations of SYBR Green I dye in reaction mixture (E189K—1.5× (200 bp) and 2.5× (500 bp); E230K—2.5× (200 bp) and 2× (500 bp); E507K—2× (200 bp) and 3× (500 bp)). Summarized data of SYBR Green I dye inhibition in PCR experiments are presented in Table 1. Performed PCR inhibition experiments allowed us to identify many individual mutations, which increase Taq DNA polymerase resistance to SYBR Green I dye and may be used in production of commercial enzymes and kits. Different mutants increase Taq polymerase resistance from 2 to 10 times (1-5× concentration of SYBRGreen I). Enzyme resistance to SYBR Green I dye is additive (cumulative) and in most cases can be increased constructing double or triple mutants. For example, mutant E230K can tolerate 2-2.5× and E507K—2-3× concentration of SYBR Green I. Subsequently double mutant E230K+E507K can tolerate 3-4.5× and triple mutant E230K+E507K+E189K—3.5-5× concentration of SYBR Green I (Table 1). Many more multiple mutant combinations were tested and found to have increased SYBR Green I resistance comparing to single mutants (Table 1). Additivity of SYBR Green resistance is very important feature, which enables design of mutant polymerases with individual properties according to specific application requirements.

Figure 7:
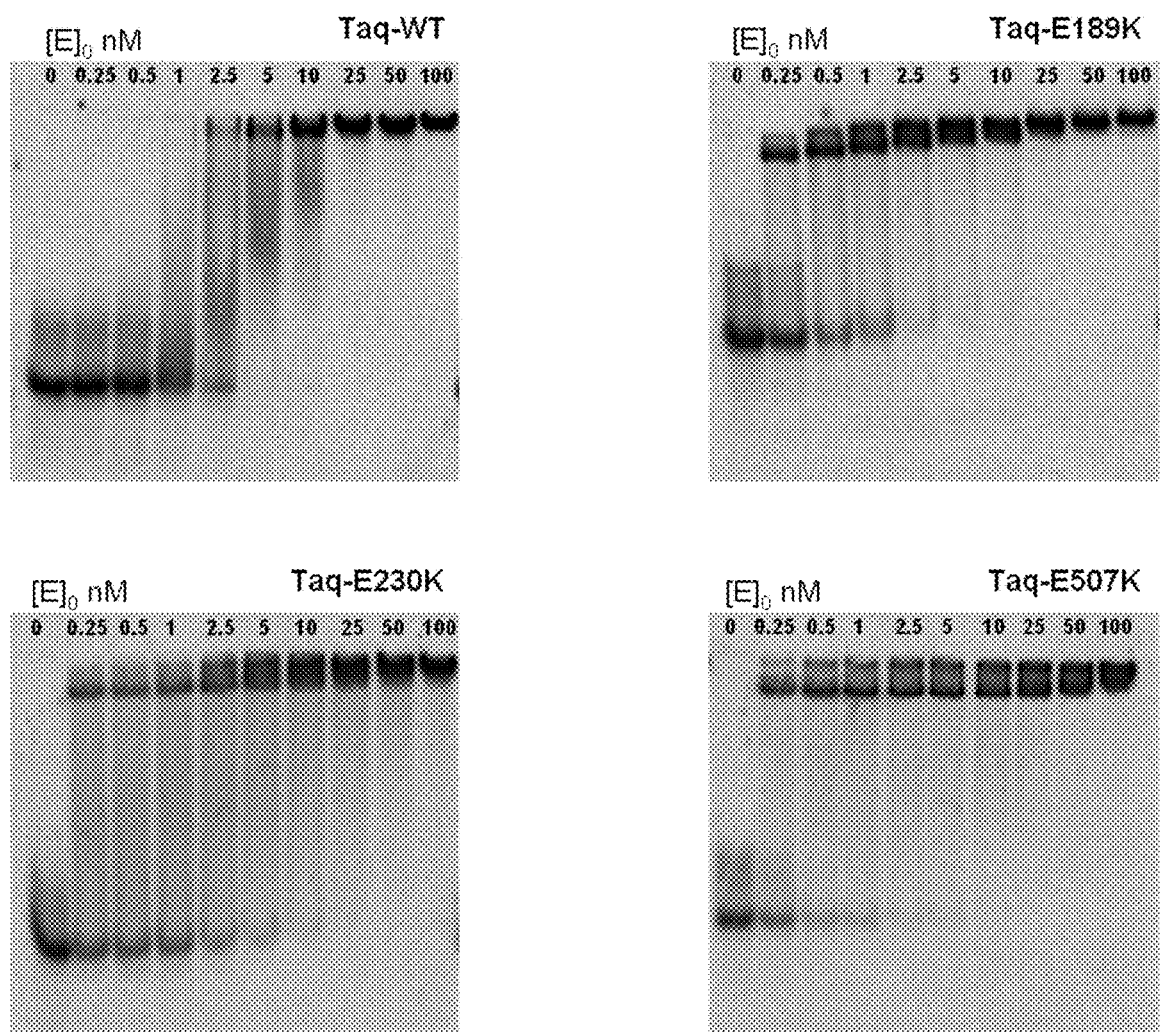
FIG. 7 shows the results of polyacrylamide gel electrophoresis in an electrophoretic mobility shift assay for wild type polymerase and polymerases according to the invention.
Figure 8:
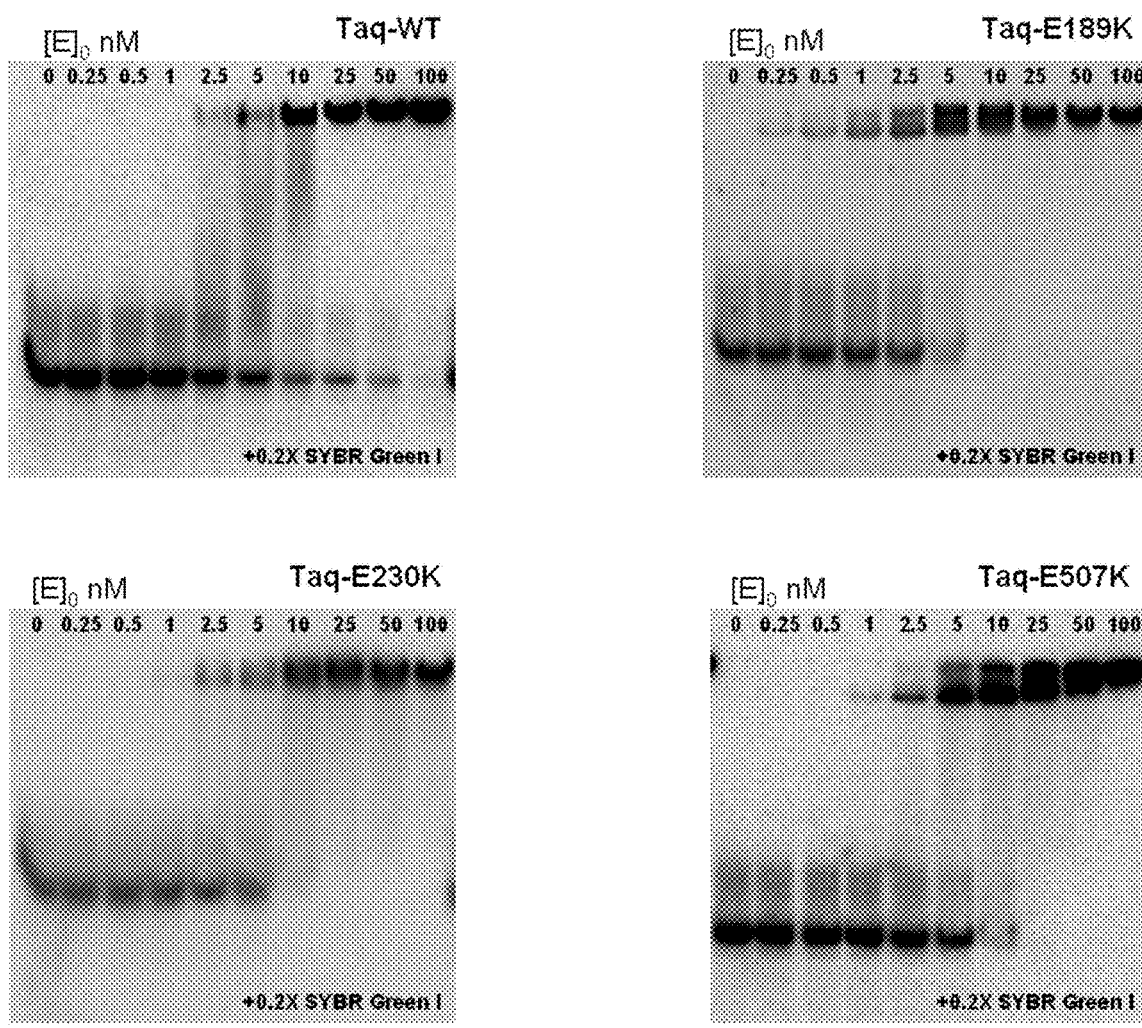
FIG. 8 shows the results of polyacrylamide gel electrophoresis in an electrophoretic mobility shift assay for wild type polymerase and polymerases according to the invention in the presence of SYBR Green I dye.

Bioinformatic analysis of selected Taq DNA polymerase mutants with increased resistance to SYBR Green I dye revealed that in most cases changes were associated with amino acids which eliminate negative charge (E76G, E507A, D578N, D732G), add positive charge (H28R, G38R, L552R, H676R, Q680R) or change negative charge to positive one (E90K, E189K, E230K, E315K, E507K). In all cases mutant polymerases acquired higher total positive charge and either could less interact with positively charged SYBR Green I dye or should have increased affinity to negatively charged substrate (DNA). In both cases such enzymes should become more resistant to SYBR Green I inhibition during PCR. If this hypothesis is correct, then mutations scope could be broadened by using similar substitutions and constructing mutants with increased positive charge (amino acids change X=>K, R) or decreased negative charge network (amino acids change D, E=>X). In order to test the polymerase affinity to DNA we have measured dissociation constant (Kd) value of protein-DNA interaction using electrophoretic mobility shift assay (EMSA). Wild type Taq DNA polymerase and mutants Kd were measured directly (without SYBR Green I) and with SYBR Green I. Polyacrylamid gel electrophoresis pictures of typical experiment are shown in FIGS. 7 and 8. In FIG. 7, Polyacrylamid gel electrophoresis pictures of electrophoretic mobility shift assay (EMSA). Polymerase affinity to substrate (Kd) was measured using radioactively labeled DNA substrate at 0.1 nM concentration and 0.25-100 nM protein concentration gradient. In FIG. 8, Polyacrylamid gel electrophoresis pictures of electrophoretic mobility shift assay (EMSA). Polymerase affinity to substrate (Kd) in the presence of 0.2× SYBR Green I dye was measured using radioactively labeled DNA substrate at 0.1 nM concentration and 0.25-100 nM protein concentration gradient. Calculated Kd values for wt Taq DNA polymerase and different mutant variants are summarized in the Table 2. The Kd of wt Taq DNA polymerase and DNA oligoduplex complex was obtained to be in the range of 1.71-3.97 nM without SYBR Green I dye and in the range of 6.17-9.39 nM with SYBR Green I (0.2×). Meanwhile most mutant variants have Kd below 1.0 nM without SYBR Green I (E189K, E230K, E315K, E507K, L552R, D578N, H28R+E507K, H28R+Q680R, E507K+ Q680R, L552R+Q680R, E230K+E507K, E189K+E507K, E315K+E507K, E230K+E315K, E507K+L552R, E189K+ E230K+E507K) and <10 nM Kd in the presence of SYBR Green I. It is also important to stress that EMSA measurements performed at 0.1 nM concentration of oligoduplex are good to calculate Kd values above 1 nM and give only approximate results for Kd values below 1 nM. Consequently Kd values determined for mutant Taq DNA polymerases to be in the range of 0.14-1 nM can be much lower. Overall data confirm the statement, that mutations of interest, which were identified, possess 5-10 times increased affinity to DNA substrate (E189K, E230K, E315K, E507K, L552R, D578N, H28R+E507K, L552R+Q680R, E230K+ E507K, E189K+E507K, E315K+E507K, E230K+E315K, E507K+L552R, E189K+E230K+E507K). It is very likely, that SYBR Green I, present in PCR, binds to DNA target, hinders polymerase binding to substrate and in such a way decreases the efficiency of PCR. Consequently mutant polymerases with increased affinity are more resistant to SYBR Green I inhibition. The Kd of some mutant polymerases (E189K, E230K, E315K, E507K, L552R, D578N, H28R+ E507K, H28R+Q680R, E507K+Q680R, L552R+Q680R, E315K+E507K, E230K+E315K, E507K+L552R, E189K+ E230K+E507K) in the presence of SYBR Green I (0.2×) is increased to the level of wt Taq DNA polymerase Kd without SYBR Green I and is below 5 nM (Table 2). Diminished Kd of mutant polymerases and DNA/DNA substrate complex confirms the hypothesis, that positive charges (accumulated during the screening of Taq DNA polymerase for SYBR Green I dye resistance) increase the affinity of enzyme to negatively charged DNA and in such a way neutralize the inhibitory effect of positively charged SYBR Green I dye. Taq DNA polymerases with increased affinity could be very useful in many different PCR and qPCR applications since in some cases increased affinity can lead to increased enzyme processivity, polymerization velocity, resistance to different inhibitors, more sensitive PCR, etc.

Methods and Materials

Polymerase Purification

The expression plasmid coding for the mutant or wt Taq DNA polymerase variants fused to the N-terminal (His)$_6$GlyAla tag was expressed in E. coli cells. The E. coli cells were harvested by centrifugation at 4° C. (5000 rpm for 10 min, Beckman J2-21 centrifuge, JA-10 rotor) and resuspended in buffer A (50 mM NaH$_2$PO$_4$, 300 mM NaCl, 10 mM imidazole and 10 mM 2-mercaptoethanol, pH 8.0) with 1 mM phenylmethanesulphonyl-fluoride (Sigma). After sonication on ice (7.5 min), samples were centrifugated at 16 170 g for 20 min (Eppendorf 5417R). Next, the supernatant was heated at 75° C. for 15 min to denature most of the E. coli mezofilic proteins.

Precipitated proteins were removed by centrifugation (at 16 170 g for 20 min) and the supernatant was loaded onto a Ni-NTA Superflow (Qiagen) minicolumn. To remove unspecifically bound proteins, the minicolumn was washed with buffer B (50 mM NaH$_2$PO$_4$, 300 mM NaCl, 20 mM imidazole, 10 mM 2-mercaptoethanol and 0.1% Triton X-100, pH 8.0); the polymerase was eluted with buffer C (50 mM NaH$_2$PO$_4$, 300 mM NaCl, 250 mM imidazole, 10 mM 2-mercaptoethanol and 0.1% Triton X-100, pH 8.0). Polymerase was dialysed against storage buffer (20 mM Tris-HCl (pH 8.0), 1 mM DTT, 0.1 mM EDTA, 100 mM KCl, 0.5% (v/v) Nonidet P40, 0.5% (v/v) Tween 20 and 50% (v/v) glycerol) and stored at −20° C.

Polymerase Unit Definition Assay

The DNA polymerase activity of purified mutant Taq DNA polymerases was measured according to the following protocol. The enzyme was incubated in a reaction mixture (50 µl) consisting of 67 mM Tris-HCl (pH 8.8), 6.7 mM MgCl$_2$, 50 mM NaCl, 1 mM DTT, 0.1 mg/ml BSA, 200 µM of each of dATP, dCTP, dTTP and dGTP, 0.4 MBq/ml of [methyl-$^3$H]thymidine 5'-triphosphate (Amersham), and 250 µg/ml of activated salmon sperm DNA at 70° C. for 30 min. The reaction was stopped on ice, and an aliquot was spotted onto a DE-81 filter-paper disc. The disc was dried on a heat block, washed in 7.5% sodium phosphate buffer for 5 minutes 3 times and once in 70% ethanol for 2 minutes, and then dried again. The incorporated radioactivity on the dried filter-paper disc was counted using a Beckman LS-1801 scintillation counter. One unit of Taq DNA polymerase catalyzes the incorporation of 10 nmol of deoxyribonucleotides into a polynucleotide fraction (adsorbed on DE-81) in 30 min at 70° C.

Mutagenic PCR

Mutant Taq DNA polymerase gene variants were constructed using modified error-prone PCR protocol described by Zaccolo (Zaccolo et al., 1996). Briefly, a PCR comprising 75 mM Tris-HCl (pH 8.8 at 25° C.), 20 mM (NH$_4$)$_2$SO$_4$, 0.01% (v/v) Tween 20, 10 ng template DNA forward and reverse primers (0.5 µM each), dNTPs (200 µM each), 0.4 µM dPTP (TriLink BioTechnologies), 10 µM 8-oxo-dGTP (TriLink BioTechnologies), 1.5 mM MgCl$_2$ and 9.75 u of Taq polymerase in a total volume of 390 µL was carried out with the thermal profile 2 min at 94° C. followed by 30 cycles of 30 s 94° C., 30 s 50° C., 2 min 40 s 72° C. and finished with 10 min at 72° C. Amplified PCR product was digested with appropriate restriction endonucleases and cloned into an expression vector using T4 DNA ligase.

Mutant Taq DNA Polymerases are More Tolerant to SYBR Green I Dye in PCR

10000×SYBR Green I dye solution was obtained from Invitrogen (S7567) and stored in small aliquots at −20° C. Fresh serial dilutions (in nuclease-free water) of SYBR Green I dye stock solution were used in PCR. A typical SYBR Green I dye solution at a dilution of 0.2× is estimated to have a concentration of 0.4 µM (Gudnason et al 2007, Zipper et al 2004).

Amplification of 250 bp Bacterial Plasmid DNA Target with Pool of Mutant Taq Polymerases PCR mixtures comprising 10 mM Tris-HCl (pH 8.8), 50 mM KCl, 0.08% (v/v) Nonidet P40, dNTPs (200 µM each), 1.5 mM MgCl$_2$, 0.5 µM each of primer 1 and 2 (Table 3), 6 ng plasmid1 DNA (FIG. 9), 0.5 u of polymerase and various amounts of SYBR Green I dye (at the final concentration of 0, 0.2, 0.5, 1, 1.5, 2, 4×) in a total volume of 20 µL were subjected to the following thermocycling conditions: 2 min at 94° C. followed by 30 cycles of 30 s 94° C., 30 s 50° C., 20 s 72° C. PCR products were analyzed in 2% agarose gel electrophoresis.

Amplification of 200 bp Bacterial Plasmid DNA Target with Mutant Taq Polymerases PCR mixtures comprising 10 mM Tris-HCl (pH 8.8), 50 mM KCl, 0.08% (v/v) Nonidet P40, dNTPs (200 µM each), 1.5 mM MgCl$_2$, 0.5 µM each of primer 3 and 4 (Table 3), 6 ng plasmid1 DNA (FIG. 9), 0.5 u of polymerase and various amounts of SYBR Green I dye (at the final concentration of 0, 0.2, 0.5, 1, 1.5, 2, 2.5, 3, 3.5, 4, 4.5 or 5×) in a total volume of 20 µL were subjected to the following thermocycling conditions: 3 min at 94° C. followed by 30 cycles of 30 s 94° C., 30 s 50° C., 15 s 72° C. PCR products were analyzed in 1-2% agarose gel electrophoresis.

Amplification of 500 bp Human Genomic DNA Target with Mutant Taq Polymerases

PCR mixtures (20 µL) containing: 10 mM Tris-HCl (pH 8.8), 50 mM KCl, 0.08% (v/v) Nonidet P40, dNTPs (200 µM each), 1.5 mM $MgCl_2$, 0.5 µM each of primer 5 and 6 (Table 3), 40 ng of human genomic DNA, 0.5 u of polymerase and various amounts of SYBR Green I dye (at the final concentration of 0, 0.2, 0.5, 1, 1.5, 2, 2.5, 3, 3.5, 4, 4.5 or 5×) were subjected to the following thermocycling conditions: 3 min at 95° C. followed by 35 cycles of 30 s 95° C., 30 s 60° C., 30 s 72° C. PCR products were analyzed in 1% agarose gel electrophoresis.

Increased Affinity of Mutant Taq DNA Polymerases for Primer-Template DNA

Preparation of Radioactively Labeled Probe for Electrophoretic Mobility Shift Assay Radioactively labeled probe for electrophoretic mobility shift assay was prepared as follows. A single-stranded 24-mer oligonucleotide 1 was radioactively labeled at 5'-termini with polynucleotide kinase (PNK). Briefly, reaction mixture containing 1×PNK buffer A (50 mM Tris-HCl (pH 7.6), 10 mM $MgCl_2$, 5 mM DTT, 0.1 mM spermidine), 1 µM oligonucletide 1, 1 µM [$\gamma$-$^{33}$P]-ATP (Hartmann Analytic) and 0.5 u/µl PNK was incubated at 37° C. for 30 min, then PNK was inactivated by heating the sample at 70° C. for 10 min. A dsDNA probe for electrophoretic mobility shift assays was prepared by annealing radioactively labeled oligonucleotide 1 to a single-stranded 44-mer oligonucleotide 2 as follows. A mixture consisting of 75 mM Tris-HCl (pH 8.8), 20 mM $(NH_4)_2SO_4$, 0.01% (v/v) Tween 20, 2 mM $MgCl_2$, 20 nM of unpurified radioactively labeled oligonucleotide 1 and 25 nM of oligonucleotide 2 was incubated at 94° C. for 4 min, then the sample was transferred to the glass with pre-boiled water and left to cool slowly overnight.

Electrophoretic Mobility Shift Assay

Serial dilutions of mutant Taq polymerase were prepared in polymerase storage buffer: 20 mM Tris-HCl (pH 8.0), 1 mM DTT, 0.1 mM EDTA, 100 mM KCl, 0.5% (v/v) Nonidet P40, 0.5% (v/v) Tween 20 and 50% (v/v) glycerol. Mutant Taq polymerase at various concentrations (0.25, 0.5, 1, 2.5, 5, 10, 25, 50, and 100 nM) was incubated with 0.1 nM radioactively labeled dsDNA probe (see above) in 1×TAE buffer (40 mM Tris, 20 mM acetic acid, 1 mM EDTA, pH 8.4) with 10% (vol/vol) glycerol and without or with Sybr Green I dye (0.2× final concentration) at +4° C. for 30 min. 5 µl of samples were run on a native 12% polyacrylamide gel to separate the protein-DNA complex from the free DNA. Gels were dried and exposed to storage phosphor screens (FujiFilm). Screens were scanned with phosphorimager scanner (Typhoon) at resolution 100. The concentration of polymerase-DNA complex was determined from scanned gels using TotalLab100; the dissociation constant of polymerase-DNA complex Ka (nM) was calculated with GraphPad using the following equation:

$$[ES]=([E]_0+[S]_0+K_d-\text{sqrt}(sqr([E]_0+[S]_0+Ka)-4[S]_0[E]_0))/2,$$

where [ES] is the concentration of formed polymerase-DNA complex (nM), $[E]_0$ is the initial concentration of polymerase (nM), $[S]_0$—the initial concentration of DNA substrate (0.1 nM).

EXAMPLE 2

Mutant Taq DNA Polymerase Library Screening for Increased Amplification Speed

PCR and qPCR applications are widely used in almost all molecular biology, biochemistry and clinical diagnostic laboratories over the world. Faster PCR applications are highly desirable due to the fact that they decrease time spent for DNA amplification, required machine working time and increase the efficiency of analytical procedure. Fast PCR machines are already available on the market and now the limiting step is the enzyme suitable for fast applications. Taq DNA polymerase, which is widely used in PCR and qPCR, was subjected to in vitro evolution aiming to increase its amplification speed and decrease time required for elongation step during PCR. Two different libraries of Taq DNA polymerase were used for high-throughput screening in this example.

$1^{st}$ Screening

The same mutant Taq DNA polymerase library (L0) as in Example 1 was used for selection of improved Taq DNA polymerase variants. Several rounds of high-throughput screening were performed testing expressed polymerase ability to perform PCR using shorter and shorter amplification and annealing times with every screening round. Subsequently 43 random clones of individual mutants were sequenced and analized (FIG. 10). Two clones (L8-10, L8-42) had stop codons and were excluded from further analyzis. The number of amino acid changes in selected mutants varies from 2 to 12. On average there are 5.4 amino acids changes per gene. The frequency of all identified mutations was calculated and is given in FIG. 11. The most often mutated positions in this selection were glutamate 230 (E230K—33 mutants), leucine 30 (L30P—21 mutants; L30R—10; L30Q—1), aspartate 452 (D452N—18 mutants), glycine 504 (G504S—15 mutants), leucine 311 (L311F—4 mutants; L311R—1), glutamate 507 (E507A—3 mutants; E507G—2), glutamate 189 (E189K—4 mutants). There are 2 identical selected clones (L8-9, L8-39), which specifically contain only 4 most frequent mutations (L30P, E230K, D452N, G504S).

$2^{nd}$ Screening

An additional screening of Taq DNA polymerase for mutant variants able to perform PCR at shorter amplification and annealing times was performed using library (L3) with increased mutational load. The L3 library was also generated by error-prone PCR using a modified protocol described by Zaccolo et al. (Zaccolo et al., 1996). Quality of the library was checked by sequencing of 9 randomly picked clones. Two clones had deletions, which resulted in frameshift of coding sequence. Other 7 clones had from 2 to 9 nucleotide substitutions per gene. The ratio of transitions to transversions was 6:1. As a result mutant polymerases had from 1 to 5 amino acids changes or on the average 3 mutations per gene. Several rounds of high-throughput screening were performed testing expressed polymerase ability to perform PCR using shorter and shorter amplification and annealing times with every screening round. Subsequently 42 random clones of individual mutants after the screening were sequenced. Two clones had deletions/insertions, three clones had truncated N terminus and were omitted from analyzis (FIG. 12). The number of amino acid changes in selected mutants varies from 2 to 10. On average there are 5.4 amino acids changes per gene. The frequency of all found mutations was calculated and is given in FIG. 13. The most often mutated positions in this selection were phenylalanine 73 (F73V—3 mutants; F73S—1; F73L—1), aspartate 144 (D144G—4 mutants; D144N—1), lysine 206 (K206R—5 mutants), leucine 30 (L30P—3 mutants), histidine 75 (H75R—3 mutants), glutamate 90 (E90G—3 mutants), lysine 143 (K143E—2 mutants; K143R—1), leucine 351 (L351F—3 mutants), glutamate 397 (E397K—2 mutants; E397G—1), alanine 439 (A439T—3 mutants).

Mutant Analysis

The general assumption is that most frequently mutated amino acids found during the screening are the most important and have the biggest impact on Taq DNA polymerase properties. Site specific mutagenesis was used to construct novel polymerase mutants, by introducing mutation most oftenly found in our selective enrichment procedure and which were not described elsewhere in the literature. In order to elucidate individual properties of different mutations single mutants of Taq polymerase were constructed (with addition of N-terminal $(His)_6GlyAla$ tag for purification), expressed, partially purified and analyzed. The wt and mutant Taq DNA polymerases were purified using two step procedure: initial denaturation of *E. coli* proteins for 15 minutes at 75° C. and subsequent Ni-NTA affinity chromatography. As a result Taq DNA polymerase variants were typically purified to ~80% homogeneity according to SDS-PAGE densitometry analysis. The activities of purified polymerases were evaluated using standard polymerase unit definition assay and, if necessary (for example in PCR applications), equal amounts of polymerase units were used for analysis. The ability of wt and individual mutants of Taq polymerase to perform PCR using shorter amplification and annealing times was tested using few different target/primer/buffer systems. Four PCR were performed either on phage lambda DNA (1825 bp fragment) or on human genomic DNA (~2.5 kbp fragment) using PCR buffer based either on KCl or on $(NH_4)_2SO_4$ (see methods and materials). Amplification was performed using three different in length (Normal, Fast, Very fast) cycling conditions. In all cases wt Taq DNA polymerase with His tag purified in similar way was used as a control. Agarose gel electrophoresis pictures of typical experiment are shown in FIGS. 14 and 15. Phage lambda DNA amplification (1825 bp fragment) was performed using ~30 s/kb (normal), ~10 s/kb (fast) and 2.5 s/kb (very fast) extension rates. Recommended extension rate for Taq DNA polymerase is 30-60 s/kb. In this test PCR wt Taq DNA polymerase used as a control was able to amplify 1825 bp DNA fragment only under normal (~30 s/kb) cycling conditions (FIG. 14). Mutant enzymes (point mutants) identified in our screening were able to amplify target under fast ~10 s/kb (L30R; E230K; D452N; G504S; E507K; E189K) and even very fast ~2.5 s/kb (L30R; E230K; E507K; E189K) cycling conditions (FIG. 14). The PCR of 1825 bp amplicon from phage lambda DNA performed with commercial Taq polymerase, wt His-Taq polymerase and single amino acid mutant polymerases: 1—ZipRuler™ Express DNA Ladder 1 (Fermentas, # SM1373); 2—Taq DNA Pol (Fermentas, # EP0404); 3—His-Taq wt; 4—His-Taq L30P; 5—His-Taq L30R; 6—His-Taq E230K; 7—His-Taq D452N; 8—His-Taq G504S; 9—His-Taq E507K; 10—His-Taq E189K. Three different in cycling length programs (Normal, Fast, Very fast) were used.
A—PCR was performed in $(NH_4)_2SO_4$ based buffer.
B—PCR was performed in KCl based buffer.

Human genomic DNA amplification (~2.5 kbp fragment) was performed using ~50 s/kb (normal), ~25 s/kb (fast) and 12 s/kb (very fast) extension rates. In this test PCR wt Taq DNA polymerase used as a control has synthesized only minor amount of 2.5 kbp DNA fragment even under normal (~50 s/kb) cycling conditions (FIG. 15). The PCR of 2.5 kbp amplicon from human genomic DNA performed with commercial Taq polymerase, wt His-Taq polymerase and single amino acid mutant polymerases: 1—ZipRuler™ Express DNA Ladder 1 (Fermentas, # SM1373); 2—Taq DNA Pol (Fermentas, # EP0404); 3—His-Taq wt; 4—His-Taq E189K; 5—His-Taq E230K; 6—His-Taq E507K. Three different in cycling length programs (Normal, Fast, Very fast) were used.
A—PCR was performed in $(NH_4)_2SO_4$ based buffer.
B—PCR was performed in KCl based buffer.

Meanwhile mutant enzymes (point mutants) identified in our screening were able to amplify target under fast ~25 s/kb and even very fast ~12 s/kb (E189K; E230K; E507K) cycling conditions in $(NH_4)_2SO_4$ based buffer (FIG. 15A). Using KCl based buffer some mutant enzymes (point mutants) were able to amplify target under fast ~25 s/kb (E230K; E507K) and even very fast ~12 s/kb (E230K; E507K) cycling conditions (FIG. 15B). Many more point mutants of Taq DNA polymerase identified during our screenings were tested in the same type PCR assay under normal, fast and very fast cycling conditions. Summarized data on all PCR are given in Table 4. The Taq mutant considered to be fast if it was able to amplify both targets from phage lambda and human genomic DNA under fast cycling conditions at least in one buffer system (with $(NH_4)_2SO_4$ or with KCl): E76G; E76A; D551N; I553V; D732G; F73V; H75R; K206R; A439T; F749V; D452N; G504S (Table 4). The Taq mutant considered to be very fast if it was able to amplify both targets from phage lambda and human genomic DNA under very fast cycling conditions at least in one buffer system (with $(NH_4)_2SO_4$ or with KCl): E90K; E189K; E230K; E507K; H676R; H28R; E76K; E734K; L30R (Table 4).

Two high-throughput screenings using Taq mutants libraries L0 or L3 were performed in this example. The frequencies of all found mutations are calculated and given in FIGS. 11 and 13. As in Example 1 most of mutants either possess eliminated negative charge (D452N, E507G, E507A, D144G, D144N, E90G, E397G), added positive charge (L30R, L311R, H75R) or changed negative charge to positive one (E230K, E189K, E397K). Consequently mutant polymerases became more positively charged and could have increased affinity to negatively charged substrate (DNA). In order to test the polymerase affinity to DNA we have measured dissociation constant (Kd) value of protein-DNA interaction using electrophoretic mobility shift assay (EMSA). Calculated Kd values for wt Taq DNA polymerase and different mutant variants are summarized in the Table 5. The Kd of wt Taq DNA polymerase and DNA oligoduplex complex was obtained to be in the range of 1.71-3.97 nM (Table 2). In addition to already previously identified mutants with increased affinity Kd<1 nM (E230K, E189K) we have found, that mutants A348V, H75R and L351F have Kd<1 nM (Table 1) and should be attributed to the group of high affinity Taq mutants described in Example 1 (Table 2).

Mutants of Taq DNA polymerase able to perform PCR under fast or very fast conditions could be used in fast PCR and qPCR applications, saving instrument and researcher time, increasing laboratory throughput volume.

Methods and Materials
Polymerase Purification
  The same as in Example 1.
Polymerase Unit Definition Assay
  The same as in Example 1.
Mutagenic PCR
  The same as in Example 1.
Mutant Taq DNA Polymerases Synthesize DNA Faster in End-Point PCR than Wild-Type Taq
Amplification of 1825 bp Phage Lambda DNA Target with Mutant Taq DNA Polymerases
  PCR mixtures comprising 10 mM Tris-HCl (pH 8.8), 50 mM KCl, 0.08% (v/v) Nonidet P40, 1.5 mM MgCl$_2$ (buffer with KCl) or 75 mM Tris-HCl (pH 8.8), 20 mM (NH$_4$)$_2$SO$_4$, 0.01% (v/v) Tween 20, 2 mM MgCl$_2$ (buffer with (NH$_4$)$_2$SO$_4$) and dNTPs (200 µM each), 0.5 µM each of primer 7 and 8 (Table 3), 0.25 ng phage lambda DNA, 0.5 u of polymerase in a total volume of 25 µL were subjected to the following three thermocycling conditions:
  1) 5 min at 95° C. followed by 20 cycles of 30 s 95° C., 30 s 60° C., 60 s 72° C.;
  2) 5 min at 95° C. followed by 20 cycles of 30 s 95° C., 10 s 60° C., 20 s 72° C.;
  3) 5 min at 95° C. followed by 20 cycles of 30 s 95° C., 5 s 60° C., 5 s 72° C.
  PCR was performed on Eppendorf Mastercycler, using "BLOCK CONTROL" option, ramping slope 3°/s. PCR products were analyzed in 1% agarose gel electrophoresis.
Amplification of 2.5 kb Human Genomic DNA Target with Mutant Taq Polymerases
  PCR mixtures (25 µL) comprising 10 mM Tris-HCl (pH 8.8), 50 mM KCl, 0.08% (v/v) Nonidet P40, 1.5 mM MgCl$_2$ (buffer with KCl) or 75 mM Tris-HCl (pH 8.8), 20 mM (NH$_4$)$_2$SO$_4$, 0.01% (v/v) Tween 20, 2 mM MgCl$_2$ (buffer with (NH$_4$)$_2$SO$_4$) and dNTPs (200 µM each), 0.5 µM each of primer 9 and 10 (Table 3), 125 ng human genomic DNA (blood purified, using "Genomic DNA purification Kit" (K0512—Fermentas)), 0.5 u of polymerase were subjected to the following thermocycling conditions:
  1) 5 min at 95° C. followed by 30 cycles of 30 s 95° C., 30 s 65° C., 2 min 72° C.
  2) 5 min at 95° C. followed by 30 cycles of 30 s 95° C., 20 s 65° C., 1 min 72° C.
  3) 5 min at 95° C. followed by 30 cycles of 30 s 95° C., 10 s 60° C., 30 s 72° C.
  PCR was performed on Eppendorf Mastercycler, using "BLOCK CONTROL" option, ramping slope 3°/s. PCR products were analyzed in 1% agarose gel electrophoresis.
Increased Affinity of Mutant Taq DNA Polymerases for Primer-Template DNA
  The same as in Example 1.

EXAMPLE 3

Mutants of Taq DNA Polymerase Resistant to Different PCR Inhibitors

Mutant polymerases with increased resistances could be used in PCR and qPCR applications without target DNA purification step (directly after the lysis or after partial/simplified purification step). Consequently we have tested most interesting Taq DNA polymerase mutants identified in example 1 and example 2 in PCR performed with various inhibitors known to be incompatible with wt Taq DNA polymerase. PCR was performed on phage lambda DNA using Taq DNA polymerase (recombinant, Fermentas, # EP0404) and wt His-Taq as the controls. The set of Taq DNA polymerase single amino acid mutants (E189K; E230K; E507K; H28R; E90K; E76K; H676R; L30R; D452N; E734K; D732G; D551N; I553V; G504S; H75R; E76G; E76A; A348V; A439T; E734G) was tested for increased resistance to different PCR inhibitors (blood; SDS, GuHCl, heparin).
  Typical picture of PCR inhibition with blood is given in FIG. 16. The PCR of 1.825 kbp amplicon from phage lambda DNA was performed in the presence of 0-8% of blood either with commercial Taq polymerase (Fermentas, # EP0404), or wt His-Taq polymerase, or single amino acid mutant polymerases (E189K; E230K; E507K, H28R). M-GeneRuler™ Express DNA Ladder, ready-to-use, 100-5000 bp (Fermentas, # SM1553). Under chosen PCR conditions neither commercial Taq, nor wt his-Taq were able to synthesize 1.8 kbp DNA fragment even in the presence of 0.5% of blood. Meanwhile mutant polymerases (E189K, E230K, E507K, H28R) were able to perform PCR in the presence of 4-8% of blood.
  Typical picture of PCR inhibition with SDS is given in FIG. 17. The PCR of 1.825 kbp amplicon from phage lambda DNA was performed in the presence of 0.000-0.015% of SDS either with commercial Taq polymerase (Fermentas, # EP0404), or wt His-Taq polymerase, or single amino acid mutant polymerases (E189K; E230K; E507K, H28R). M-GeneRuler™ Express DNA Ladder, ready-to-use, 100-5000 bp (Fermentas, # SM1553). Under chosen PCR conditions commercial Taq and wt his-Taq synthesized specific DNA fragment in the presence of 0.0025% and 0.001% of SDS respectively. Meanwhile mutant polymerases (E189K, E230K, E507K) were able to perform PCR in the presence of 0.005-0.0075% of SDS.
  Typical picture of PCR inhibition with GuHCl is given in FIG. 18. The PCR of 1.825 kbp amplicon from phage lambda DNA was performed in the presence of 0-100 mM of GuHCl either with commercial Taq polymerase (Fermentas, # EP0404), or wt His-Taq polymerase, or single amino acid mutant polymerases (E189K; E230K; E507K, H28R). M-GeneRuler™ Express DNA Ladder, ready-to-use, 100-5000 bp (Fermentas, # SM1553). Under chosen PCR conditions commercial Taq synthesized specific DNA fragment in the presence of 20 mM of GuHCl. Another control enzyme wt his-Taq (should be used for direct comparison with Taq polymerase mutants) was not able to synthesize 1.8 kbp DNA fragment even in the presence of 10 mM of GuHCl. Meanwhile mutant polymerases (E189K, E230K, E507K, H28R) were able to perform PCR in the presence of 40-70 mM of GuHCl.
  Typical picture of PCR inhibition with heparin is given in FIG. 19. The PCR of 1.825 kbp amplicon from phage lambda DNA was performed in the presence of 0-0.039 UPS heparin (per 25 µl of PCR reaction) either with commercial Taq polymerase (Fermentas, # EP0404), or wt His-Taq polymerase, or single amino acid mutant polymerases (E189K; E230K; E507K, D452N; D551N; G504S). M-GeneRuler™ Express DNA Ladder, ready-to-use, 100-5000 bp (Fermentas, # SM1553).
  1—no heparin;
  2—0.001 UPS heparin (per 25 µl of PCR reaction);
  3—0.0025 UPS heparin (per 25 µl of PCR reaction);
  4—0.00625 UPS heparin (per 25 µl of PCR reaction);
  5—0.015625 UPS heparin (per 25 µl of PCR reaction);
  6—0.039 UPS heparin (per 25 µl of PCR reaction). Under chosen PCR conditions commercial Taq and wt his-Taq synthesized specific DNA fragment in the presence of 0.0025 UPS and 0.001 UPS heparin (per 25 µl of PCR reaction) respectively. Meanwhile mutant polymerases (D452N, D551N, G504S) were able to perform PCR in the presence of 0.0062 UPS heparin (per 25 μl of PCR reaction).

Summarized data on all PCR inhibition experiments are given in Table 6. Tested Taq DNA polymerase mutants have different resistances to various PCR inhibitors. Some mutants are more resistant to blood (E189K, E230K, E507K, H28R), some mutants are more resistant to SDS (E189K, E230K, E507K, E90K, E76K, H676R, L30R, D452N, E734K, D732G, D551N, I553V, G504S, H75R, E76G, E76A, A439T, E734G), some mutants are more resistant to GuHCL (E189K, E230K, E507K, H28R, E90K, E76K, H676R, L30R) and some mutants are more resistant to heparin (D452N, D551N, G504S) (Table 6). Most interesting are Taq mutants with the highest resistances to tested PCR inhibitors (except heparin) and increased amplification speed: E189K, E230K and E507K (Table 6 and Table 4).

Mutants of Taq DNA polymerase able to perform PCR in the presence of different inhibitors are very important and can be used for amplification of partially purified or unpurified DNA samples. Skipped or simplified nucleic acids purification step makes diagnostic procedure faster, cheaper and more convenient for user. Different "direct PCR" kits from plants, tissues, blood, etc could be prepared and commercialized on the basis of newly discovered mutations and their combinations.

Methods and Materials
The Measurements of Wt Taq DNA Polymerase and Mutant Enzymes Resistance to Different PCR Inhibitors
Amplification of 1825 bp Phage Lambda DNA Target with Mutant Taq DNA Polymerases PCR mixtures comprising 50 mM Tricine (pH 8.8), 20 mM $(NH_4)_2SO_4$, 0.01% (v/v) Tween 20, 2.5 mM $MgCl_2$, dNTPs (200 μM each), 0.5 μM each of primer 7 and 8 (Table 3), 0.25 ng phage lambda DNA, INHIBITOR X and 1 u of polymerase in a total volume of 25 μL were subjected to the following thermocycling conditions: 5 min at 95° C. followed by 30 cycles of 20 s 95° C., 25 s 60° C., 80 s 72° C. PCR was performed on Eppendorf Mastercycler epgradient S, PCR products were analyzed in 1% agarose gel electrophoresis.

Inhibitor X:
Fresh blood stabilized with sodium citrate—0%, 0.5%, 1%, 2%, 4%, 8% (v/v);
SDS (Sodium Dodecyl Sulphate, Amresco 0227-1 kg)—0%, 0.001%, 0.0025%, 0.005%, 0.0075%, 0.015% (w/v);
GuHCl (Guanidine Hydrochloride, Roth 0037.1)—0 mM, 10 mM, 20 mM, 40 mM, 70 mM, 100 mM;
Heparin (Sigma, H3125)—0, 0.001, 0.0025, 0.00625, 0.015625, 0.039 UPS heparin (per 25 ml of PCR reaction).

TABLE 1

The threshold concentrations of SYBR Green I dye (at which full length DNA fragment is still synthesized) determined for wt and different mutants of Taq DNA polymerase. SYBR Green I stock concentration is 10'000X and amplification was performed using 0.2-5X concentration of dye.

| Mutant name | Amplification of 200 bp fragment from plasmid DNA | Amplification of 500 bp fragment from human genomic DNA |
|---|---|---|
| wt His-Taq | 0.5 | 0.2-0.5 |
| H28R | 1 | 1 |
| G38R | 1 | 1 |
| E76G | 1 | n.d. |
| E90K | 1.5 | 1.5 |
| E189K | 1.5 | 2.5 |
| E230K | 2.5 | 2 |
| E315K | 1.5 | 1.5 |
| E507A | 2 | 1.5 |
| E507K | 2 | 3 |
| L552R | 2 | 1.5 |
| D578N | 1 | 1.5 |
| H676R | 1 | 1.5 |
| Q680R | 1 | 1 |
| D732G | 1 | 1 |
| H28R + E507K | 2.5 | n.d. |
| H28R + Q680R | 1.5 | 1.5 |
| E507K + Q680R | 2.5 | n.d. |
| L552R + Q680R | 3.5 | n.d. |
| E230K + E507K | 4.5 | 3 |
| E189K + E507K | 5 | 4 |
| E315K + E507K | 4 | 4 |
| E230K + E315K | 3 | 2.5 |
| E507K + L552R | n.d. | 3 |
| E189K + E230K + E507K | 5 | 3.5 | n.d.—not determined

TABLE 2

The dissociation constants (Kd) of wt and mutant Taq DNA polymerases and oligoduplex substrate determined without and with (0.2X) SYBR Green I dye. EMSA measurements were performed at fixed 0.1 nM concentration of oligoduplex and 0.25-100 nM concentration gradient of polymerase.

| Mutant name | Kd, nM | Kd (+0.2X SYBR Green I), nM |
|---|---|---|
| wt His-Taq | 1.71-3.97* | 6.17-9.39 |
| H28R | 0.83-1.59 | 2.61-8.39 |
| G38R | 2.47 | 7.24 |
| E90K | 1.53 | 7.86 |
| E189K | 0.40 | 2.69 |
| E230K | 0.37 | 4.76 |
| E315K | 0.50 | 2.50 |
| E507A | 1.14 | 7.29 |
| E507K | 0.18-0.19 | 3.91-4.22 |
| L552R | 0.53 | 1.88-7.49 |
| D578N | 0.70 | 2.66 |
| H676R | 4.87 | 10.94 |
| Q680R | 3.18 | 9.61 |
| D732G | 1.82 | 8.10 |
| H28R + E507K | 0.25 | 4.71 |
| H28R + Q680R | 0.95 | 2.17 |
| E507K + Q680R | 0.71 | 3.25 |
| L552R + Q680R | 0.29 | 2.63 |
| E230K + E507K | 0.18 | 2.73-7.95 |
| E189K + E507K | 0.29 | 6.61 |
| E315K + E507K | 0.30 | 3.66 |
| E230K + E315K | 0.37 | 2.60 |
| E507K + L552R | 0.25 | 2.13 |
| E189K + E230K + E507K | 0.14 | 0.43 |

*the range of Kd values is given if more than one experiment was performed

TABLE 3

The oligonucleotide sequences used in Examples.

| Oligo-nucleotide | Designation | Sequence (5' to 3') |
|---|---|---|
| Primer 1 | agseq1 | GCGTTATCTCATAGACAAGGGC |
| Primer 2 | agseq2 | GTAAGTTATTATCACATCCGGGTC |
| Primer 3 | Pra1 | AATGGCTAGCTGGAGCCAC |
| Primer 4 | Seq prom | TATCTCCTCAATAGCGGAGTCATC |
| Primer 5 | Forward GAPDH | CAAGGTCATCCATGACAACTTTG |
| Primer 6 | Reverse GAPDH | GTCCACCACCCTGTTGCTGTAG |
| Oligo-nucleotide 1 | LA422 | TTTTAGCCGCTAGAGTCGACCTGC |
| Oligo-nucleotide 2 | LA424 | GGAGACAAGCTTGTATGCCTGCAGGTCGACTCTAGCGGCTAAAA |
| Primer 7 | L-16 | ATCCTGAACCCATTGACCTCCAAC |
| Primer 8 | L-19 | ACTGAATCCCCGATCATCTATCGC |
| Primer 9 | | CAGCTCAGTGGTTTTCATTGGTTG |
| Primer 10 | | CTGTGAGGCAGAGACAGCAGAGAC |

TABLE 4

The summarized data on different PCR experiments performed under normal (1), fast (2) and very fast (3) cycling conditions. PCR was performed on two different targets: phage lambda and human genomic DNA in two different buffers based either on $(NH_4)_2SO_4$ or on KCl.

| | amplification of 1825 bp DNA fragment from phage lambda DNA | | | | | | amplification of 2.5 kbp DNA fragment from human genomic DNA | | | | | |
|---|---|---|---|---|---|---|---|---|---|---|---|---|
| | with $(NH_4)_2SO_4$ | | | with KCl | | | with $(NH_4)_2SO_4$ | | | with KCl | | |
| Polymerase | 1 | 2 | 3 | 1 | 2 | 3 | 1 | 2 | 3 | 1 | 2 | 3 |
| Taq DNA pol. Fermentas #EP0404 | ++ | | | ++ | | | + | | | + | | |
| wt His-Taq | ++ | | | ++ | | | + | | | + | | |
| Y24H | ++ | | | ++ | ++ | | | | | ++ | | |
| T26P | ++ | | | +++ | + | | | | | + | | |
| F27S | + | | | +++ | + | | | | | + | | |
| G38R | +++ | | | +++ | ++ | | | | | + | | |
| E76G | +++ | ++ | | +++ | + | | ++ | + | | ++ | + | |
| E90K | +++ | ++ | + | ++ | ++ | ++ | ++ | ++ | + | nsp | | |
| E189K | +++ | ++ | | + | + | + | ++ | ++ | + | + | | |
| E230K | +++ | ++ | + | +++ | ++ | + | +++ | ++ | + | + | + | |
| E507K | +++ | ++ | + | +++ | ++ | + | +++ | ++ | ++ | + | + | + |
| D551N | +++ | ++ | | +++ | +++ | + | +++ | ++ | | +++ | ++ | |
| I553V | ++ | + | | +++ | + | + | ++ | | | +++ | ++ | |
| H676R | +++ | ++ | | +++ | +++ | | +++ | ++ | | +++ | ++ | + |
| D732G | +++ | ++ | | +++ | ++ | ++ | +++ | ++ | | ++ | ++ | |
| H28P | ++ | | | +++ | | | + | | | + | + | |
| H28R | +++ | +++ | + | +++ | ++ | + | +++ | ++ | + | +++ | ++ | |
| F73V | ++ | | | ++ | + | | + | | | + | + | |
| H75R | +++ | ++ | | +++ | ++ | + | +++ | | | +++ | | |
| E76A | +++ | ++ | | +++ | ++ | | ++ | ++ | | ++ | + | |
| E76K | +++ | +++ | + | +++ | ++ | + | +++ | +++ | ++ | nsp | + | |
| K143E | + | | | ++ | | | | | | | | |
| K206R | ++ | + | | ++ | + | | ++ | | | + | + | |
| R275G | ++ | | | +++ | | | | | | | | |
| F278L | ++ | | | + | | | | | | + | + | |
| D344N | ++ | | | ++ | ++ | | + | | | | | |
| L351F | ++ | + | | +++ | ++ | | | | | | | |
| E397K | + | | | ++ | + | | | | | | | |
| N415D | ++ | | | ++ | | | | | | + | + | |
| A439T | +++ | + | | +++ | ++ | | ++ | | | ++ | + | |
| E734G | +++ | + | | +++ | +++ | | ++ | | | + | | |
| E734K | +++ | ++ | + | ++ | ++ | ++ | ++ | ++ | + | nsp | | |
| F749L | | | | + | | | | | | | | |
| F749V | ++ | | | ++ | + | | ++ | | | + | + | |

TABLE 4-continued

The summarized data on different PCR experiments performed under normal (1), fast (2) and very fast (3) cycling conditions. PCR was performed on two different targets: phage lambda and human genomic DNA in two different buffers based either on $(NH_4)_2SO_4$ or on KCl.

| | amplification of 1825 bp DNA fragment from phage lambda DNA | | | | | | amplification of 2.5 kbp DNA fragment from human genomic DNA | | | | | |
|---|---|---|---|---|---|---|---|---|---|---|---|---|
| | with $(NH_4)_2SO_4$ | | | with KCl | | | with $(NH_4)_2SO_4$ | | | with KCl | | |
| Polymerase | 1 | 2 | 3 | 1 | 2 | 3 | 1 | 2 | 3 | 1 | 2 | 3 |
| L30P | ++ | | | ++ | | | + | | | | | |
| L30R | +++ | ++ | + | +++ | ++ | + | +++ | ++ | + | ++ | ++ | |
| D452N | +++ | + | | +++ | ++ | + | +++ | +++ | | ++ | ++ | |
| G504S | +++ | + | + | +++ | ++ | + | ++ | ++ | | +++ | | |
| F285S | | | | ++ | | | | | | | | |
| L311F | ++ | | | + | | | | | | + | | |
| A348V | ++ | | | +++ | ++ | | | | | | | | nsp—non-specific amplification
+ - minor amount of target PCR fragment
++ - normal amount of target PCR fragment
+++ - abundant amount of target PCR fragment

TABLE 5

The values of dissociation constant (Kd) determined for oligoduplex substrate and mutant Taq DNA polymerases in Example 2. EMSA measurements were performed at fixed 0.1 nM concentration of oligoduplex and 0.25-100 nM concentration gradient of polymerase. The WT-Taq polymerase Kd is 1.71-3.97 nM.

| Mutant name (1st screening) | Frequency | Kd, nM | Mutant name (2nd screening) | Frequency | Kd, nM |
|---|---|---|---|---|---|
| E230K | 33 | 0.37* | F73V | 5 | 4.56-4.92 |
| L30P | 32 | 3.08 | K206R | 5 | 2.42-12.72 |
| L30R | | 2.43 | | | |
| D452N | 18 | 1.14 | L30P | 3 | 3.08 |
| G504S | 15 | 6.03 | H75R | 3 | 0.57 |
| L311F | 5 | 3.20 | E90K | 3 | 1.53* |
| E507A | 5 | 1.14* | K143E | 3 | 4.09 |
| E189K | 4 | 0.40* | L351F | 3 | 0.85 |
| F285S | 3 | 2.63 | E397K | 3 | 2.64 |
| A348V | 3 | 0.62 | A439T | 3 | 3.06 |

*the Kd values of wt-Taq, E230K, E507A, E189K, E90K are taken from Example 1 (Table 2).

TABLE 6

The summarized data on different PCR inhibition experiments performed with blood, SDS, GuHCL and heparin. The threshold concentrations of inhibitor under which specific 1.825 kbp DNA fragment is still synthesized are indicated.

| Enzyme | Blood, % (v/v) | SDS, % (w/v) | GuHCl, mM | heparin, UPS per 25 μl of PCR |
|---|---|---|---|---|
| Taq DNA pol. Fermentas #EP0404 | 0 | 0.0025 | 20 | 0.0025 |
| wt His-Taq | 0 | 0.0025 | 0 | 0.001 |
| E189K | 8 | 0.0075 | 70 | 0.0025 |
| E230K | 4 | 0.005 | 70 | 0.0025 |
| E507K | 8 | 0.0075 | 70 | 0.0025 |
| H28R | 4 | 0.0025 | 40 | 0.0025 |
| E90K | 2 | 0.005 | 40 | 0.0025 |
| E76K | 2 | 0.005 | 40 | 0.0025 |
| H676R | 2 | 0.005 | 40 | 0.0025 |
| L30R | 2 | 0.005 | 40 | 0.0025 |
| D452N | 1 | 0.0075 | 20 | 0.00625 |
| E734K | 1 | 0.005 | 20 | 0.0025 |
| D732G | 1 | 0.005 | 20 | 0.0025 |
| D551N | 1 | 0.005 | 20 | 0.00625 |
| I553V | 1 | 0.0075 | 20 | 0.0025 |
| G504S | 1 | 0.005 | 20 | 0.00625 |
| H75R | 0.5 | 0.005 | 20 | 0.0025 |
| E76G | 0 | 0.005 | 20 | 0.0025 |
| E76A | 0 | 0.005 | 20 | 0.0025 |
| A348V | 0 | 0.0025 | 0 | 0.001 |
| A439T | 0 | 0.005 | 20 | 0.0025 |
| E734G | 0 | 0.005 | 20 | 0 |

TABLE 7

Summary of Taq DNA polymerase mutants

| Mutation | Increased speed | Increased affinity | Resistance to SYBR Green | Resistance to blood | Resistance to SDS | Resistance to GuHCl | Resistance to heparin |
|---|---|---|---|---|---|---|---|
| H28R | + | | | + | | | + |
| L30R | + | | | + | + | + | + |
| G38R | | | + | | | | |
| F73V | + | | | | | | |
| H75R | + | + | | | | + | |
| E76A | + | | | | | + | |

TABLE 7-continued

Summary of Taq DNA polymerase mutants

| Mutation | Increased speed | Increased affinity | Resistance to SYBR Green | Resistance to blood | Resistance to SDS | Resistance to GuHCl | Resistance to heparin |
|---|---|---|---|---|---|---|---|
| E76G | + | | + | | + | | |
| E76K | + | | | + | + | + | |
| E90K | + | | + | + | + | + | |
| E189K | + | + | + | + | + | + | |
| K206R | + | | | | | | |
| E230K | + | + | + | + | + | + | |
| E315K | | + | + | | | | |
| A348V | | + | | | | | |
| L351F | | + | | | | | |
| A439T | + | | | | + | | |
| D452N | + | | | + | + | | + |
| G504S | + | | | + | + | | + |
| E507A | | | + | | | | |
| E507K | + | + | + | + | + | + | |
| D551N | + | | | + | + | | + |
| L552R | | + | + | | | | |
| I553V | + | | | + | + | | |
| D578N | | + | + | | | | |
| H676R | + | | + | + | + | + | |
| Q680R | | | + | | | | |
| D732G | + | | + | + | + | | |
| E734G | | | | | + | | |
| E734K | + | | | + | + | | |
| F749V | + | | | | | | |
| H28R + E507K | | + | + | | | | |
| H28R + Q680R | | + | + | | | | |
| E507K + Q680R | | + | + | | | | |
| L552R + Q680R | | + | + | | | | |
| E230K + E507K | | + | + | | | | |
| E189K + E507K | | + | + | | | | |
| E315K + E507K | | + | + | | | | |
| E230K + E315K | | + | + | | | | |
| E507K + L552R | | + | + | | | | |
| E189K + E230K + E507K | | + | + | | | | |

Summarized information from Tables 1, 2, 4, 5, 6 and FIG. 19.

REFERENCES

Abramson, R. D. and Gelfand, D. H. (1993). 5' to 3' exonuclease mutations of thermostable DNA polymerases. U.S. Pat. No. 5,466,591

Abramson, R. D. and Gelfand, D. H. (1993). 5' to 3' exonuclease mutations of thermostable DNA polymerases. U.S. Pat. No. 5,466,591

Allawi, H., BARTHOLOMAY, C. T, CHEHAK, L, CURTIS, M. L, EIS, P. S, HALL, J. G, IP, H. S, KAISER, M, KWIATKOWSKI, R. W. J, LUKOWIAK, A. A, LYAMICHEV, V, MA, W, OLSON-MUNOZ, M. C, OLSON, S. M, SCHAEFER, J. J, SKRZYPCZYNSKI, Z, TAKOVA, T. Y, VEDVIK, K. L, LYAMICHEV, N. E and NERI, B. P. (2001). DETECTION OF RNA. WO/2001/090337

Barnes, W. M. and Kermekchiev, M. B. (2000). Cold sensitive mutant DNA polymerases. U.S. Pat. No. 6,214,557

Brandis, J., Bloom, C and Richards, J. H. (1998). DNA polymerases having improved labeled nucleotide incorporation properties. U.S. Pat. No. 6,265,193

Brandis, J., Bloom, C and Richards, J. H. (1998). DNA polymerases having improved labeled nucleotide incorporation properties. U.S. Pat. No. 6,265,193

Gudnason, H., Dufva, M., Bang, D. D. and Wolff, A. (2007). Comparison of multiple DNA dyes for real-time PCR: effects of dye concentration and sequence composition on DNA amplification and melting temperature *Nucleic Acids Res,* 35, e127

Hardin, S., Gao, X, Briggs, J, Willson, R and Tu, S. (2006). Mutant polymerases. US2007/0172861

Holliger, P., Ghadessy, F and D'Abbadie, M. (2006). Generating a pol A DNA polymerase, useful in PCR amplification, sequencing of damaged DNA templates, or in creating novel polymerase activities, comprises preparing and expressing nucleic acid encoding an engineered DNA polymerase. US20070020653

Holliger, P., Ghadessy, F and Ong, J. L. (2001). Directed evolution method. EP1806406

Jestin, J., Vichier-guerre, S and Ferris, S. (2005). Methods for Obtaining Thermostable Enzymes, Dna Polymerase I Variants from *Thermus Aquaticus* Having New Catalytic Activities, Methods for Obtaining the Same, and applications to the Same. US20080014609

Kermekchiev, M. and Kirilova, L. (2006). USE OF TAQ POLYMERASE MUTANT ENZYMES FOR DNA AMPLIFICATION IN THE PRESENCE OF PCR INHIBITORS. WO08034110A2

Kermekchiev, M. B. and Barnes, W. M. (2004). USE OF WHOLE BLOOD IN PCR REACTIONS. EP1747290A2

Kermekchiev, M. B., Kirilova, L. I, Vail, E. E and Barnes, W. M. (2009). Mutants of Taq DNA polymerase resistant to PCR inhibitors allow DNA amplification from whole blood and crude soil samples. *Nucleic Acids Res,* 37, e40.

Leconte, A. M., Patel, M. P, Sass, L. E, McInerney, P, Jarosz, M, Kung, L, Bowers, J. L, Buzby, P. R, Efcavitch, J. W and Romesberg, F. E. (2010). Directed Evolution of DNA Polymerases for Next-Generation Sequencing. *Angew Chem Int Ed Engl*

Loeb, L. A., Hood, L and Suzuki, M. (1996). Thermostable polymerases having altered fidelity and method of identifying and using same. U.S. Pat. No. 6,395,524

Nath, K., Sarosy, J. W, Hahn, J and Di Como, C. J. (2000). Effects of ethidium bromide and SYBR Green I on different polymerase chain reaction systems. *J Biochem Biophys Methods*, 42, 15-29.

Patel, P. H. and Loeb, L. A. (2001). DNA polymerase mutant having one or more mutations in the active site. U.S. Pat. No. 6,602,695

Tabor, S. and Richardson, C. (1994). DNA polymerase having modified nucleotide binding site for DNA sequencing. U.S. Pat. No. 5,614,365

Vatta, P., Brandis, J. W, Bolchakova, E. V and Spurgeon, S. L. (2005). Mutant DNA polymerases and methods of use. US20060223067

Zaccolo, M., Williams, D. M, Brown, D. M and Gherardi, E. (1996). An approach to random mutagenesis of DNA using mixtures of triphosphate derivatives of nucleoside analogues. *J Mol Biol*, 255, 589-603.

Zhang, Z., Kermekchiev, M. B and Barnes, W. M. (2010). Direct DNA amplification from crude clinical samples using a PCR enhancer cocktail and novel mutants of taq. *J Mol Diagn*, 12, 152-161.

Zipper, H., Brunner, H., Bernhagen, J. and Vitzthum, F. (2004). Investigations on DNA intercalation and surface binding by SYBR Green I, its structure determination and methological implications. *Nucleic Acids Res*, 32, e103

The invention claimed is:

1. A Taq DNA polymerase mutant comprising SEQ ID NO: 13 amino acid sequence with a mutation at position E230 and optionally one or more of the following mutations: E189K, H28R, L30R, G38R, F73V, H75R, E76A, E76G, E76K, E90K, K206R, E315K, A348V, L351F, A439T, D452N, G504S, E507A, E507K, D551N, L552R, I553V, D578N, H676R, Q680R, D732G, E734G, E734K, and F749V; wherein the polymerase mutant exhibits relative to wild-type DNA polymerase increased polymerase speed, increased affinity to DNA substrate and/or increased resistance to a DNA polymerase inhibitor.

2. A DNA polymerase mutant according to claim 1, wherein the amino acid sequence has a mutation at no more than three amino acid positions.

3. A DNA polymerase mutant according to claim 2, wherein the amino acid sequence has a mutation at only one amino acid position.

4. A DNA polymerase mutant according to claim 2, wherein the amino acid sequence has a mutation at only two amino acid positions.

5. A DNA polymerase mutant according to claim 1, which exhibits increased polymerase speed relative to wild-type DNA polymerase.

6. A DNA polymerase mutant according to claim 5, wherein the Taq DNA polymerase amino acid sequence comprises one or more of the following mutations: E189K, E230K, E507K, H28R, L30R, F73V, H75R, E76A, E76G, E76K, E90K, K206R, A439T, D452N, G504S, D551N, I553V, H676R, D732G, E734G, F749V.

7. A DNA polymerase mutant according to claim 5, which exhibits an increased polymerase speed which is at least 1.5 times faster than wild-type DNA polymerase.

8. A DNA polymerase mutant according to claim 5, which exhibits an increased polymerase speed which is at least 3 times faster than wild-type DNA polymerase.

9. A DNA polymerase mutant according to claim 5, which exhibits an increased polymerase speed which is at least 12 times faster than wild-type DNA polymerase.

10. A DNA polymerase mutant according to claim 1, which exhibits increased affinity to DNA substrate relative to wild-type DNA polymerase.

11. A DNA polymerase mutant according to claim 10, wherein the Taq DNA polymerase amino acid sequence comprises one or more of the following mutations: E189K, E230K, E507K, H75R, E315K, A348V, L351F, L552R, D578N.

12. A DNA polymerase mutant according to claim 10, wherein the Kd for a DNA oligoduplex substrate is no more than 1 nM, as measured by electrophoretic shift mobility assay following incubation in 40 mM Tris, 20 mM acetic acid, 1 mM EDTA at pH8.4, in the presence of 10% v/v glycerol at 4° C. for 30 mins.

13. A DNA polymerase mutant according to claim 1, which exhibits increased resistance to a DNA polymerase inhibitor selected from SYBR Green I dye, blood, SDS, guanidinium salts and heparin.

14. A DNA polymerase mutant according to claim 13, wherein the Taq DNA polymerase amino acid sequence comprises one or more of the following mutations: E189K, E230K, E507K, H28R, L30R, G38R, H75R, E76A, E76G, E76K, E90K, E315K, A439T, D452N, G504S, E507A, D551N, L552R, I553V, D578N, H676R, Q680R, D732G, E734G, E734K.

15. A DNA polymerase mutant according to claim 13, wherein the Kd for a DNA oligoduplex substrate in the presence of 0.4 µM SYBR Green I dye is no more than 10 nM, as measured by electrophoretic shift mobility assay following incubation in 40 mM Tris, 20 mM acetic acid, 1 mM EDTA at pH8.4, in the presence of 10% v/v glycerol at 4° C. for 30 mins.

16. A DNA polymerase mutant according to claim 1, wherein the amino acid sequence has a mutation at only two amino acid positions; the DNA polymerase mutant exhibits increased affinity to DNA substrate relative to wild-type DNA polymerase; and/or the DNA polymerase mutant exhibits increased resistance to a DNA polymerase inhibitor selected from SYBR Green I dye, blood, SDS, guanidinium salts and heparin; and wherein the Taq DNA polymerase amino acid sequence comprises the following mutations: E230K+E507K or E230K+E315K.

17. A DNA polymerase mutant according to claim 1, wherein the Taq DNA polymerase amino acid sequence comprises one or more of the following mutations: E189K, E230K and E507K.

18. A DNA polymerase mutant according to claim 1, wherein the Taq DNA polymerase amino acid sequence comprises an E230K mutation.

19. A DNA polymerase mutant according to claim 1, wherein the Taq DNA polymerase amino acid sequence comprises an E507K mutation.

20. A kit for nucleic acid amplification, which comprises a DNA polymerase mutant according to claim 1 and one or more reagents for a DNA synthesis reaction.

21. A DNA polymerase obtainable by a process comprising:
(1) subjecting a polynucleotide encoding a Taq DNA polymerase to error-prone PCR to generate a library comprising an array of different polynucleotides:
(2) screening the library for increased polymerase speed, increased polymerase affinity to DNA substrate or increase resistance to a DNA polymerase inhibitor;
(3) selecting one or more DNA polymerases from screening step 2; and
(4) repeating steps 1 to 3 until a final DNA polymerase is obtained;
wherein the final DNA polymerase comprises SEQ ID NO: 13 amino acid sequence with a mutation at position E230, and optionally one or more of the following mutations: E189K, H28R, L30R, G38R, F73V, H75R, E76A, E76G, E76K, E90K, K206R, E315K, A348V, L351F, A439T, D452N, G504S, E507A, E507K, D551N, L552R, I553V, D578N, H676R, Q680R, D732G, E734G, E734K, and F749V.

* * * * *

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Primer 1

<400> SEQUENCE: 1
gcgttatctc atagacaagg gc                                                22

<210> SEQ ID NO 2
<211> LENGTH: 24
<212> TYPE: DNA
<213> ORGANISM: Artificial Sequence
<220> FEATURE:
<223> OTHER INFORMATION: Primer 2

<400> SEQUENCE: 2
gtaagttatt atcacatccg ggtc                                              24

<210> SEQ ID NO 3
<211> LENGTH: 19
<212> TYPE: DNA
<213> ORGANISM: Artificial Sequence
<220> FEATURE:
<223> OTHER INFORMATION: Primer 3

<400> SEQUENCE: 3
aatggctagc tggagccac                                                    19

<210> SEQ ID NO 4
<211> LENGTH: 24
<212> TYPE: DNA
<213> ORGANISM: Artificial Sequence
<220> FEATURE:
<223> OTHER INFORMATION: Primer 4

<400> SEQUENCE: 4
tatctcctca atagcggagt catc                                              24

<210> SEQ ID NO 5
<211> LENGTH: 23
<212> TYPE: DNA
<213> ORGANISM: Artificial Sequence
<220> FEATURE:
<223> OTHER INFORMATION: Primer 5

<400> SEQUENCE: 5
```

```
caaggtcatc catgacaact ttg                                              23

<210> SEQ ID NO 6
<211> LENGTH: 22
<212> TYPE: DNA
<213> ORGANISM: Artificial Sequence
<220> FEATURE:
<223> OTHER INFORMATION: Primer 6

<400> SEQUENCE: 6
gtccaccacc ctgttgctgt ag                                               22

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide 1

<400> SEQUENCE: 7
ttttagccgc tagagtcgac ctgc                                             24

<210> SEQ ID NO 8
<211> LENGTH: 44
<212> TYPE: DNA
<213> ORGANISM: Artificial Sequence
<220> FEATURE:
<223> OTHER INFORMATION: Oligonucleotide 2

<400> SEQUENCE: 8
ggagacaagc ttgtatgcct gcaggtcgac tctagcggct aaaa                       44

<210> SEQ ID NO 9
<211> LENGTH: 24
<212> TYPE: DNA
<213> ORGANISM: Artificial Sequence
<220> FEATURE:
<223> OTHER INFORMATION: Primer 7

<400> SEQUENCE: 9
atcctgaacc cattgacctc caac                                             24

<210> SEQ ID NO 10
<211> LENGTH: 24
<212> TYPE: DNA
<213> ORGANISM: Artificial Sequence
<220> FEATURE:
<223> OTHER INFORMATION: Primer 8

<400> SEQUENCE: 10
actgaatccc cgatcatcta tcgc                                             24

<210> SEQ ID NO 11
<211> LENGTH: 24
<212> TYPE: DNA
<213> ORGANISM: Artificial Sequence
<220> FEATURE:
<223> OTHER INFORMATION: Primer 9

<400> SEQUENCE: 11
cagctcagtg gttttcattg gttg                                             24

<210> SEQ ID NO 12
<211> LENGTH: 24
<212> TYPE: DNA
<213> ORGANISM: Artificial Sequence
```

```
<220> FEATURE:
<223> OTHER INFORMATION: Primer 10

<400> SEQUENCE: 12
ctgtgaggca gagacagcag agac                                              24

<210> SEQ ID NO 13
<211> LENGTH: 832
<212> TYPE: PRT
<213> ORGANISM: Thermus aquaticus

<400> SEQUENCE: 13
```

| Met | Arg | Gly | Met | Leu | Pro | Leu | Phe | Glu | Pro | Lys | Gly | Arg | Val | Leu | Leu |
|---|---|---|---|---|---|---|---|---|---|---|---|---|---|---|---|
| 1 | | | | 5 | | | | | 10 | | | | | 15 | |

| Val | Asp | Gly | His | His | Leu | Ala | Tyr | Arg | Thr | Phe | His | Ala | Leu | Lys | Gly |
|---|---|---|---|---|---|---|---|---|---|---|---|---|---|---|---|
| | | | 20 | | | | | 25 | | | | | 30 | | |

| Leu | Thr | Thr | Ser | Arg | Gly | Glu | Pro | Val | Gln | Ala | Val | Tyr | Gly | Phe | Ala |
|---|---|---|---|---|---|---|---|---|---|---|---|---|---|---|---|
| | | 35 | | | | | 40 | | | | | 45 | | | |

| Lys | Ser | Leu | Leu | Lys | Ala | Leu | Lys | Glu | Asp | Gly | Asp | Ala | Val | Ile | Val |
|---|---|---|---|---|---|---|---|---|---|---|---|---|---|---|---|
| 50 | | | | | 55 | | | | | 60 | | | | | |

| Val | Phe | Asp | Ala | Lys | Ala | Pro | Ser | Phe | Arg | His | Glu | Ala | Tyr | Gly | Gly |
|---|---|---|---|---|---|---|---|---|---|---|---|---|---|---|---|
| 65 | | | | | 70 | | | | | 75 | | | | | 80 |

| Tyr | Lys | Ala | Gly | Arg | Ala | Pro | Thr | Pro | Glu | Asp | Phe | Pro | Arg | Gln | Leu |
|---|---|---|---|---|---|---|---|---|---|---|---|---|---|---|---|
| | | | | 85 | | | | | 90 | | | | | 95 | |

| Ala | Leu | Ile | Lys | Glu | Leu | Val | Asp | Leu | Leu | Gly | Leu | Ala | Arg | Leu | Glu |
|---|---|---|---|---|---|---|---|---|---|---|---|---|---|---|---|
| | | | 100 | | | | | 105 | | | | | 110 | | |

| Val | Pro | Gly | Tyr | Glu | Ala | Asp | Asp | Val | Leu | Ala | Ser | Leu | Ala | Lys | Lys |
|---|---|---|---|---|---|---|---|---|---|---|---|---|---|---|---|
| | | 115 | | | | | 120 | | | | | 125 | | | |

| Ala | Glu | Lys | Glu | Gly | Tyr | Glu | Val | Arg | Ile | Leu | Thr | Ala | Asp | Lys | Asp |
|---|---|---|---|---|---|---|---|---|---|---|---|---|---|---|---|
| 130 | | | | | 135 | | | | | 140 | | | | | |

| Leu | Tyr | Gln | Leu | Leu | Ser | Asp | Arg | Ile | His | Val | Leu | His | Pro | Glu | Gly |
|---|---|---|---|---|---|---|---|---|---|---|---|---|---|---|---|
| 145 | | | | | 150 | | | | | 155 | | | | | 160 |

| Tyr | Leu | Ile | Thr | Pro | Ala | Trp | Leu | Trp | Glu | Lys | Tyr | Gly | Leu | Arg | Pro |
|---|---|---|---|---|---|---|---|---|---|---|---|---|---|---|---|
| | | | | 165 | | | | | 170 | | | | | 175 | |

| Asp | Gln | Trp | Ala | Asp | Tyr | Arg | Ala | Leu | Thr | Gly | Asp | Glu | Ser | Asp | Asn |
|---|---|---|---|---|---|---|---|---|---|---|---|---|---|---|---|
| | | | 180 | | | | | 185 | | | | | 190 | | |

| Leu | Pro | Gly | Val | Lys | Gly | Ile | Gly | Glu | Lys | Thr | Ala | Arg | Lys | Leu | Leu |
|---|---|---|---|---|---|---|---|---|---|---|---|---|---|---|---|
| | | 195 | | | | | 200 | | | | | 205 | | | |

| Glu | Glu | Trp | Gly | Ser | Leu | Glu | Ala | Leu | Leu | Lys | Asn | Leu | Asp | Arg | Leu |
|---|---|---|---|---|---|---|---|---|---|---|---|---|---|---|---|
| 210 | | | | | 215 | | | | | 220 | | | | | |

| Lys | Pro | Ala | Ile | Arg | Glu | Lys | Ile | Leu | Ala | His | Met | Asp | Asp | Leu | Lys |
|---|---|---|---|---|---|---|---|---|---|---|---|---|---|---|---|
| 225 | | | | | 230 | | | | | 235 | | | | | 240 |

| Leu | Ser | Trp | Asp | Leu | Ala | Lys | Val | Arg | Thr | Asp | Leu | Pro | Leu | Glu | Val |
|---|---|---|---|---|---|---|---|---|---|---|---|---|---|---|---|
| | | | | 245 | | | | | 250 | | | | | 255 | |

| Asp | Phe | Ala | Lys | Arg | Arg | Glu | Pro | Asp | Arg | Glu | Arg | Leu | Arg | Ala | Phe |
|---|---|---|---|---|---|---|---|---|---|---|---|---|---|---|---|
| | | | 260 | | | | | 265 | | | | | 270 | | |

| Leu | Glu | Arg | Leu | Glu | Phe | Gly | Ser | Leu | Leu | His | Glu | Phe | Gly | Leu | Leu |
|---|---|---|---|---|---|---|---|---|---|---|---|---|---|---|---|
| | | 275 | | | | | 280 | | | | | 285 | | | |

| Glu | Ser | Pro | Lys | Ala | Leu | Glu | Glu | Ala | Pro | Trp | Pro | Pro | Pro | Glu | Gly |
|---|---|---|---|---|---|---|---|---|---|---|---|---|---|---|---|
| 290 | | | | | 295 | | | | | 300 | | | | | |

| Ala | Phe | Val | Gly | Phe | Val | Leu | Ser | Arg | Lys | Glu | Pro | Met | Trp | Ala | Asp |
|---|---|---|---|---|---|---|---|---|---|---|---|---|---|---|---|
| 305 | | | | | 310 | | | | | 315 | | | | | 320 |

| Leu | Leu | Ala | Leu | Ala | Ala | Ala | Arg | Gly | Gly | Arg | Val | His | Arg | Ala | Pro |
|---|---|---|---|---|---|---|---|---|---|---|---|---|---|---|---|
| | | | | 325 | | | | | 330 | | | | | 335 | |

| Glu | Pro | Tyr | Lys | Ala | Leu | Arg | Asp | Leu | Lys | Glu | Ala | Arg | Gly | Leu | Leu |

```
            340             345             350
Ala Lys Asp Leu Ser Val Leu Ala Leu Arg Glu Gly Leu Gly Leu Pro
            355             360             365
Pro Gly Asp Pro Met Leu Leu Ala Tyr Leu Leu Asp Pro Ser Asn
        370             375             380
Thr Thr Pro Glu Gly Val Ala Arg Arg Tyr Gly Gly Glu Trp Thr Glu
385             390             395             400
Glu Ala Gly Glu Arg Ala Ala Leu Ser Glu Arg Leu Phe Ala Asn Leu
                405             410             415
Trp Gly Arg Leu Glu Gly Glu Arg Leu Leu Trp Leu Tyr Arg Glu
            420             425             430
Val Glu Arg Pro Leu Ser Ala Val Leu Ala His Met Glu Ala Thr Gly
            435             440             445
Val Arg Leu Asp Val Ala Tyr Leu Arg Ala Leu Ser Leu Glu Val Ala
        450             455             460
Glu Glu Ile Ala Arg Leu Glu Ala Glu Val Phe Arg Leu Ala Gly His
465             470             475             480
Pro Phe Asn Leu Asn Ser Arg Asp Gln Leu Glu Arg Val Leu Phe Asp
            485             490             495
Glu Leu Gly Leu Pro Ala Ile Gly Lys Thr Glu Lys Thr Gly Lys Arg
            500             505             510
Ser Thr Ser Ala Ala Val Leu Glu Ala Leu Arg Glu Ala His Pro Ile
        515             520             525
Val Glu Lys Ile Leu Gln Tyr Arg Glu Leu Thr Lys Leu Lys Ser Thr
        530             535             540
Tyr Ile Asp Pro Leu Pro Asp Leu Ile His Pro Arg Thr Gly Arg Leu
545             550             555             560
His Thr Arg Phe Asn Gln Thr Ala Thr Ala Thr Gly Arg Leu Ser Ser
            565             570             575
Ser Asp Pro Asn Leu Gln Asn Ile Pro Val Arg Thr Pro Leu Gly Gln
            580             585             590
Arg Ile Arg Arg Ala Phe Ile Ala Glu Glu Gly Trp Leu Leu Val Ala
            595             600             605
Leu Asp Tyr Ser Gln Ile Glu Leu Arg Val Leu Ala His Leu Ser Gly
            610             615             620
Asp Glu Asn Leu Ile Arg Val Phe Gln Glu Gly Arg Asp Ile His Thr
625             630             635             640
Glu Thr Ala Ser Trp Met Phe Gly Val Pro Arg Glu Ala Val Asp Pro
                645             650             655
Leu Met Arg Arg Ala Ala Lys Thr Ile Asn Phe Gly Val Leu Tyr Gly
            660             665             670
Met Ser Ala His Arg Leu Ser Gln Glu Leu Ala Ile Pro Tyr Glu Glu
            675             680             685
Ala Gln Ala Phe Ile Glu Arg Tyr Phe Gln Ser Phe Pro Lys Val Arg
        690             695             700
Ala Trp Ile Glu Lys Thr Leu Glu Glu Gly Arg Arg Arg Gly Tyr Val
705             710             715             720
Glu Thr Leu Phe Gly Arg Arg Arg Tyr Val Pro Asp Leu Glu Ala Arg
                725             730             735
Val Lys Ser Val Arg Glu Ala Ala Glu Arg Met Ala Phe Asn Met Pro
            740             745             750
Val Gln Gly Thr Ala Ala Asp Leu Met Lys Leu Ala Met Val Lys Leu
            755             760             765
```

| Phe | Pro | Arg | Leu | Glu | Glu | Met | Gly | Ala | Arg | Met | Leu | Leu | Gln | Val | His |
|---|---|---|---|---|---|---|---|---|---|---|---|---|---|---|---|
| | 770 | | | | 775 | | | | | 780 | | | | | |

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 14
<211> LENGTH: 5487
<212> TYPE: DNA
<213> ORGANISM: Unknown
<220> FEATURE:
<223> OTHER INFORMATION: Bacterial plasmid1 used as PCR target

<400> SEQUENCE: 14

```
tttgctcaca tgacccgaca ccatcgaatg gccagatgat taattcctaa ttttgttga      60
cactctatca ttgatagagt tattttacca ctccctatca gtgatagaga aaagtgaaat    120
gaatagttcg acaaaaatct agataacgag ggcaaaaaat ggctagctgg agccacccgc    180
agttcgaaaa aggcgccatg atactggaca ctgattacat aacaaaagat ggtaaaccta    240
taatccgaat ttttaagaaa gagaacgggg agtttaaaat agaacttgat ccccattttc    300
agccctatat atatgctctt ctcaaagatg actccgctat tgaggagata aaggcaataa    360
agggcgagag acatggaaaa agtgtgagag tagttgatgc agtgaaagtc aagaagaaat    420
ttttgggaag ggaagttgag gtctggaagc ttatatttga acaccctcaa gacgttccgg    480
ctatgaggga caagataaaa gagcatccag ctgttatcga catttacgaa tatgatatac    540
catttgccaa gcgttatctc atagacaagg gcttgattcc tatggaggga gacgaggagc    600
ttaagctcct cgccttttga cattgaaacg tttatcatga aggagatgaa tttggaaaag    660
gcgagataat aatgattagt tatgccgacg aagaagaggc cagagtaatt acatggaaaa    720
atatcgatct gccgtatgtc gatgttgtat ccaatgaaag ggagatgata aagcgctttg    780
ttcaggttgt taaagaaaaa gacccggatg tgataataac ttacaatggg acaatttttg    840
atttgccgta tctcataaaa cgggcagaaa agctgggggt tcggcttgtc ttaggaaggg    900
acaaggaaaa tccgaacccc aagatccaga gaatggggga tagcttcgct gtagaaatca    960
agggcagaat acattttgat cttttcccag ttgtgagaag gacaataaac cttccgacgt   1020
atacgcttga ggcggtttat gaagcagttt tgggaaaaac caaaagcaaa ttaggagcgg   1080
aggaaattgc cgccatctgg gaaacggaag agagcatgaa aaaactggcc cagtactcaa   1140
tggaagatgc tagggcgact tatgagctcg gaaaggaatt cttccccatg gaagctgagc   1200
tggcgaagct gataggtcaa agcgtgtggg atgtctctag gtcaagcacc ggcaacctcg   1260
tggagtggta tttgttaagg gtggcatatg agaggaacga gcttgctccg aacaaacctg   1320
atgaggaaga gtataaaaga cgtttaagaa caacttacct gggaggatat gtaaaagagc   1380
cagaaaaggg tttatgggag aacatcatct atcttgactt ccgtagcttg tatccctcaa   1440
taatagttac ccataacgta tcgccggaca ctctcgaaaa agagggttgc gaaaattatg   1500
atattgctcc catagtaagc tataggttct gcaaggactt tccgggcttt attccctcca   1560
tactcgggga cttaattgca atgaggcaag agataaagaa gaaaatgaaa gctacaattg   1620
atccagtgga aaggaaaatg cttgattata gacaacgggc agttaaatta cttgcaaata   1680
```

```
gttattacgg ttatatgggg tatcctaagg caagatggta ctcgaaggaa tgtgccgaaa    1740
gtgttaccgc atggggaagg cactacatag agatgacgat aaaagaaata gaggaaaaat    1800
ttggctttaa agttctttat gcagacaccg acgggtttta tgcgacaata tcaggagaaa    1860
aaccggaaat tattaaaaag aaagccaggg agttcctaaa ctacataaac tctaaacttc    1920
caggtctgct tgagcttgag tatgagggct tttacttgag aggattcttt gttacaaaaa    1980
agcgctatgc agtcatagat gaagagggca gaataacaac aaggggcttg aagtagtaa     2040
ggagggactg gagtgaaata gctaaagaga ctcaggcaaa ggttttagag gctatactta    2100
aagatggaag tgttgaaaaa gctgtagaaa ttgttagaga tgttttagag aaaatagcaa    2160
aatacagggt tccacttgaa aagcttgtta tccatgagca gattaccagg gatttaaagg    2220
actacaaagc cattggtcct catgtagcga tagcaaaaag actagccgca agagggataa    2280
aagtgaaacc gggcacaata ataagctata tcgttctcaa aggaagcgga aagataagcg    2340
atagggtaat tttacttaca gaatacgatc ctgaaaagca caagtacgat ccagattact    2400
acatagaaaa ccaagttttg ccggcagtac ttagaatcct tgaagcattt ggatatagaa    2460
aggaggattt aagatatcaa agctcaaaac aaaccggctt agatgcatgg ctcaaaaggt    2520
gatatctaac taagcttgac ctgtgaagtg aaaaatggcg cacattgtgc gacattttt     2580
ttgtctgccg tttaccgcta ctgcgtcacg gatctccacg cgcctgtag cggcgcatta     2640
agcgcggcgg gtgtggtggt tacgcgcagc gtgaccgcta cacttgccag cgccctagcg    2700
cccgctcctt tcgctttctt cccttccttt ctcgccacgt tcgccggctt tccccgtcaa    2760
gctctaaatc gggggctccc tttagggttc gatttagtg ctttacggca cctcgacccc     2820
aaaaaacttg attagggtga tggttcacgt agtgggccat cgccctgata acggtttt      2880
cgccctttga cgttggagtc cacgttcttt aatagtggac tcttgttcca aactggaaca    2940
acactcaacc ctatctcggt ctattctttt gatttataag ggattttgcc gatttcggcc    3000
tattggttaa aaaatgagct gatttaacaa aaatttaacg cgaatttaa caaaatatta     3060
acgcttacaa tttcaggtgg cacttttcgg ggaaatgtgc gcggaacccc tatttgttta    3120
tttttctaaa tacattcaaa tatgtatccg ctcatgagac aataaccctg ataaatgctt    3180
caataatatt gaaaaaggaa gagtatgagt attcaacatt tccgtgtcgc ccttattccc    3240
tttttttgcgg catttgcct tcctgttttt gctcacccag aaacgctggt gaaagtaaaa     3300
gatgctgaag atcagttggg tgcacgagtg ggttacatcg aactggatct caacagcggt    3360
aagatccttg agagttttcg ccccgaagaa cgttttccaa tgatgagcac ttttaaagtt    3420
ctgctatgtg gcgcggtatt atcccgtatt gacgccgggc aagagcaact cggtcgccgc    3480
atacactatt ctcagaatga cttggttgag tactcaccag tcacagaaaa gcatcttacg    3540
gatggcatga cagtaagaga attatgcagt gctgccataa ccatgagtga taacactgcg    3600
gccaacttac ttctgacaac gatcggagga ccgaaggagc taaccgcttt tttgcacaac    3660
atggggggatc atgtaactcg ccttgatcgt tgggaaccgg agctgaatga agccatacca    3720
aacgacgagc gtgacaccac gatgcctgta gcaatggcaa caacgttgcg caaactatta    3780
actggcgaac tacttactct agcttcccgg caacaattga tagactggat ggaggcggat    3840
aaagttgcag gaccacttct gcgctcggcc cttccggctg gctggtttat tgctgataaa    3900
tctggagccg gtgagcgtgg ctctcgcggt atcattgcag cactggggcc agatggtaag    3960
ccctcccgta tcgtagttat ctacacgacg gggagtcagg caactatgga tgaacgaaat    4020
agacagatcg ctgagatagg tgcctcactg attaagcatt ggtaggaatt aatgatgtct    4080
```

```
cgtttagata aaagtaaagt gattaacagc gcattagagc tgcttaatga ggtcggaatc    4140
gaaggtttaa caacccgtaa actcgcccag aagctaggtg tagagcagcc tacattgtat    4200
tggcatgtaa aaaataagcg ggctttgctc gacgccttag ccattgagat gttagatagg    4260
caccatactc acttttgccc tttagaaggg gaaagctggc aagatttttt acgtaataac    4320
gctaaaagtt ttagatgtgc tttactaagt catcgcgatg gagcaaaagt acatttaggt    4380
acacggccta cagaaaaaca gtatgaaact ctcgaaaatc aattagcctt tttatgccaa    4440
caaggttttt cactagagaa tgcattatat gcactcagcg cagtggggca ttttacttta    4500
ggttgcgtat tggaagatca agagcatcaa gtcgctaaag aagaagggga aacacctact    4560
actgatagta tgccgccatt attacgacaa gctatcgaat tatttgatca ccaaggtgca    4620
gagccagcct tcttattcgg ccttgaattg atcatatgcg gattagaaaa acaacttaaa    4680
tgtgaaagtg ggtcttaaaa gcagcataac cttttccgt gatggtaact tcactagttt    4740
aaaaggatct aggtgaagat ccttttgat aatctcatga ccaaaatccc ttaacgtgag    4800
ttttcgttcc actgagcgtc agacccgta gaaaagatca aaggatcttc ttgagatcct    4860
ttttttctgc gcgtaatctg ctgcttgcaa acaaaaaaac caccgctacc agcggtggtt    4920
tgtttgccgg atcaagagct accaactctt tttccgaagg taactggctt cagcagagcg    4980
cagataccaa atactgtcct tctagtgtag ccgtagttag gccaccactt caagaactct    5040
gtagcaccgc ctacatacct cgctctgcta atcctgttac cagtggctgc tgccagtggc    5100
gataagtcgt gtcttaccgg gttggactca agacgatagt taccggataa ggcgcagcgg    5160
tcgggctgaa cggggggttc gtgcacacag cccagcttgg agcgaacgac ctacaccgaa    5220
ctgagatacc tacagcgtga gctatgagaa agcgccacgc ttcccgaagg gagaaaggcg    5280
gacaggtatc cggtaagcgg cagggtcgga acaggagagc gcacgaggga gcttccaggg    5340
ggaaacgcct ggtatcttta tagtcctgtc gggtttcgcc acctctgact tgagcgtcga    5400
tttttgtgat gctcgtcagg ggggcggagc ctatggaaaa acgccagcaa gcggcctttt    5460
ttacggttcc tggccttttg ctggcct                                       5487
```